United States Patent [19]
Chatterjee

[11] Patent Number: 5,852,007
[45] Date of Patent: Dec. 22, 1998

[54] CYSTEINE AND SERINE PROTEASE INHIBITORS CONTAINING D-AMINO ACID AT THE P2 POSITION, METHODS OF MAKING SAME, AND METHODS OF USING SAME

[75] Inventor: Sankar Chatterjee, Wynnewood, Pa.

[73] Assignee: Cephalon, Inc., West Chester, Pa.

[21] Appl. No.: 795,546

[22] Filed: Feb. 6, 1997

Related U.S. Application Data

[63] Continuation-in-part of Ser. No. 755,839, Nov. 26, 1996, abandoned.

[60] Provisional application No. 60/007,651 Nov. 28, 1995.

[51] Int. Cl.$^6$ .......... A61K 31/27; A61K 31/195; A61K 31/16; A61K 31/40; A61K 31/395; A61K 31/445; C07D 205/04; C07D 207/16; C07D 401/12; C07D 401/06; C07D 401/14; C07D 333/16

[52] U.S. Cl. .......... 514/183; 514/183; 514/238.2; 514/307; 514/312; 514/380; 514/398; 514/407; 514/414; 514/417; 514/419; 514/424; 514/438; 514/439; 514/618; 514/620; 540/483; 544/159; 546/146; 546/153; 548/243; 548/300.1; 548/324.5; 548/370.1; 548/465; 548/479; 548/495; 548/542; 549/30; 549/65; 564/79; 564/84; 564/90; 564/92; 564/95; 564/185; 564/188

[58] Field of Search .......... 548/300.1, 243, 548/324.5, 465, 495, 370.1, 479, 542; 564/79, 84, 90, 92, 95, 185, 188; 514/307, 312, 407, 147, 620, 618, 238.3, 435, 380, 398, 419, 414, 183, 424, 439; 540/483; 544/159; 549/65, 30; 546/146, 153

[56] References Cited

U.S. PATENT DOCUMENTS

| | | | |
|---|---|---|---|
| 4,518,528 | 5/1985 | Rasnick | 260/112.5 R |
| 4,596,789 | 6/1986 | Dutta et al. | 514/18 |
| 4,691,007 | 9/1987 | Dutta et al. | 530/331 |
| 5,328,916 | 7/1994 | Raddatz et al. | 514/318 |
| 5,436,229 | 7/1995 | Ruterbories et al. | 514/18 |
| 5,444,042 | 8/1995 | Bartus et al. | 514/2 |
| 5,514,694 | 5/1996 | Powers et al. | 514/357 |
| 5,536,639 | 7/1996 | Siman et al. | 435/7.1 |
| 5,541,290 | 7/1996 | Harbeson et al. | 530/330 |

FOREIGN PATENT DOCUMENTS

| | | |
|---|---|---|
| 0 293 881 B1 | 12/1988 | European Pat. Off. . |
| 0 363 284 A2 | 4/1990 | European Pat. Off. . |
| 0 520 336 A2 | 12/1992 | European Pat. Off. . |
| 0 604 182 A2 | 6/1994 | European Pat. Off. . |
| 0 604 184 A1 | 6/1994 | European Pat. Off. . |
| 0 604 185 A1 | 6/1994 | European Pat. Off. . |
| 0 604 186 A1 | 6/1994 | European Pat. Off. . |
| WO 92/11850 | 7/1992 | WIPO . |
| WO 92/12140 | 7/1992 | WIPO . |
| WO 92/14696 | 9/1992 | WIPO . |
| WO 93/25667 | 12/1993 | WIPO . |
| WO 94/00095 | 1/1994 | WIPO . |
| WO 94/00488 | 1/1994 | WIPO . |
| WO 95/00535 | 1/1995 | WIPO . |
| WO 95/24914 | 9/1995 | WIPO . |
| WO 96/39194 | 12/1996 | WIPO . |

OTHER PUBLICATIONS

Bajusz et al., "Inhibition of Thrombin and Trypsin by Tripeptide Aldehydes", *Int. J. Peptide Protein Res.*, 1978, 12, 217–221.

Bajusz et al., "Highly Active and Selective Anticoagulatns: D–Phe–Pro–Arg–H, a Free Tripeptide Aldehyde Prone to Spontaneous Inactivation, and Its Stable N–Methyl Derivative, D–MePhe–Pro–Arg–H", *J. Med. Chem.*, 1990, 33, 1729–1735.

Esser et al., "New amino acid derivative are neurokinin antagonists–useful for treating and preventing respiratory diseases, inflammatory diseases, gastrointestinal diseases and pain disorders", Document No. DE4406884–A1, Inhelheim, Germany, 1995, 2 pages.

Fehrentz et al., "An Efficient Synthesis of Optically Active α–(t–Butoxycarbonylamino)–aldehydes from α1Amino Acids", *Synthesis*, 1983, 676–678.

Flynn et al., "A Mild Two–Step Method for the Hydrolysis/Methanolysis of Secondary Amides and Lactams", *J. Org. Chem.*, 1983, 48, 2424–2426.

Green, T.W. and Wuts, P.G.M., *Protective Groups in Organic Synthesis*, 2d Edition, Wiley & Sons, 1991.

Harbeson et al., "Stereospecific Synthesis of Peptidyl α–Keto Amides as Inhibitors of Calpain", *J. Med. Chem.*, 1994, 37, 2918–2929.

Imperiali et al., "A Versatile Synthesis of Peptidyl Fluoromethyl Ketones", *Tetra. Lett.*, 1986, 27(2), 135–138.

Jungheim et al., "Potent Human Immunodeficiency Virus Type 1 Protease Inhibitors That Utilize Noncoded D–Amino Acids as P$_2$/P$_3$ Ligands", *J. Med. Chem.*, 1996, 39, 96–108.

Kettner et al., "The Selective Inhibition of Thrombin by Peptides of Boroarginine", *J. Biol. Chem.*, 1990, 265(30), 18289–18297.

Lehninger, *Biochemistry*, Second Edition, Worth Publishers, Inc., 1975, 73–75.

Li et al., "Novel Peptidyl α–Keto Amide Inhibitors of Calpains and Other Cysteine Proteases", *J. Med. Chem.*, 1996, 39, 4089–4098.

Luly et al., "A Synthesis of Protected Aminoalkyl Epoxides from α–Amino Acids", *J. Org. Chem.*, 1987, 52(8), 1487–1492.

Meyer et al., "Biologically active monomeric and heterodimeric recombinant human calpain I produced using the baculovirus expression system", *Biochem. J.*, 1996, 314, 511–519.

(List continued on next page.)

*Primary Examiner*—Floyd D. Higel
*Attorney, Agent, or Firm*—Woodcock Washburn Kurtz Mackiewicz & Norris LLP

[57] ABSTRACT

The present invention is directed to (D)-amino acid containing inhibitors of cysteine or serine proteases. Methods for the use of the protease inhibitors are also described.

43 Claims, 2 Drawing Sheets

OTHER PUBLICATIONS

Mitsunobu, "The Use of Diethyl Azodicarboxylate and Triphenylphosphine in Synthesis and Transformation of Natural Product", *Synthesis,* 1981, 1–28.

Nagai et al., "Poststatin, A New Inhibitor of Prolyl Endopeptidase, Produced by *Streptomyces viridochromogenes* MH5324–30F3", *J. Antibiotics,* 1991, 956–961.

Patel et al., "Activated Ketone Based Inhibitors of Human Renin", *J. Med. Chem.,* 1993, 36(17), 2431–2447.

*Remington's Pharmaceutical Sciences,* Mack Publishing Co., Easton, PA, 1980.

Revesz et al., "Synthesis of P1 Aspartate–Based Peptide Acyloxymethy and Fluoromethyl Ketones as Inhibitors of Interleukin–1β–Converting Enzyme", *Tetra. Lett.,* 1994, 35(52), 9693–9696.

Roller et al., "Complementary peptides as inhibitors of HIV–1 protease", *Peptides: Chemistry and Biology,* 12th, Smith, J.A. et al. (Eds.), 1992, 709–710.

Schechter et al., "On The Size of the Active Site in Proteases. I. Papain", *Biophys. Res. Commun.,* 1967, 27(2), 157–162.

Shepherd et al., "D–Amino Acids as Novel $P_2/P_3$ Ligands for Inhibitors of HIV–1 Protease", *Bioorganic Medicinal Chem. Lett.,* 1994, 4(11), 1391–1396.

Yahi et al., "Multibranched V3 Peptides Inhibit Human Immunodeficiency Virus Infection in Human Lymphocytes and Macrophages", *J. Virology,* 1994, 68(9), 5714–5720.

CYSTEINE AND SERINE PROTEASE INHIBITORS CONTAINING D-AMINO ACID AT THE P2 POSITION, METHODS OF MAKING SAME, AND METHODS OF USING SAME

CROSS REFERENCE TO RELATED APPLICATIONS

This is a continuation-in-part of U.S. application Ser. No. 08/755,839, filed Nov. 26, 1996, (now abandoned) and U.S. Provisional application Ser. No. 60/007,651, filed Nov. 28, 1995, the disclosures of each of which are herby incorporated herein by reference in their entireties.

FIELD OF THE INVENTION

P2 (D)-amino acid inhibitors of cysteine or serine proteases, methods for making these compounds, and methods for using the same are disclosed.

BACKGROUND OF THE INVENTION

Numerous cysteine and serine proteases have been identified in human tissues. A "protease" is an enzyme which degrades proteins into smaller components (peptides). The terms "cysteine protease" and "serine protease" refer to proteases which are distinguished by the presence therein of a cysteine or serine residue which plays a critical role in the catalytic process. Mammalian systems, including humans, normally degrade and process proteins via a variety of enzymes including cysteine and serine proteases. However, when present at elevated levels or when abnormally activated, cysteine and serine proteases may be involved in pathophysiological processes.

For example, calcium-activated neutral proteases ("calpains") comprise a family of intracellular cysteine proteases which are ubiquitously expressed in mammalian tissues. Two major calpains have been identified; calpain I and calpain II. While calpain II is the predominant form in many tissues, calpain I is thought to be the predominant form active in pathological conditions of nerve tissues. The calpain family of cysteine proteases has been implicated in many diseases and disorders, including neurodegeneration, stroke, Alzheimer's, amyotrophy, motor neuron damage, acute central nervous system injury, muscular dystrophy, bone resorption, platelet aggregation, cataracts and inflammation. Calpain I has been implicated in excitatory amino-acid induced neurotoxicity disorders including ischemia, hypoglycemia, Huntington's Disease, and epilepsy.

The lysosomal cysteine protease cathepsin B has been implicated in the following disorders: arthritis, inflammation, myocardial infarction, tumor metastasis, and muscular dystrophy. Other lysosomal cysteine proteases include cathepsins C, H, L and S. Interleukin-1β converting enzyme ("ICE") is a cysteine protease which catalyzes the formation of interleukin-1β. Interleukin-1β is an immunoregulatory protein implicated in the following disorders: inflammation, diabetes, septic shock, rheumatoid arthritis, and Alzheimer's disease. ICE has also been linked to apoptotic cell death of neurons, which is implicated in a variety of neurodegenerative disorders including Parkinson's disease, ischemia, and amyotrophic lateral sclerosis (ALS).

Cysteine proteases are also produced by various pathogens. The cysteine protease clostripain is produced by *Clostridium histolyticum*. Other proteases are produced by *Trypanosoma cruzi*, malaria parasites *Plasmodium falciparum* and *P. vinckei* and Streptococcus. Hepatitis A viral protease HAV C3 is a cysteine protease essential for processing of picornavirus structural proteins and enzymes.

Exemplary serine proteases implicated in degenerative disorders include thrombin, human leukocyte elastase, pancreatic elastase, chymase and cathepsin G. Specifically, thrombin is produced in the blood coagulation cascade, cleaves fibrinogen to form fibrin and activates Factor VIII; thrombin is implicated in thrombophlebitis, thrombosis and asthma. Human leukocyte elastase is implicated in tissue degenerative disorders such as rheumatoid arthritis, osteoarthritis, atherosclerosis, bronchitis, cystic fibrosis, and emphysema. Pancreatic elastase is implicated in pancreatitis. Chymase, an enzyme important in angiotensin synthesis, is implicated in hypertension, myocardial infarction, and coronary heart disease. Cathepsin G is implicated in abnormal connective tissue degradation, particularly in the lung.

Given the link between cysteine and serine proteases and various debilitating disorders, compounds which inhibit these proteases would be useful and would provide an advance in both research and clinical medicine. The present invention is directed to these, as well as other, important ends.

SUMMARY OF THE INVENTION

The present invention is directed to novel cysteine and serine protease inhibitors which contain a (D)-amino acid at the P2 position. Exemplary compounds are represented by the following Formula I:

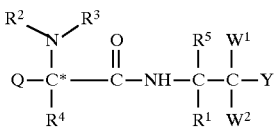

s wherein:

C* denotes a carbon atom having a D-configuration;

Q has the formula G-B-(CHR$^{20}$)$_q$— where R$^{20}$ is independently H or alkyl having from 1 to 4 carbons;

q is 0, 1, or 2;

B is selected from the group consisting of C(=O), S(=O), S(=O)$_2$, S, CH$_2$, a bond, NH and O;

G is selected from the group consisting of aryl having from about 6 to about 14 carbons, heteroaryl having from about 5 to about 14 ring atoms, aralkyl having from about 7 to about 15 carbons, alkyl having from 1 to about 10 carbons, heteroalkyl having from 2 to about 7 carbons, alkoxy having from 1 to about 10 carbons, arylsulfonyl, alkylsulfonyl, aralkyloxy having from about 7 to about 15 carbons, amino, and a carbohydrate moiety optionally containing one or more alkylated hydroxyl groups, said aryl, heteroaryl, aralkyl, alkyl and amino groups being optionally substituted with one or more K groups;

K is selected from the group consisting of halogen, CN, NO$_2$, lower alkyl, aryl, heteroaryl, aralkyl, aralkyloxy, guanidino, alkoxycarbonyl, alkoxy, hydroxy, carboxy, and amino, said amino group being optionally substituted with an acyl group or with 1 to 3 aryl or lower alkyl groups;

R$^1$ is selected from the group consisting of H, alkyl having from one to about 14 carbons, cycloalkyl having from 3 to about 10 carbons, aralkyl having from about 7 to about 15 carbons, heteroarylalkyl in which the heteroaryl ring contains from about 5 to about 14 ring atoms, a natural side chain of a D- or L-amino acid, and an unnatural side chain of a D- or L-amino acid, said alkyl, cycloalkyl, aralkyl, and heteroarylalkyl groups being optionally substituted with one or more K groups;

$R^2$ is selected from the group consisting of $C(=O)R^6$, $S(=O)_2R^6$, and a protecting group;

$R^6$ is selected from the group consisting of aryl having from about 6 to about 14 carbons, heteroaryl having from about 5 to about 14 ring atoms, aralkyl having from about 7 to about 15 carbons, alkyl having from 1 to about 10 carbons, said aryl, heteroaryl, aralkyl and alkyl groups being optionally substituted with one or more K groups, heteroalkyl having from 2 to about 7 carbons, alkoxy having from 1 to about 10 carbons, and amino optionally substituted with 1 or more alkyl groups;

$R^3$ is selected from the group consisting of H, lower alkyl, aralkyl, and a group of formula —$CO_2$—$R^{21}$ where $R^{21}$ is a lower alkyl group;

or $R^3$ may be taken together with $R^2$ to form a phthalimido group;

or Q and $R^3$ taken together with —C* and —$N(R^2)$— may form a group of formula:

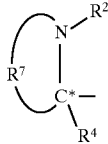

where $R^7$ is alkylene having from 2 to 5 carbons, said alkylene group optionally containing a carboncarbon double bond, said alkylene group being optionally substituted with a group selected from the group consisting of aryl, azide, CN, a protected amino group, and $OSO_2$-aryl, wherein said aryl group is optionally substituted with one or more K groups, said aryl portion of said $OSO_2$-aryl group being optionally substituted with one or more K groups;

or $R^7$ may have the formula:

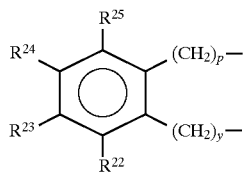

where p and y are independently 0 or 1, and $R^{22}$, $R^{23}$, $R^{24}$, and $R^{25}$ are indepenedently H or a K group;

$R^4$ and $R^5$ are each independently selected from the group consisting of H and lower alkyl;

$W^1$ and $W^2$ are selected such that $W^1$ is H and $W^2$ is $OC(=O)NH$—$R^{26}$ where $R^{26}$ is alkyl, or $W^1$ and $W^2$ are both alkoxy, or $W^1$ is OH and $W^2$ is selected from the group consisting of aralkyl, aralkyloxy, aryloxy, heteroaryloxy, heteroaralkyloxy, and $SO_3Z^1$ where $Z^1$ which is preferably Group I or Group II counterion, preferably Na; or $W^1$ and $W^2$ taken together may form a group selected from the group consisting of $=O$, $=NR^8$, $=N(\rightarrow O)R^9$, —$S(CH_2)_2O$—, and —$N(R^{12})(CH_2)_2N(R^{12})$—;

$R^8$ is selected from the group consisting of $NH(C=O)NH_2$, hydroxyl, and lower alkoxy;

$R^9$ is selected from the group consisting of alkyl and aralkyl;

$R^{12}$ is selected from the group consisting of alkyl having from 1 to 4 carbons, and phenyl;

Y is selected from the group consisting of H, $C(=O)NR^{10}R^{11}$, $C(=O)OR^{10}$, $CH=N_2$, and $CH_2R^{13}$; or Y and $R^1$ taken together may form —$(CH_2)_4N(Pr)$— where Pr is H or a protecting group, provided that when Y and $R^1$ are taken together to form —$(CH_2)_4N(Pr)$—, then $W^1$ and $W^2$ are taken together to form $=O$;

$R^{10}$ and $R^{11}$ are each independently selected from the group consisting of H, alkyl having from 1 to about 10 carbons, said alkyl groups being optionally substituted with one or more K groups, aryl having from about 6 to about 14 carbons, and aralkyl having from about 7 to about 15 carbons;

$R^{13}$ is selected from the group consisting of L, lower alkyl, aralkyl, halogen, and a group O-M, wherein M has the structure:

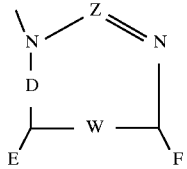

wherein:

Z is selected from the group consisting of N and $CR^{14}$;

W is selected from the group consisting of a double bond and a single bond;

D is selected from the group consisting of C=O and a single bond;

E and F are independently selected from the group consisting of $R^{14}$, $R^{15}$, and J;

or E and F taken together comprise a joined moiety, said joined moiety being selected from the group consisting of an aliphatic carbocyclic ring having from 5 to 7 carbons, an aromatic carbocyclic ring having from 5 to 7 carbons, an aliphatic heterocyclic ring having from 5 to 7 atoms and containing from 1 to 4 heteroatoms, and an aromatic heterocyclic ring having from 5 to 7 atoms and containing from 1 to 4 heteroatoms, said aliphatic carbocyclic ring, aromatic carbocyclic ring, aliphatic heterocyclic ring, and aromatic heterocyclic ring each being optionally substituted with J;

$R^{14}$ and $R^{15}$ are independently selected from the group consisting of H, alkyl having from 1 to 10 carbons, heteroaryl having from 1 to 10 carbons, alkanoyl having from 1 to 10 carbons, and aroyl, wherein said alkyl, heteroaryl, alkanoyl and aroyl groups are optionally substituted with J;

J is selected from the group consisting of halogen, $C(=O)OR^{16}$, $R^{16}OC(=O)$, $R^{16}OC(=O)NH$, OH, CN, $NO_2$, $NR^{16}R^{17}$, $N=C(R^{16})R^{17}$, $N=C(NR^{16}R^{17})_2$, $SR^{16}OR^{16}$, phenyl, napththyl, heteroaryl, and a cycloalkyl group having from 3 to 8 carbons;

$R^{16}$ and $R^{17}$ are independently H, alkyl having from 1 to 10 carbons, aryl, or heteroaryl, wherein said alkyl, aryl and heteroaryl groups are optionally substituted with K;

L is a phosphorus-containing enzyme reactive group, which preferably has the formula:

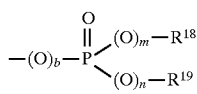

wherein:
m, n, and b are each independently 0 or 1;
$R^{18}$ and $R^{19}$ are each independently selected from the group consisting of H, lower alkyl optionally substituted with K, aryl optionally substituted with K, and heteroaryl optionally substituted with K;
or $R^{18}$ and $R^{19}$ taken together with —(O)$_m$—P(=O)—(O)$_n$— can form a 5–8 membered ring containing up to 3 hetero atoms,
or $R^{18}$ and $R^{19}$ taken together with —(O)$_m$—P(=O)—(O)$_n$—can form a 5–8 membered ring optionally substituted with K.

In some preferred embodiments of the compounds of Formula I, G is alkyl, benzyl, tetrahydroisoquinolyl, 3-indolyl, phenyl, N-methylbenzylamino, substituted benzyl, 2-thienyl or p-benzyloxyphenyl. In other preferred embodiments of the compounds of Formula I Q and $R^3$ taken together have a formula selected from the group consisting of —(CH$_2$)$_3$—, —CH$_2$—CH(OSO$_2$C$_6$H$_5$)—CH$_2$—, —CH$_2$—CH(OSO$_2$C$_6$H$_4$CH$_3$)—CH$_2$—, —CH$_2$—CH(N$_3$)—CH$_2$—, —CH$_2$—CH(CN)—CH$_2$—, —CH$_2$—CH=CH—, and

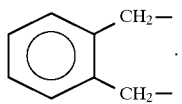

In other preferred embodiments of the compounds of Formula I, B is selected from the group consisting of —C(=O)—, —O—, —S—, —S(=O)$_2$—, and a bond.

In further preferred embodiments of the compounds of Formula I $R^1$ is selected from the group consisting of benzyl, substituted benzyl, a lysyl side chain, or a substituted lysyl side chain. In more preferred embodiments $R^1$ is alkyl, preferably ethyl, isobutyl, or t-butyl, benzyl, p-benzyloxybenzyl, 2-pyridylmethyl, —(CH$_2$)$_4$—NHC(=O)—O—CH$_2$—C$_6$H$_5$, —(CH$_2$)$_4$—NHC(=O)—O—t—C$_4$H$_9$, or —(CH$_2$)$_4$—NHSO$_2$—C$_6$H$_5$.

In other preferred embodiments of the compounds of Formula I $W^1$ and $W^2$ taken together form —C(=O), and $R^1$ and Y together form —(CH$_2$)$_4$—N(Pr)— where Pr is H or t-butoxycarbonyl.

In some preferred embodiments of the compounds of Formula I $R^2$ is selected from the group consisting of t-butyloxycarbonyl, —S(=O)$_2$R$^6$, and —C(=O)CH$_3$. More preferably, $R^2$ is —S(=O)$_2$R$^6$, said $R^6$ being selected from the group consisting of substituted or unsubstituted alkyl, substituted or unsubstituted aryl, and substituted or unsubstituted heteroaryl. In still more preferred embodiments of the compounds of Formula I $R^2$ is selected from the group consisting of —S(=O)$_2$CH$_3$, —S(=O)$_2$CH$_2$CH$_3$, p-fluorophenylsulfonyl, —S(=O)$_2$N(CH$_3$)$_2$, 2-thienylsulfonyl, 2isoxazolesulfonyl, phenylsulfonyl, p-methylphenylsulfonyl, 4-(N-methylimidazole)sulfonyl, and 2-naphthylsulfonyl.

In other preferred embodiments of the compounds of Formula I Y is selected from the group consisting of H and CH$_2$F.

Preferably, $W^1$ and $W^2$ taken together form —C(=O), or $W^1$ and $W^2$ are selected such that $W^1$ is OH and $W^2$ is SO$_3$Z$^1$ where $Z^1$ is a group I counterion which is preferably Na, $W^1$ is H and $W^2$ is OC(=O)NH—R$^{26}$ where $R^{26}$ is alkyl, $W^1$ is OH and $W^2$ is aralkyl, $W^1$ is OH and $W^2$ is aralkyloxy, $W^1$ is OH and $W^2$ is aryloxy, $W^1$ is OH and $W^2$ is heteroaryloxy, $W^1$ is OH and $W^2$ is heteroaralkyloxy, $W^1$ and $W^2$ are both alkoxy, or $W^1$ and $W^2$ taken together form a group selected from the group consisting of =NR$^8$, =N(→O)R$^9$, —S(CH$_2$)$_2$O—, and —N(R$^{12}$)(CH$_2$)$_2$N(R$^{12}$)—.

In particularly preferred embodiments of the compounds of Formula I, B is selected from the group consisting of —(C=O)—, —O—, a bond, SO$_2$, and —S—; Y is selected from the group consisting of H and CH$_2$F; $R^1$ is selected from the group consisting of benzyl, substituted benzyl, a lysyl side chain, and a substituted lysyl side chain; and $R^2$ is selected from the group consisting of t-butyloxycarbonyl, —C(=O)CH$_3$, and —S(=O)$_2$R$^6$. Preferably, $R^6$ is selected from the group consisting of substituted or unsubstituted alkyl, substituted or unsubstituted aryl, and substituted and unsubstituted heteroaryl.

In an especially preferred embodiment, Q is benzyloxymethyl; $R^1$ is benzyl; $R^2$ is —SO$_2$CH$_3$; $R_3$, $R_4$, $R_5$ and Y are each H; and $W^1$ and $W^2$ together form —C(=O)—.

The compounds of the invention are useful for the inhibition of cysteine and serine proteases. Beneficially, the compounds find utility in a variety of settings. For example, in a research arena, the claimed compounds can be used, for example, as standards to screen for natural and synthetic cysteine protease and serine protease inhibitors which have the same or similar functional characteristics as the disclosed compounds. In a clinical arena, the subject compounds can be used to alleviate, mediate, reduce and/or prevent disorders which are associated with abnormal and/or aberrant activity of cysteine proteases and/or serine proteases. Accordingly, compositions containing the subject compounds, and methods for using the subject compounds, such as methods for inhibiting serine proteases or cysteine proteases comprising contacting said proteases with an inhibitory amount of a compound of the invention are disclosed. Methodologies for making the present (D)-amino acid containing inhibitors are also disclosed. Other useful ethodologies will be apparent to those skilled in the art, once armed with the present disclosure. These and other features of the compounds of the subject invention are set forth in more detail below.

DETAILED DESCRIPTION

Figure 1:
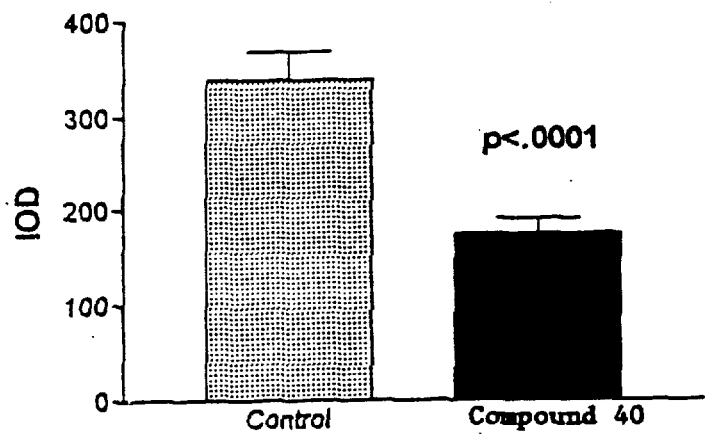
FIG. 1 shows the effect of Compound 40 on spectrin breakdown in the CA1 hippocampal sectors of gerbils.

Novel cysteine and serine protease inhibitors have been discovered which are represented by the general Formula

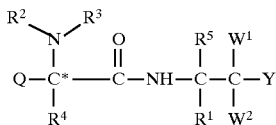

wherein:
C* denotes a carbon atom having a D-configuration;
Q has the formula G—B—(CHR$^{20}$)$_q$— where $R^{20}$ is independently H or alkyl having from 1 to 4 carbons;

q is 0, 1, or 2;

B is selected from the group consisting of C(=O), S(=O), S(=O)$_2$, S, CH$_2$, a bond, NH and O;

G is selected from the group consisting of aryl having from about 6 to about 14 carbons, heteroaryl having from about 5 to about 14 ring atoms, aralkyl having from about 7 to about 15 carbons, alkyl having from 1 to about 10 carbons, heteroalkyl having from 2 to about 7 carbons, alkoxy having from 1 to about 10 carbons, arylsulfonyl, alkylsulfonyl, aralkyloxy having from about 7 to about 15 carbons, amino, and a carbohydrate moiety optionally containing one or more alkylated hydroxyl groups, said aryl, heteroaryl, aralkyl, alkyl and amino groups being optionally substituted with one or more K groups;

K is selected from the group consisting of halogen, CN, NO$_2$, lower alkyl, aryl, heteroaryl, aralkyl, aralkyloxy, guanidino, alkoxycarbonyl, alkoxy, hydroxy, carboxy, and amino, said amino group being optionally substituted with an acyl group or with 1 to 3 aryl or lower alkyl groups;

$R^1$ is selected from the group consisting of H, alkyl having from one to about 14 carbons, cycloalkyl having from 3 to about 10 carbons, aralkyl having from about 7 to about 15 carbons, heteroarylalkyl in which the heteroaryl ring contains from about 5 to about 14 ring atoms, a natural side chain of a D- or L-amino acid, and an unnatural side chain of a D- or L-amino acid, said alkyl, cycloalkyl, aralkyl, and heteroarylalkyl groups being optionally substituted with one or more K groups;

$R^2$ is selected from the group consisting of C(=O)$R^6$, S(=O)$_2R^6$, and a protecting group;

$R^6$ is selected from the group consisting of aryl having from about 6 to about 14 carbons, heteroaryl having from about 5 to about 14 ring atoms, aralkyl having from about 7 to about 15 carbons, alkyl having from 1 to about 10 carbons, said aryl, heteroaryl, aralkyl and alkyl groups being optionally substituted with one or more K groups, heteroalkyl having from 2 to about 7 carbons, alkoxy having from 1 to about 10 carbons, and amino optionally substituted with 1 or more alkyl groups;

$R^3$ is selected from the group consisting of H, lower alkyl, aralkyl, and a group of formula —CO$_2$—$R^{21}$ where $R^{21}$ is a lower alkyl group;

or $R^3$ may be taken together with $R^2$ to form a phthalimido group;

or Q and $R^3$ taken together with —C* and —N($R^2$)— may form a group of formula:

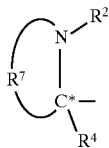

where $R^7$ is alkylene having from 2 to 5 carbons, said alkylene group optionally containing a carboncarbon double bond, said alkylene group being optionally substituted with a group selected from the group consisting of aryl, azide, CN, a protected amino group, and OSO$_2$-aryl, wherein said aryl group is optionally substituted with one or more K groups, said aryl portion of said OSO$_2$-aryl group being optionally substituted with one or more K groups;

or $R^7$ may have the formula:

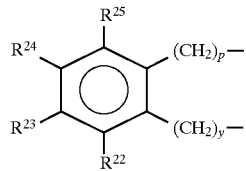

where p and y are independently 0 or 1, and $R^{22}$, $R^{23}$, $R^{24}$, and $R^{25}$ are indepenedently H or a K group;

$R^4$ and $R^5$ are each independently selected from the group consisting of H and lower alkyl;

$W^1$ and $W^2$ are selected such that $W^1$ is H and $W^2$ is OC(=O)NH—$R^{26}$ where $R^{26}$ is alkyl, or $W^1$ and $W^2$ are both alkoxy, or $W^1$ is OH and $W^2$ is selected from the group consisting of aralkyl, aralkyloxy, aryloxy, heteroaryloxy, heteroaralkyloxy, and SO$_3Z^1$ where $Z^1$ which is preferably Group I or Group II counterion, preferably Na; or $W^1$ and $W^2$ taken together may form a group selected from the group consisting of =O, =NR$^8$, =N(→O)R$^9$, —S(CH$_2$)$_2$O—, and —N(R$^{12}$)(CH$_2$)$_2$N(R$^{12}$)—;

$R^8$ is selected from the group consisting of NH(C=O)NH$_2$, hydroxyl, and lower alkoxy;

$R^9$ is selected from the group consisting of alkyl and aralkyl;

$R^{12}$ is selected from the group consisting of alkyl having from 1 to 4 carbons, and phenyl;

Y is selected from the group consisting of H, C(=O)NR$^{10}$R$^{11}$, C(=O)OR$^{10}$, CH=N$_2$, and CH$_2$R$^{13}$; or Y and $R^1$ taken together may form —(CH$_2$)$_4$N(Pr)— where Pr is H or a protecting group, provided that when Y and $R^1$ are taken together to form —(CH$_2$)$_4$N(Pr)—, then $W^1$ and $W^2$ are taken together to form =O;

$R^{10}$ and $R^{11}$ are each independently selected from the group consisting of H, alkyl having from 1 to about 10 carbons, said alkyl groups being optionally substituted with one or more K groups, aryl having from about 6 to about 14 carbons, and aralkyl having from about 7 to about 15 carbons;

$R^{13}$ is selected from the group consisting of L, lower alkyl, aralkyl, halogen, and a group O—M, wherein M has the structure:

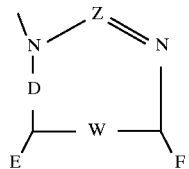

wherein:

Z is selected from the group consisting of N and CR$^{14}$;

W is selected from the group consisting of a double bond and a single bond;

D is selected from the group consisting of C=O and a single bond;

E and F are independently selected from the group consisting of R$^{14}$, R$^{15}$, and J;

or E and F taken together comprise a joined moiety, said joined moiety being selected from the group consisting of an aliphatic carbocyclic ring having from 5 to 7 carbons, an aromatic carbocyclic ring having from 5 to 7 carbons, an aliphatic heterocyclic ring having from 5 to 7 atoms and containing from 1 to 4 heteroatoms, and an aromatic heterocyclic ring having from 5 to 7 atoms and containing from 1 to 4 heteroatoms, said aliphatic carbocyclic ring, aromatic carbocyclic ring, aliphatic heterocyclic ring, and aromatic heterocyclic ring each being optionally substituted with J;

$R^{14}$ and $R^{15}$ are independently selected from the group consisting of H, alkyl having from 1 to 10 carbons, heteroaryl having from 1 to 10 carbons, alkanoyl having from 1 to 10 carbons, and aroyl, wherein said alkyl, heteroaryl, alkanoyl and aroyl groups are optionally substituted with J;

J is selected from the group consisting of halogen, $C(=O)OR^{16}$, $R^{16}OC(=O)$, $R^{16}OC(=O)NH$, OH, CN, $NO_2$, $NR^{16}R^{17}$, $N=C(R^{16})R^{17}$, $N=C(NR^{16}R^{17})_2$, $SR^{16}$, $OR^{16}$, phenyl, napththyl, heteroaryl, and a cycloalkyl group having from 3 to 8 carbons;

$R^{16}$ and $R^{17}$ are independently H, alkyl having from 1 to 10 carbons, aryl, or heteroaryl, wherein said alkyl, aryl and heteroaryl groups are optionally substituted with K;

L is a phosphorus-containing enzyme reactive group, which preferably has the formula:

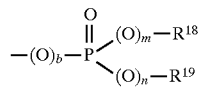

wherein:

m, n, and b are each independently 0 or 1;

$R^{18}$ and $R^{19}$ are each independently selected from the group consisting of H, lower alkyl optionally substituted with K, aryl optionally substituted with K, and heteroaryl optionally substituted with K;

or $R^{18}$ and $R^{19}$ taken together with $-(O)_m-P(=O)-(O)_n-$ can form a 5–8 membered ring containing up to 3 hetero atoms, or $R^{18}$ and $R^{19}$ taken together with $-(O)_m-P(=O)-(O)_n-$ can form a 5–8 membered ring optionally substituted with K.

In some preferred embodiments of the compounds of Formula I, $R^1$ is selected from the group consisting of benzyl, p-benzyloxybenzyl, $-(CH_2)_4-NHC(=O)-O-CH_2-C_6H_5$, $-(CH_2)_4-NHC(=O)-O-t-C_4H_9$, and $-(CH_2)_4-NHSO_2-C_6H_5$; $R_3$, $R_4$, and $R_5$ are each H; $W^1$ and $W^2$ together form $-C(=O)-$; Y is H or $CH_2F$; B is CO, O, S, $SO_2$ or a bond; $R^2$ is $-C(=O)CH_3$, and $-S(=O)_2R^6$ wherein $R^6$ is methyl, p-fluorophenyl, dimethylamino, ethyl, 2-thienyl, 2-isoxazolyl, phenyl, p-methylphenyl, 4-Nmethylimidazolyl, and 2-naphthyl; G is tetrahydroisoquinolinyl, benzyl, 3-indolyl, phenyl, N-methylbenzylamino, p-benzyloxyphenyl, 2-thienyl; or Q and $R^3$ together form $-(CH_2)_3-$.

In other preferred embodiments of Formula I, q is 0; B is a bond; G is benzyl or 2-thienyl; Y is H; $R^1$ is benzyl; and $R^2$ is $-S(=O)_2R^6$ wherein $R^6$ is methyl, phenyl, or 2-thienyl.

In further preferred embodmients of the compounds of Formula I, q is 1; G is tetrahydroisoquinolinyl, benzyl, 3-indolyl, phenyl, N-methylbenzylamino, or p-benzyloxyphenyl; and $R^2$ is $-C(=O)CH_3$, or $-S(=O)_2R^6$ wherein $R^6$ is methyl, p-fluorophenyl, dimethylamino, ethyl, 2-thienyl, 2-isoxazolyl, p-methyiphenyl, 4-N-methylimidazolyl, or 2-naphthyl.

In more preferred embodiments of the compounds of Formula I wherein q is 1, G is benzyl; and $R^2$ is $-C(=O)CH_3$, or $-S(=O)_2R^6$ wherein $R^6$ is methyl, p-fluorophenyl, dimethylamino, ethyl, 2-isoxazolyl, p-methylphenyl, 4-N-methylimidazolyl, or 2-naphthyl, with methyl being preferred.

In other preferred embodmients of the compounds of Formula I, q is 2; B is S; G is benzyl; Y is H; $R^1$ is benzyl; and $R^2$ is $-S(=O)_2CH_3$.

The term "P2" as used herein in connection with enzyme substrate nomenclature has the meaning described by Schechter et al., *Biochem. Biophys. Res. Comm.* 27: 157–162, 1967, the disclosure of which is hereby incorporated by reference in its entirety.

As used herein, the term "alkyl" includes straight-chain, branched and cyclic hydrocarbon groups such as, for example, ethyl, isopropyl and cyclopropyl groups. Preferred alkyl groups have 1 to about 10 carbon atoms. "Cycloalkyl" groups are cyclic alkyl groups. The term "alkylene" denotes divalent alkyl groups; i.e., methylene ($-CH_2-$), ethylene ($-CH_2CH_2-$), propylene ($-CH_2CH_2CH_2-$), etc. "Aryl" groups are aromatic cyclic compounds including but not limited to phenyl, tolyl, naphthyl, anthracyl, phenanthryl, pyrenyl, and xylyl. Preferred aryl groups include phenyl and naphthyl. The term "carbocyclic", as used herein, refers to cyclic groups in which the ring portion is composed solely of carbon atoms. The term "heterocyclic" refers to cyclic groups in which the ring portion includes at least one heteroatom such as O, N or S. In general, the term "hetero" when used as a prefix denoted the presence of one or more hetero atoms. Thus, "heterocycloalkyl" groups are heterocycles containing solely single bonds within their ring portions, i.e. saturated heteroatomic ring systems. The term "lower alkyl" refers to alkyl groups of 1–4 carbon atoms. The term "halogen" refers to F, Cl, Br, and I atoms. The term "aralkyl" denotes alkyl groups which bear aryl groups, for example, benzyl groups.

As used herein, "alkoxy" groups are alkyl groups linked through an oxygen atom. Examples of alkoxy groups include methoxy ($-OCH_3$) and ethoxy ($-OCH_2CH_3$) groups. In general, the term "oxy" when used as a suffix denotes attachment through an oxygen atom. Thus, alkoxycarbonyl groups are carbonyl groups which contain an alkoxy substituent, i.e., groups of general formula $-C(=O)-O-R$, where R is alkyl. The term "aralkyloxy" denotes an aralkyl group linked through an oxygen atom. The term "heteroaryl" denotes aryl groups having one or more heteroatoms contained within an aromatic ring. The term "heteroarylaklyl" denotes a heteroaryl group attached through an alkyl group. "Heteroaralkyl" groups are aralkyl groups which have one or more heteroatoms in their aromatic ring portion. The term "carbohydrate" includes monosaccharides, disaccharides, and polysaccharides, as well as their protected derivatives, such as, for example, mono- and diisopropylidine, and benzylidene derivatives.

As used herein the term "alkanoyl" denotes an alkyl group attached through a carbonyl group, i.e., $-C(=O)-R$ where R is alkyl. The term "aroyl" analogously denotes an aryl group attached through a carbonyl group. The term "sulfonyl" when used as a suffix denotes attachment through a $-SO_2-$ group. As used herein, the term group I counterion denotes $Li^+$, $Na^+$, $K^+$, $Rb^+$ and $Cs^+$.

As used herein, the term "amino acid" denotes a molecule containing both an amino group and a carboxyl group. As used herein the term "L-amino acid" denotes an α-amino acid having the L configuration around the α-carbon, that is, a carboxylic acid of general formula CH(COOH)(NH$_2$)—(side chain), having the L-configuration. The term "D-amino acid" similarly denotes a carboxylic acid of general formula CH(COOH)(NH$_2$)—(side chain), having the D-configuration around the α-carbon. Amino acid α-carbon atoms having the D-configuration are denoted herein by the symbol "C*". Side chains of L-amino acids include naturally occurring and non-naturally occurring moieties. Non-naturally occurring (i.e., unnatural) amino acid side chains are moieties that are used in place of naturally occurring amino acid side chains in, for example, amino acid analogs. See, for example, Lehninger, *Biochemistry*, Second Edition, Worth Publishers, Inc, 1975, pages 73–75. One representative amino acid side chain is the lysyl side chain, —(CH$_2$)$_4$—NH$_2$. Other representative α-amino acid side chains are shown below in Table 1.

In a research environment, preferred compounds having defined attributes can be used to screen for natural and synthetic compounds which evidence similar characteristics in inhibiting protease activity. The compounds can also be used in the refinement of in vitro and in vivo models for determining the effects of inhibition of particular proteases on particular cell types or biological conditions. In a therapeutic setting, given the connection between cysteine proteases and certain defined disorders, and serine proteases and certain defined disorders, compounds of the invention can be utilized to alleviate, mediate, reduce and/or prevent disorders which are associated with abnormal and/or aberrant activity of cysteine proteases and/or serine proteases.

In preferred embodiments, compositions are provided for inhibiting a serine protease or a cysteine protease comprising a compound of the invention. In other preferred embodiments, methods are provided for inhibiting serine proteases or cysteine proteases comprising contacting a

TABLE 1

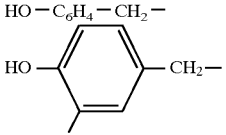
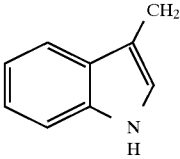
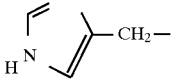
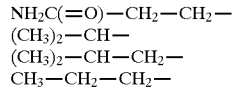
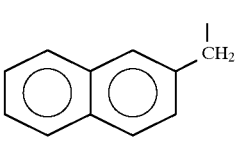

CH$_3$—
HO—CH$_2$—
CH$_6$H$_5$—CH$_2$—
HO—C$_6$H$_4$—CH$_2$—

HS—CH$_2$—
HO$_2$C—CH(NH$_2$)—CH$_2$—S—S—CH$_2$—
CH$_3$—CH$_2$—
CH$_3$—S—CH$_2$—CH$_2$—
CH$_3$—CH$_2$—S—CH$_2$—CH$_2$—
HO—CH$_2$—CH$_2$—
CH$_3$—CH(OH)—
HO$_2$C—CH$_2$—NHC(=O)—CH$_2$—

HO$_2$C—CH$_2$—CH$_2$—
NH$_2$C(=O)—CH$_2$—CH$_2$—
(CH$_3$)$_2$—CH—
(CH$_3$)$_2$—CH—CH$_2$—
CH$_3$—CH$_2$—CH$_2$—
H$_2$N—CH$_2$—CH$_2$—CH$_2$—
H$_2$N—C(=NH)—NH—CH$_2$—CH$_2$—CH$_2$—
H$_2$N—C(=O)—NH—CH$_2$—CH$_2$—CH$_2$—
CH$_3$—CH$_2$—CH(CH$_3$)—
CH$_3$—CH$_2$—CH$_2$—CH$_2$—
H$_2$N—CH$_2$—CH$_2$—CH$_2$—CH$_2$—

Functional groups present on the compounds of Formula I may contain protecting groups. For example, the amino acid sidechain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. One such protecting group is the benzyloxycarbonyl (Cbz; Z) group. Other preferred protecting groups according to the invention may be found in Greene, T. W. and Wuts, P. G. M., "*Protective Groups in Organic Synthesis*" 2d. Ed., Wiley & Sons, 1991.

Because the D-amino acid-containing compounds of the invention inhibit cysteine proteases and serine proteases, they can be used in both research and therapeutic settings.

protease selected from the group consisting of serine proteases and cysteine proteases with an inhibitory amount of a compound of the invention.

The disclosed compounds of the invention are useful for the inhibition of cysteine proteases and serine proteases. As used herein, the terms "inhibit" and "inhibition" mean having an adverse effect on enzymatic activity. An inhibitory amount is an amount of a compound of the invention effective to inhibit a cysteine and/or serine protease.

Pharmaceutically acceptable salts of the cysteine and serine protease inhibitors also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable organic amine addition salts are salts with morpholine and piperidine. Examples of pharmaceutically acceptable amino acid addition salts are salts with lysine, glycine, and phenylalanine.

Compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, transdermal patches; or prepared in other suitable fashions for these and other forms of administration as will be apparent to those skilled in the art.

The composition may conveniently be administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The materials for this invention can be employed as the sole active agent in a pharmaceutical or can be used in combination with other active ingredients which could facilitate inhibition of cysteine and serine proteases in diseases or disorders.

As used herein, the phrase "enantiomerically enriched amount" when used in connection with a compound of Formula I in compositions of the invention, denotes the predominance (i.e., greater than 50%) of the compound of Formula I wherein the carbon atom designated by C* in Formula I has the D-configuration over the corresponding L-isomer at this position. In preferred embodiments of the compositions of the invention, the enantiomerically enriched amount of the compound of Formula I is an amount greater than about 75% (i.e., the D-isomer compound of Formula I constitutes greater than about 75% of the combined amount of compound of Formula I and the corresponding L-isomer). In more preferred embodiments of the compositions of the invention, the enantiomerically enriched amount of the compound of Formula I is an amount greater than about 85%, more preferably greater than about 90%, still more preferably greater than about 95%, and most preferably about 100%.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in effective inhibitory amounts in an aqueous physiological buffer solution containing about 0.1 to 10% w/v compound for parenteral administration. Typical dose ranges are from about 1 µg/kg to about 1 g/kg of body weight per day; a preferred dose range is from about 0.01 mg/kg to 100 mg/kg of body weight per day. Such formulations typically provide inhibitory amounts of the compound of the invention. The preferred dosage of drug to be administered is likely, however, to depend on such variables as the type or extent of progression of the disease or disorder, the overall health status of the particular patient, the relative biological efficacy of the compound selected, and formulation of the compound excipient, and its route of administration.

As used herein, the term "contacting" means directly or indirectly causing at least two moieties to come into physical association with each other. Contacting thus includes physical acts such as placing a compound of the invention together with a protease in a container, or administering a compound of the invention to a patient. Thus, for example, administering a compound of the invention to a human patient evidencing a disease or disorder associated with abnormal and/or aberrant activity of such proteases falls within the scope of the definition of the term "contacting".

The invention is further illustrated by way of the following examples which are intended to elucidate the invention. These examples are not intended, nor are they to be construed, as limiting the scope of the disclosure.

EXAMPLES

Compounds of the invention were prepared by the following procedures. $R_f$ values are reported using standard silica gel and analytical plates.

The synthesis of compounds of Formulae 1–9 are summarized in Scheme I below:

SCHEME 1

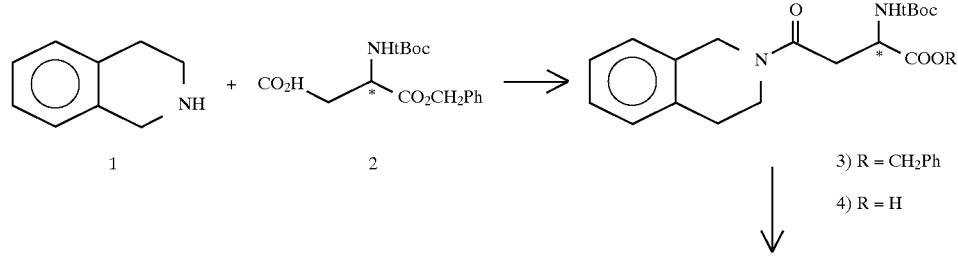

3) R = CH$_2$Ph
4) R = H

-continued
SCHEME 1

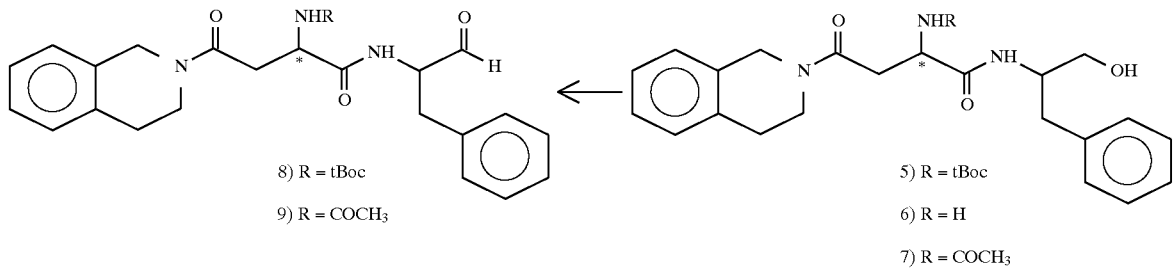

8) R = tBoc
9) R = COCH₃

5) R = tBoc
6) R = H
7) R = COCH₃

The symbol "*" denotes a D-configuration around the indicated carbon atom.

Examples 1–5 show the synthesis of intermediate compounds 3–7. Examples 6 and 7 show the preparation of compounds 8 and 9 of the invention.

Example 1

Synthesis of Compound 3

To a stirring mixture of Compound 1 (0.65 g, 2 mmol) and Compound 2 (purchased from Bachem Bioscience, Inc., King of Prussia, Pa.) (0.27 g, 2 mmol) in methylene chloride (5 mL), at room temperature, was added triethylamine (0.45 g, 4.4 mmol) followed by bis(2-oxo-3-oxazolidinyl) phosphinic chloride (BOP—Cl, 0.51 g, 2 mmol). The mixture was stirred for another 2 h, slowly poured into ice-water (10 mL) and extracted into ethyl acetate (3×10 mL). The combined organic layer was successively washed with 2% citric acid solution (2×5 mL), 2% $NaHCO_3$ solution (2×5 mL), $H_2O$ (1×5 mL), brine (1×5 mL), dried over $Na_2SO_4$ and concentrated to give a crude product. Purification by flash column chromatography (silica gel, 30% ethyl acetate in hexane) yielded 0.64 g of Compound 3.

3: White gum; $R_f$ (50% ethyl acetate in hexane):0.60; $^1$H-NMR (300 MHz, $CDCl_3$) δ 7.40–7.05 (m, 9H), 5.90 (d, 1H), 5.25–5.10 (m, 2H), 4.70–4.55 (m, 3H), 3.80–3.55 (2 sets of t, 2H), 3.30–3.15 (m, 1H), 2.95–2.80 (m, 3H), 1.40 (s, 9H).

Example 2

Synthesis of Compound 4

A mixture of Compound 3 (0.61 g, 1.40 mmol) and 0.20 g of 10% Pd-C (DeGussa type, 50% $H_2O$ content) in methanol (40 mL) was hydrogenated (40 psi) in a Parr apparatus for 1 hour. Filtration through a Celites® pad and solvent evaporation gave 0.47 g of Compound 4 which was used without further purification. $^1$H-NMR spectrum of Compound 4 showed the absence of peaks for a benzyl group.

Example 3

Synthesis of Compound 5

To a cooled (0° C.) solution of Compound 4 (0.20 g, 0.574 mmol) in anhydrous DMF (4 mL) was added N-methylmorpholine (0.174 g, 1.722 mmol) followed by 1-HOBt (0.080 g, 0.574 mmol) and BOP (0.254 g, 0.574 mmol). The mixture was stirred for 15 minutes and to it was added (s)-phenylalaninol (0.112 g, 0.7463 mmol). The cooling bath was removed and the mixture was stirred for another 2 h, poured into water (5 mL) and extracted into ethyl acetate (3×10 mL). The combined organic layer was successively washed with 2% citric acid solution (2×5 mL), 2% $NaHCO_3$ solution (2×5 mL), $H_2O$ (1×5 mL), brine (1×5 mL), dried over $Na_2SO_4$ and concentrated to give a crude product. Purification by flash column chromatography (silica gel, 5% methanol in methylene chloride) yielded 0.212 g of Compound 5.

5: White solid, mp 63°–72° C.(softening to melt); $R_f$ (5% methanol in methylene chloride):0.47; $^1$H-NMR (300 MHz, $CDCl_3$) δ 7.30–7.00 (m, 9H), 6.80 (broad, 1H), 5.90 (d, 1H), 4.80–4.45 (m, 4H), 4.30–4.10 (broad, 1H), 3.85–3.30 (m, 6H), 2.95–2.40 (m, 4H), 1.45 (s, 9H).

Example 4

Synthesis of Compound 6

A mixture of Compound 5 (0.190 g, 0.3945 mmol) and 90% TFA (1.2 mL) in methylene chloride (3 mL) was stirred at room temperature for 1 hour. Excess TFA was removed and the residue was diluted with methylene chloride (5 mL) and washed with 2% $NaHCO_3$ solution (2×4 mL), brine (1×5 mL), dried over $Na_2SO_4$ and concentrated to give 0.15 g of Compound 6 which was used without further purification. $^1$H-NMR (300 MHz, $CDCl_3$) spectrum of an aliquot showed no peak at δ 1.45 for a t-boc group.

Example 5

Synthesis of Compound 7

To a cooled (0° C.) solution of Compound 6 (0.150 g, 0.3944 mmol) in anhydrous methylene chloride (4 mL) was added triethylamine (0.040 g, 0.3944 mmol). A solution of acetyl chloride (0.030 g, 0.3944 mmol) in methylene chloride (1 mL) was added dropwise into the reaction flask over a period of 5 minutes. The cooling bath was removed and the reaction mixture was stirred for an additional 30 minutes, poured into ice-water (5 mL) and the layers were separated. The organic layer was washed with 3% hydrochloric acid solution (2×4 mL), saturated sodium bicarbonate solution (1×5 mL), brine (1×5 mL) and dried over anhydrous sodium sulfate. Solvent evaporation gave a crude product which was purified by flash column chromatography (silica gel, 3% methanol in methylene chloride) to yield 0.025 g of Compound 7.

7: White solid, mp 64°–79° C. (softening to melt); $R_f$(5% methanol in methylene chloride):0.34; $^1$H-NMR (300 MHz, $CDCl_3$) δ 7.30–7.00 (m, 10H), 4.95–4.80 (m, 1H), 4.75–4.40 (m,2H), 4.30–4.15 (m, 1H) 3.90–3.50 (m, 4H), 3.25–3.10 (m, 2H), 3.00–2.80 (m, 4H), 2.45–2.30 (m, 1H), 2.05 (m, 1H), 2.00 (d, 3H).

Example 6

Synthesis of Compound 8

To a cooled (0° C.) solution of Compound 5 (0.100 g, 0.21 mmol) in anhydrous methylene chloride (2 mL) and anhydrous dimethyl sulfoxide (2 mL) was added triethylamine (0.085 g, 0.839 mmol). Sulfur trioxide-pyridine complex (0.133 g, 0.839 mmol) was slowly added to the stirred mixture over a period of 5 minutes and the ice-bath was removed. The mixture was stirred for another 1 h, poured into water (10 mL) and extracted into ethyl acetate (3×10 mL). The organic layer was washed with 2% citric acid solution (2×5 mL), saturated sodium bicarbonate solution (2×5 mL), brine (1×5 mL) and dried over anhydrous magnesium sulfate. Solvent evaporation gave a residue which was washed with n-pentane (20 mL) and dried under vacuum to produce 0.055 g of Compound 8 of the invention. A general description of this preparative procedure can be found in Luly, J. R. et al., *J. Org. Chem.* 1987, 1487–1492.

8: White solid, mp 70°–80° C. (softening to melt); $R_f$(ethyl acetate):0.69; $^1$H-NMR (300 MHz, CDCl$_3$) δ 9.55 (d, 1H), 7.50 (broad, 1H), 7.25–7.00 (m, 9H), 6.05 (d, 1H), 4.75–4.45 (m, 4H), 3.85–3.00 (m, 5H), 2.95–2.40 (m, 3H), 1.45 (s, 9H).

Example 7

Synthesis of Compound 9

This compound was synthesized following the general procedure described for the synthesis of Compound 8. Thus the oxidation of 0.110 g of Compound 7 by 0.145 g of sulfur trioxide-pyridine complex in presence of 0.092 g of triethylamine generated 0.060 g of Compound 9 of the invention.

9: White solid, mp 80°–120° C. (softening to melt); $R_f$ (5% methanol in methylene chloride): 0.31; $^1$H-NMR (300 MHz, CDCl$_3$) δ 9.60 (d, 1H), 7.70–7.60 (t, 1H), 7.30–7.00 (m, 9H), 4.95–4.85 (m, 1H), 4.80–4.40 (m, 3H), 3.90–2.80 (m, 8H), 2.40–2.30 (m, 1H), 2.00 (s, 3H).

Scheme 2 Shows the synthesis of compounds 10–14:

deesterification of 2.10 g of Compound 3 by 90% TFA (3 mL) in methylene chloride (7 mL) gave Compound 10 (1.47 g) which was used without further purification. $^1$H-NMR (300 MHz, CDCl$_3$) spectrum of an aliquot showed no peak at δ 1.40 for a t-boc group.

Example 9

Synthesis of Compound 11

To a cooled (0° C.) solution of Compound 10 (1.393 g, 4.1172 mmol) in methylene chloride (15 mL) was added triethylamine (0.445 g, 4.3976 mmol). A solution of methanesulfonyl chloride (0.504 g, 4.3998 mmol) in methylene chloride (4 mL) was added dropwise into the reaction flask over a period of 5 minutes. The cooling bath was removed and the reaction mixture was stirred for an additional 30 minutes, poured into ice-water (20 mL) and the layers were separated. The organic layer was washed with 2% citric acid solution (2×10 mL), saturated sodium bicarbonate solution (2×10 mL), brine (1×10 mL) and dried over anhydrous sodium sulfate. Solvent evaporation gave a crude product which was purified by flash column chromatography (silica gel, 3% methanol in methylene chloride) to yield 0.720 g of Compound 11.

11: White solid, mp 55°–85° C. (softening to melt); $R_f$ (5% methanol in methylene chloride): 0.71; $^1$H-NMR (300 MHz, CDCl$_3$) δ 7.40–7.00 (m, 9H), 5.85 (dd, 1H), 5.25–5.05 (2 sets of t, 2H), 4.65 (q, 1H), 4.50 (s, 1H), 4.40 (m, 1H), 3.85 (m, 1H), 3.60 (m, 1H), 3.30 (m, 1H), 3.00 (s, 3H), 3.00–2.80 (m, 3H).

Example 10

Synthesis of Compound 12

This compound was synthesized following the general procedure described for the synthesis of Compound 4. Thus

SCHEME 2

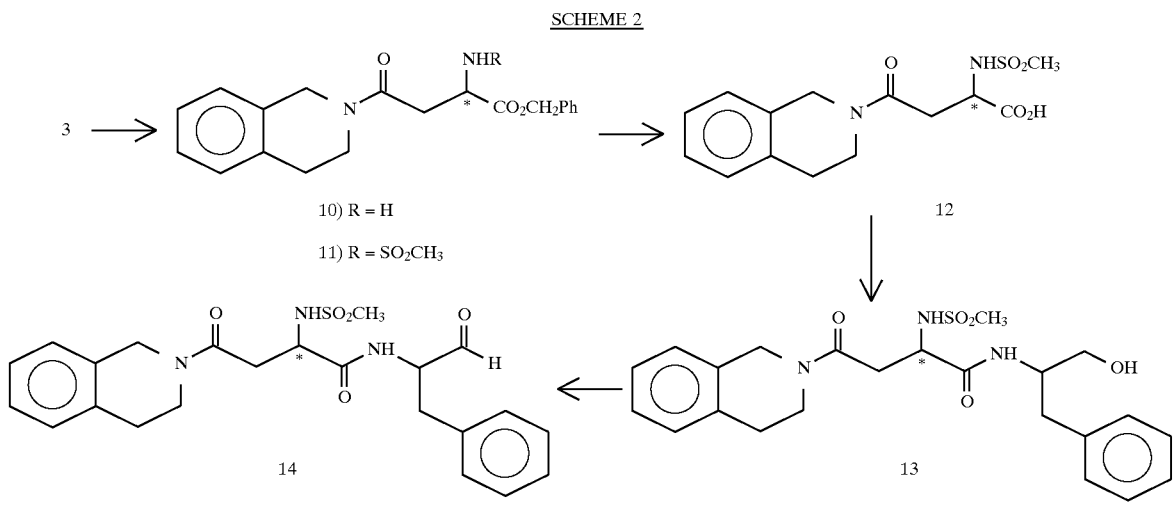

The symbol "*" denotes a D-configuration around the indicated carbon atom.

Examples 8–11 show the synthesis of intermediate compounds 10–13. Example 12 shows the preparation of compound 14 of the invention.

Example 8

Synthesis of Compound 10

This compound was synthesized following the general procedure described for the synthesis of Compound 6. Thus 0.69 g of Compound 11 was hydrogenated to 0.50 g of Compound 12 in a Parr apparatus, and the product was used without further purification. $^1$H-NMR spectrum of an aliquot showed no peaks for a benzyl group.

Example 11

Synthesis of Compound 13

This compound was synthesized following the general procedure described for the synthesis of Compound 5. Thus the reaction between 0.204 g of Compound 12 and 0.113 g of (S)-phenylalaninol generated a crude product which was purified by flash column chromatography (silica gel, 3% methanol in methylene chloride) to yield 0.192 g of Compound 13.

13: White solid, mp 55°–85° C.(softening to melt); $R_f$ (5% methanol in methylene chloride): 0.34; $^1$H-NMR (300 MHz, CDCl$_3$) δ 7.35–7.00 (m, 10H), 6.00 (broad, 1H), 4.75–4.40 (2 sets of q, 2H), 4.30 (m, 2H), 3.85–3.45 (m, 4H), 3.35–3.25 (m, 1H), 3.05–2.60 (m, 6H), 2.85 (s, 3H).

Example 12

Synthesis of Compound 14

This compound was synthesized following the general procedure described for the synthesis of Compound 8. Thus the oxidation of 0.110 g of Compound 13 by 0.133 g of sulfur trioxide-pyridine complex in presence of 0.085 g of triethylamine generated 0.080 g of Compound 14 of the invention.

14: White solid, mp 80°–110° C. (softening to melt); $R_f$ (5% methanol in methylene chloride): 0.36; $^1$H-NMR (300 MHz, CDCl$_3$) δ 9.60 (s, 1H), 7.80 (d, 1H), 7.35–7.00 (m 9H), 6.10 (d, 1H), 4.80 (m, 2H), 4.50 (m, 1H), 4.35 (m, 1H), 3.85–3.45 (m, 3H), 3.30–3.20 (m, 2H), 3.05–2.60 (m, 3H), 2.85 (s, 3H).

Scheme 3 shows the synthesis of compounds 16, 17a–b and 18a–b:

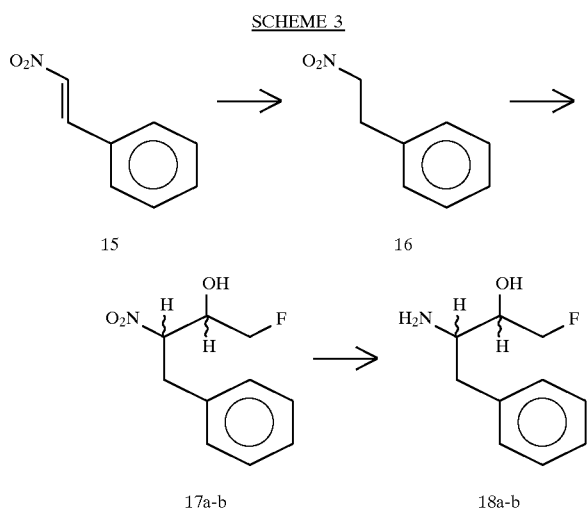

SCHEME 3

Examples 13 and 14 show the synthesis of intermediate compounds 16 and 17a–b. Example 15 shows the preparation of intermediate compounds 18a–b.

Example 13

Synthesis of Compound 16

To a stirring mixture of trans-β-nitrostyrene (Compound 15, 5.25 g, 0.035 mol) and silica gel (10 g, 230–400 mesh) in chloroform (400 mL) and isopropanol (75 mL) at room temperature, was slowly added sodium borohydride (5.50 g, 0.145 mol) over a period of 45 minutes. The reaction mixture was stirred for an additional 15 minutes and then carefully quenched with 10% hydrochloric acid (20 mL). Separated solid was filtered and washed with chloroform (50 mL). The combined filtrate and washings were washed with water (1×20 mL), brine (1×20 mL) and dried over anhydrous sodium sulfate. Solvent evaporation at reduced pressure gave a crude material which was purified by flash chromatography (silica gel, 8% ethyl acetate-hexane) to give 2.86 g of Compound 16.

16: Colorless oil (spicy odor); $R_f$ (10% ethyl acetate in hexane) : 0.40; $^1$H-NMR (300 MHz, CDCl$_3$) δ 7.40–7.20 (m, 5H), 4.60 (t, 2H), 3.30 (t, 2H).

Example 14

Synthesis of Compounds 17a–b

To a cooled (−78° C.) solution of oxalyl chloride (2M) in methylene chloride (11.60 mL, 0.0232 mol) was added slowly dimethyl sulfoxide (3.65 g, 3.32 mL, 0.0467 mol). The reaction mixture was stirred for 15 minutes. A solution of 2-fluoroethanol (1.16 g, 0.0181 mol) in methylene chloride (10 mL) was then slowly introduced into the reaction flask. After stirring for another 15 minutes, the reaction mixture was diluted with anhydrous methylene chloride (180 mL), and triethylamine (9.20 g, 12.63 mL, 0.090 mol) was added. Stirring was continued for another 2 h at which time the reaction mixture had warmed to room temperature. At this time, a solution of Compound 16 (2.74 g, 0.0181 mol) in anhydrous methylene chloride (10 mL) was added to the reaction mixture and stirring was continued overnight. The mixture was then washed with water (1×30 mL), 4% hydrochloric acid (3×20 mL), water (1×20 mL), saturated sodium bicarbonate solution (2×20 mL) and brine (1×20 mL). Drying over anhydrous sodium sulfate and solvent evaporation gave a crude material which was purified by flash chromatography (silica gel, 25% ethyl acetate-hexane) to give Compounds 17a and 17b as erythro/threo isomers. Combined yield was 3.01 g. In another set of experiments, 13.94 g of Compound 16 was converted to 12.5 g of Compounds 17a–b which, without any separation, were used in the subsequent steps. A general description of this preparative procedure can be found in Imperiali, B. et al., Tetrahedron Lett. 27(2), 135, 1986 and in Revesz, L. et al., Tetrahedron Lett. 35(52), 9693, 1994.

17a: White solid, mp 71°–73° C.; $R_f$ (30% ethyl acetate in hexane): 0.46; $^1$H-NMR (300 MHz, CDCl$_3$) δ 7.40–7.10 (m, 5H), 4.90 (m, 1H), 4.60 (m, 1H), 4.50–4.30 (m, 2H), 3.45–3.25 (m, 2H), 2.70 (d, 1H).

17b: Colorless oil; $R_f$ (30% ethyl acetate in hexane) 0.42; $^1$H-NMR (300 MHz, CDCl$_3$) δ 7.40–7.15 (m, 5H), 4.90 (m, 1H), 4.65 (m,1H), 4.50 (m, 1H), 4.20 (m, 1H), 3.40–3.30 (m, 2H), 2.90 (d,1H).

Example 15

Synthesis of Compounds 18a–b

A mixture of Compound 17a (0.48 g, 2.25 mmol), absolute ethanol (20 mL) and Raney-Nickel (catalytic) was hydrogenated (60 psi) in a Parr apparatus for 5 hours. Filtration through a Celite® pad and solvent evaporation gave 0.41 g of Compound 18a. Similar treatment of Compound 17b (0.80 g, 3.75 mmol) gave 0.51 g of Compound 18b. Finally, a combined mixture of Compounds 17a–b (10.00 g) was hydrogenated to give 7.20 g of a mixture of Compounds 18a–b which was used in all the experiments, described below.

18a: White solid, mp 64°–67° C.; $^1$H-NMR (300 MHz, CDCl$_3$) δ 7.40–7.10 (m, 5H), 4.70 (d, 1H), 4.50 (d, 1H), 3.90–3.70 (m, 1H), 3.30–3.10 (m, 1H), 2.95 (dd, 1H), 2.60–2.45 (q, 1H), 2.20–1.70 (broad, 3H).

18b: White solid, mp 67°–70° C.; $^1$H-NMR (300 MHz, CDCl$_3$) δ 7.40–7.10 (m, 5H), 4.70 (d, 1H), 4.55 (d, 1H), 3.70–3.50 (m, 1H), 3.20–3.00 (m, 1H), 2.95 (dd, 1H), 2.60–2.45 (q, 1H), 2.20–1.65 (broad, 3H).

Scheme 4 shows the synthesis of compounds 19 and 20:

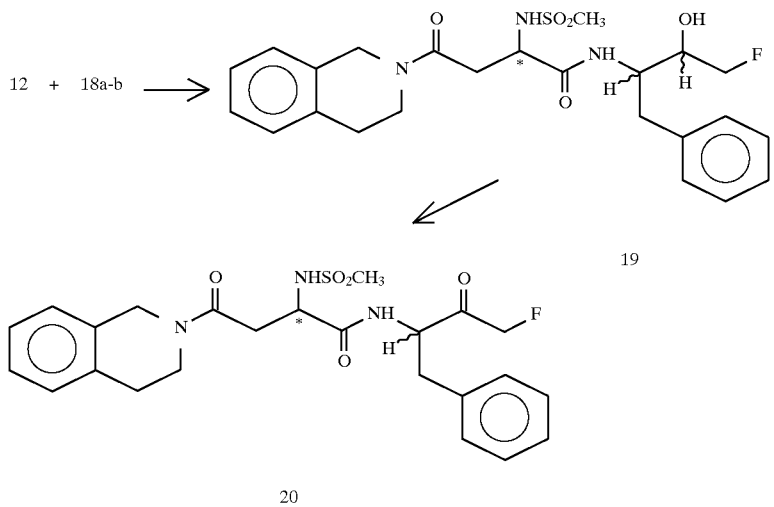

The symbol "*" denotes a D-configuration around the indicated carbon atom.

Example 16 shows the synthesis of intermediate compound 19. Example 17 shows the preparation of compound 20 of the invention.

Example 16

Synthesis of Compound 19

This compound was synthesized following the general procedure described for the synthesis of Compound 5. Thus the reaction between 0.142 g of Compound 12 and 0.088 g of Compounds 18a–b generated a crude product which was purified by flash column chromatography (silica gel, 3% methanol in methylene chloride) to yield 0.138 g of Compound 19 as a mixture of diastereoisomers.

19: White solid, mp 75°–115° C. (softening to melt); $R_f$ (5% methanol in methylene chloride): 0.44; $^1$H-NMR (300 MHz, CDCl$_3$) δ 7.50–7.05 (m, 10H), 6.15–5.75 (m, 1H), 4.70–3.40 (m, 11H), 3.30–2.50 (m, 8H).

Example 17

Synthesis of Compound 20

To a cooled (0° C.) solution of Compound 19 (0.126 g, 0.2563 mmol) in anhydrous methylene chloride (8 mL) was added Dess-Martin periodinane reagent (0.217 g, 0.5126 mmol). The cooling bath was removed and the mixture was stirred for an additional 45 minutes. It was then diluted with methylene chloride (15 mL) and washed with 10% sodium thiosulfate solution (4×10 mL), saturated sodium bicarbonate solution (1×10 mL) and brine (1×10 mL). Drying over anhydrous sodium sulfate and solvent removal under reduced pressure gave a crude material which was purified by flash column chromatography (silica, 70% ethyl acetate-hexane) to generate 0.094 g of Compound 20 of the invention as a mixture of two diastereoisomers. A general description of this preparative procedure can be found in Patel, D. V. et al, *J. Med. Chem.* 1993, 36, 2431–2447.

20: White solid; $R_f$ (70% ethyl acetate in hexane): 0.44; $^1$H-NMR (300 MHz, CDCl$_3$) δ 7.80–7.65 (m, 1H), 7.40–7.05 (m, 9H), 6.10–6.00 (t, 1H), 5.10–4.40 (m, 6H), 4.35–4.25 (m, 1H), 3.90–3.50 (m, 2H), 3.30–2.50 (m, 5H), 2.85 (m, 3H).

Scheme 5 shows the synthesis of compounds 22–25:

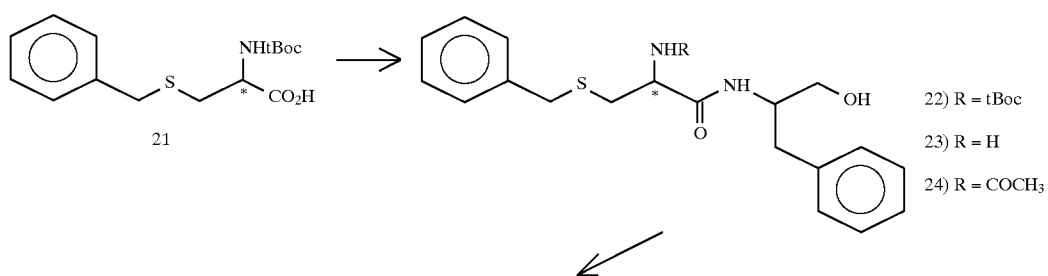

-continued
SCHEME 5

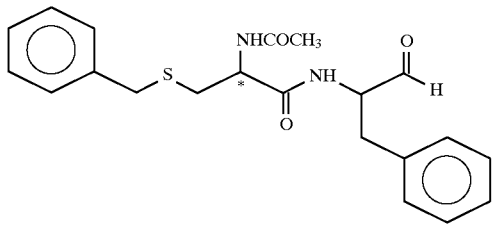

25

The symbol "*" denotes a D-configuration around the indicated carbon atom.

Examples 18–20 show the synthesis of intermediate compounds 22–24. Example 21 shows the preparation of compound 25 of the invention.

Example 18

Synthesis of Compound 22

This compound was synthesized following the general procedure described for the synthesis of Compound 5. Thus the reaction between 1.095 g of Compound 21 (purchased from Advanced ChemTech, Louisville, Ky.) and 0.532 g of (s)-phenylalaninol generated a crude product which was purified by flash column chromatography (silica gel, 3% methanol in methylene chloride) to yield 1.06 g of Compound 22.

22: White solid, mp 105°–108° C.; $R_f$ (5% methanol in methylene chloride): 0.44; $^1$H-NMR (300 MHz, CDCl$_3$) δ 7.40–7.15 (m, 10H), 6.40 (d, 1H), 5.10 (broad, 1H), 4.25–4.05 (m, 2H), 3.75 (s, 2H), 3.70–3.50 (2 sets of m, 2H), 2.95–2.55 (m, 5H). 1.45 (s, 9H).

Example 19

Synthesis of Compound 23

This compound was synthesized following the general procedure described for the synthesis of Compound 6. Thus the reaction between 0.512 g of Compound 21 and 1 mL of 90% TFA in 3 mL methylene chloride generated 0.38 g of Compound 23 which was used without further purification. $^1$H-NMR (300 MHz, CDCl$_3$) spectrum of an aliquot showed no peak at δ 1.45 for a t-boc group.

Example 20

Synthesis of Compound 24

This compound was synthesized following the general procedure (except that acetyl bromide was used in place of acetyl chloride) described for the synthesis of Compound 7. Thus the reaction between 0.377 g of Compound 23 and 0.121 g of acetyl bromide in the presence of 0.10 g of triethylamine in 5 mL methylene chloride gave a crude product which was purified by flash column chromatography (silica gel, 4% methanol in methylene chloride) to yield 0.158 g of Compound 24.

24: White solid, mp 149°–151° C.; $R_f$ (5% methanol in methylene chloride): 0.32; $^1$H-NMR (300 MHz, CDCl$_3$) δ 7.40–7.05 (m, 10H), 6.80 (d, 1H), 6.45 (d, 1H), 4.45 (q, 1H), 4.20 (m, 1H), 3.70 (s, 2H), 3.75–3.50 (2 sets of m, 2H), 3.20–3.00 (m, 1H), 2.90–2.75 (m, 2H), 2.70–2.50 (2 sets of q, 2H), 1.95 (s, 3H).

Example 21

Synthesis of Compound 25

This compound was synthesized following the general procedure described for the synthesis of Compound 8. Thus the oxidation of 0.167 g of Compound 24 by 0.240 g of sulfur trioxide-pyridine complex in the presence of 0.153 g of triethylamine generated 0.085 g of Compound 25 of the invention.

25: White solid, mp 45°–70° C. (softening to melt); $R_f$ (ethyl acetate): 0.34; $^1$H-NMR (300 MHz, CDCl$_3$) δ 9.60 (s, 1H), 7.40–7.05 (m, 10H), 6.80 (d, 1H), 6.20 (d, 1H), 4.70–4.40 (2 sets of q, 2H), 3.70 (s, 2H), 3.10 (d, 1H), 2.90–2.50 (2 sets of m, 2H), 1.95 (s, 3H).

Scheme 6 shows the synthesis of compounds 27–34:

SCHEME 6

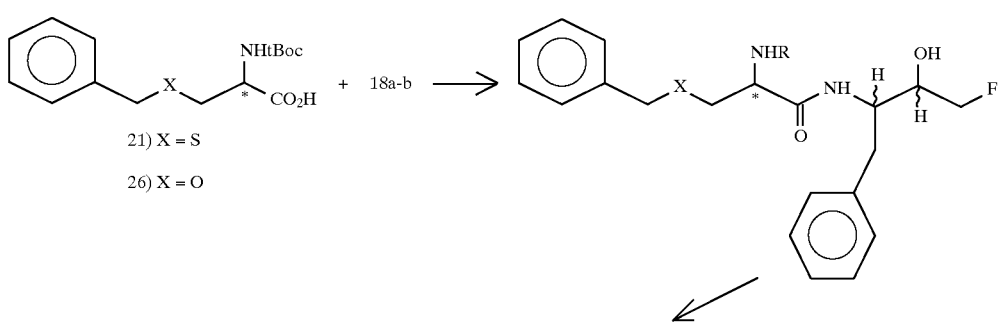

21) X = S
26) X = O

-continued
SCHEME 6

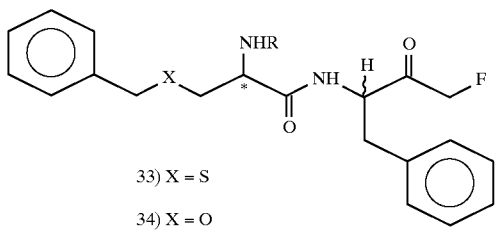

33) X = S
34) X = O

27) X = S, R = tBoc
28) X = S, R = H
29) X = S, R = SO$_2$CH$_3$
30) X = O, R = tBoc
31) X = O, R = H
32) X = O, R = SO$_2$CH$_3$

The symbol "*" denotes a D-configuration around the indicated carbon atom.

Examples 22–27 show the synthesis of intermediate compounds 27–32. Examples 28 and 29 show the preparation of compounds 33 and 34 of the invention.

Example 22

Synthesis of Compound 27

This compound was synthesized following the general procedure described for the synthesis of Compound 5. Thus the reaction between 1.033 g of Compound 21 and 0.668 g of Compound 18a–b generated a crude product which was purified by flash column chromatography (silica gel, 3% methanol in methylene chloride) to yield 1.38 g of Compound 27 as a mixture of diastereoisomers.

27: White solid, mp 120°–138° C. (softening to melt); R$_f$ (5% methanol in methylene chloride): 0.72 and 0.61 (overlapping 2 sets of erythro and threo isomers); $^1$H-NMR (300 MHz, CDCl$_3$) δ 7.40–7.15 (m, 10H), 6.60–6.30 (2 sets of t, 1H), 5.20–5.05 (broad, 1H), 4.60–3.90 (5 sets of m, 5H), 3.75–3.60 (2 sets of d, 2H), 3.00–2.80 (m, 3H), 2.75–2.55 (m, 2H), 1.50–1.30 (m, 9H).

Example 23

Synthesis of Compound 28

This compound was synthesized following the general procedure described for the synthesis of Compound 6. Thus the reaction between 1.02 g of Compound 27 and 3 mL of 90% TFA in 5 mL methylene chloride generated 0.77 g of Compound 28 which was used without further purification. $^1$H-NMR (300 MHz, CDCl$_3$) spectrum of an aliquot showed no peaks for a t-boc group at δ 1.50–1.30.

Example 24

Synthesis of Compound 29

This compound was synthesized following the general procedure described for the synthesis of Compound 11. Thus the reaction between 0.644 g of Compound 28 and 0.183 g of methanesulfonyl chloride in the presence of 0.162 g of triethylamine in 5 mL methylene chloride generated a crude product which was purified by flash column chromatography (silica gel, 50% ethyl acetate in hexane ) to yield 0.347 g of Compound 29 as a mixture of diastereoisomers.

29: White solid, mp 135°–150° C. (softening to melt); R$_f$ (5% methanol in methylene chloride): 0.63 and 0.59 (2 sets of overlapping erythro and threo isomers); $^1$H-NMR (300 MHz, CDCl$_3$) δ 7.40–7.10 (m, 10H), 6.70–6.30 (2 sets of m, 1H), 5.40–5.00 (2 sets of m, 1H), 4.70–4.10 (m, 4H), 4.00–3.85 (m, 1H), 3.80–3.60 (m, 2H), 3.10–2.50 (m, 8H).

Example 25

Synthesis of Compound 30

This compound was synthesized following the general procedure described for the synthesis of Compound 5. Thus the reaction between 0.633 g of Compound 26 (purchased from Advanced ChemTech, Louisville, Ky.) and 0.432 g of Compound 18a–b generated a crude product which was purified by flash column chromatography (silica gel, 3% methanol in methylene chloride) to yield 0.865 g of Compound 30 as a mixture of diastereoisomers.

30: White semi-solid; R$_f$ (5% methanol in methylene chloride): 0.72 and 0.65 (overlapping 2 sets of erythro and threo isomers); $^1$H-NMR (300 MHz, CDCl$_3$) δ 7.40–7.05 (m, 10H), 6.85–6.50 (1 set of d and 1 set of t, 1H), 5.40–5.20 (broad, 1H), 4.60–4.30 (m, 4H), 4.30–4.05 (m, 2H), 3.95–3.70 (m, 2H), 3.60–3.40 (m, 2H), 3.05–2.85 (m, 2H), 1.40 (2s, 9H).

Example 26

Synthesis of Compound 31

This compound was synthesized following the general procedure described for the synthesis of Compound 6. Thus the reaction between 0.820 g of Compound 30 and 2 mL of 90% TFA in 4 mL methylene chloride generated 0.506 g of Compound 31 which was used without further purification. $^1$H-NMR (300 MHz, CDCl$_3$) spectrum of an aliquot showed no peak at δ 1.40 for a t-boc group.

Example 27

Synthesis of Compound 32

This compound was synthesized following the general procedure described for the synthesis of Compound 11. Thus the reaction between 0.50 g of Compound 31 and 0.175 g of methanesulfonyl chloride in the presence of 0.155 g of triethylamine in 6 mL methylene chloride generated a crude product which was purified by flash column chromatography (silica gel, 4% methanol in methylene chloride ) to yield 0.32 g of Compound 32 as a mixture of diastereoisomers.

32: White solid, mp 118°–121° C.; R$_f$ (5% methanol in methylene chloride): 0.43; $^1$H-NMR (300 MHz, CDCl$_3$) δ 7.40–7.10 (m, 10H), 7.10–6.90 (2 sets of d, 1H), 5.40 (broad t, 1H), 4.60–4.10 (m, 5H), 4.05–3.80 (m, 2H), 3.80–3.50 (2 sets of m, 2H), 3.30–3.20 (m, 1H), 3.00–2.60 (m, 5H).

Example 28

Synthesis of Compound 33

This compound was synthesized following the general procedure described for the synthesis of Compound 20. Thus the oxidation of 0.296 g of Compound 29 by 0.276 g of Dess-Martin reagent in 10 mL methylene chloride generated a crude product which was purified by flash column chromatography (silica gel, 50% ethyl acetate in hexane ) to yield 0.15 g of Compound 33 of the invention as a mixture of diastereoisomers.

33: White solid, mp 40°–70° C.(softening to melt); $R_f$ (70% ethyl acetate in hexane): 0.75; $^1$H-NMR (300 MHz, CDCl$_3$) δ 7.40–7.10 (m, 10H), 6.85 (t, 1H), 5.25–4.75 (m, 4H), 3.90–3.75 (m, 1H), 3.70 (s, 2H), 3.30–3.10 (m, 1H), 3.05–2.90 (m, 1H), 2.85–2.60 (m, 5H).

Example 29

Synthesis of Compound 34

This compound was synthesized following the general procedure described for the synthesis of Compound 20. Thus the oxidation of 0.30 g of Compound 32 by 0.725 g of Dess-Martin reagent in 10 mL methylene chloride generated 0.25 g of Compound 34 of the invention as a mixture of two diastereoisomers.

34: White gum; $R_f$ (50% ethyl acetate in hexane): 0.38; $^1$H-NMR (300 MHz, CDCl$_3$) δ 7.40–7.00 (m, 11H), 5.40 (m, 1H), 5.10–470 (m, 3H), 4.60–4.40 (t, 2H), 4.05 (m, 1H), 3.80 (m, 1H), 3.60 (m, 1H), 3.20 (m, 1H), 2.90 (m, 1H), 2.80 (s, 3H). Scheme 7 shows the synthesis of compounds 36–40:

36: White solid, mp 80°–83 ° C.; $R_f$ (30% ethyl acetate in hexane): 0.37; $^1$H-NMR (300 MHz, CDCl$_3$) δ 7.40–7.00 (m, 10H), 6.90 (broad d, 1H), 5.40 (broad, 1H), 4.90 (q, 1H), 4.50 (q, 2H), 4.30 (broad, 1H), 3.90 (broad q, 1H), 3.70 (s, 3H), 3.50 (dd, 1H), 3.10 (m, 2H), 1.40 (s, 9H).

Example 31

Synthesis of Compound 37

This compound was synthesized following the general procedure described for the synthesis of Compound 6. Thus the reaction between 7.70 g of Compound 36 and 10 mL of 90% TFA in 15 mL of methylene chloride generated 6.00 g of Compound 37 which was used without further purification. $^1$H-NMR (300 MHz, CDCl$_3$) spectrum of an aliquot showed no peak at δ 1.40 for t-boc group.

Example 32

Synthesis of Compound 38

This compound was synthesized following the general procedure described for the synthesis of Compound 11. Thus

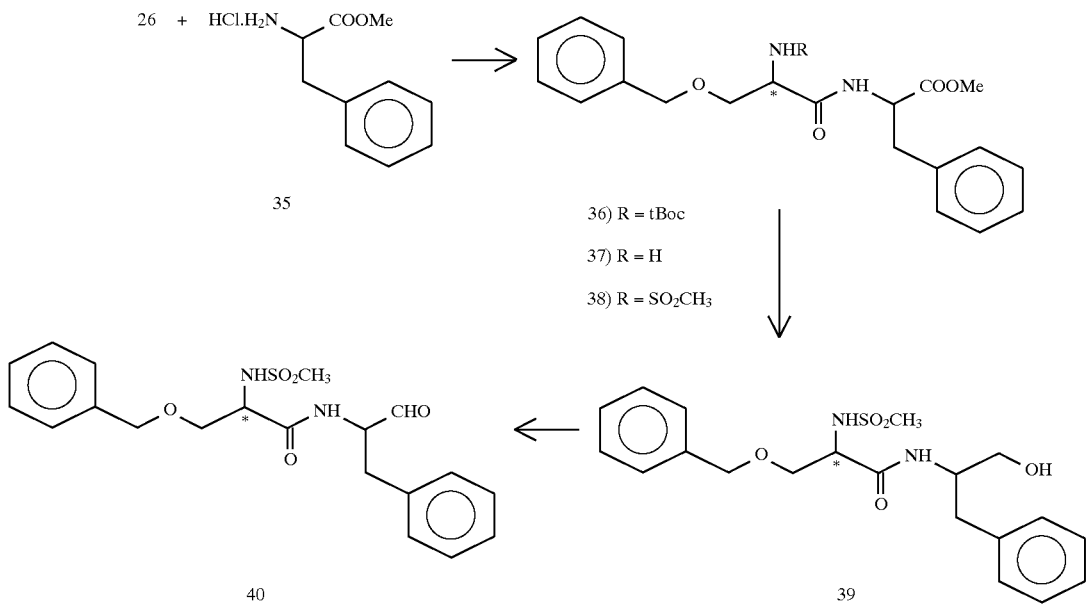

The symbol "*" denotes a D-configuration around the indicated carbon atom.

Examples 30–33 show the synthesis of intermediate compounds 36–39.
Example 34 shows the preparation of compound 40 of the invention.

Example 30

Synthesis of Compound 36

This compound was synthesized following the general procedure described for the synthesis of Compound 5. Thus the reaction between 5.221 g of Compound 26 and 4.20 g of Compound 35 generated 7.80 g of Compound 36, most of which was used in the next step without further purification. An aliquot of the crude product was purified by flash column chromatography (silica gel, 40% ethyl acetate in hexane) to yield an analytical sample.

the reaction between 6.00 g of Compound 37 and 2.70 g of methanesulfonyl chloride in the presence of 2.386 g of N-methylmorpholine (instead of triethylamine) in 20 mL methylene chloride generated a crude product which was purified by flash column chromatography (silica gel, 45% ethyl acetate in methylene chloride) to yield 5.86 g of Compound 38.

38: White solid, mp 92°–98° C. (softening to melt); $R_f$ (50% ethyl acetate in hexane): 0.33; $^1$H-NMR (300 MHz, CDCl$_3$) δ 7.40–7.00 (m, 11H), 5.30 (d, 1H), 4.85 (m 1H), 4.45 (q, 2H), 4.10 (q, 1H), 3.80 (dd,1H), 3.75 (s, 3H), 3.60 (dd, 1H), 3.20–3.00 (2 sets of q, 2H), 2.85 (s, 3H).

Example 33

Synthesis of Compound 39

To a stirred solution of Compound 38 (2.501 g, 5.7569 mmol) in anhydrous THF (10 mL) at room temperature, a 2(M) solution of LiBH$_4$ in THF (4.31 mL) was added slowly over a period of 30 minutes. The mixture was stirred for another 30 minutes, slowly poured over ice-water (ca. 20 g), acidified (0° C.) with 4(N) hydrochloric acid and extracted into ethyl acetate (3×75 mL). The combined organic layer was successively washed with 2% NaHCO$_3$ solution (2×20 mL), H$_2$O (1×10 mL), brine (1×20 mL), dried over Na$_2$SO$_4$ and concentrated to give a crude product. Purification by flash column chromatography (silica gel, 20% methylene chloride in ethyl acetate) yielded 1.275 g of Compound 39.

39: White solid, mp 140°–142° C.; R$_f$ (ethyl acetate): 0.53; $^1$H-NMR (300 MHz, CDCl$_3$) δ 7.40–7.10 (m, 10H), 6.90 (d, 1H), 5.50 (d, 1H), 4.50 (q, 2H), 4.20 (m, 1H), 4.00 (m, 1H), 3.80 (dd, 1H), 3.70–3.45 (m, 3H), 2.90–2.70 (m, 2H), 2.85 (s, 3H), 2.60 (t, 1H).

Example 34

Synthesis of Compound 40

This compound was synthesized following the general procedure described for the synthesis of Compound 20. Thus the oxidation of 0.813 g of Compound 39 by 1.70 g of Dess-Martin reagent in 20 mL of methylene chloride generated 0.77 g of Compound 40 of the invention.

40: White solid, mp 75°–85° C.(softening to melt); R$_f$ (ethyl acetate): 0.62; $^1$H-NMR (300 MHz, CDCl$_3$) δ 9.60 (s, 1H), 7.40–7.00 (m, 11H), 5.30 (d, 1H), 4.70 (q, 1H), 4.50 (q, 2H), 4.10 (q, 1H), 3.85 (dd, 1H), 3.60 (dd, 1H), 3.15 (m, 2H), 2.85 (s, 3H).

Example 35

Synthesis of Compound 41

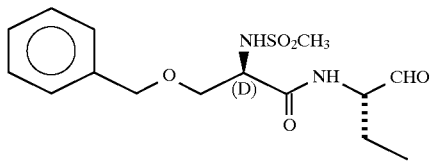

This compound was synthesized following Scheme 7, as described above, except that (L)-Abu-OMe hydrochloride salt instead of (L)-Phe-OMe hydrochloride salt was used in the first step.

41: White solid, mp 75°–83° C. (softening to melt); R$_f$ (90% CH$_2$Cl$_2$-9% CH$_3$OH-1% conc. NH$_4$OH): 0.52; $^1$H-NMR (300 MHz, CDCl$_3$) δ 9.55 (s, 1H), 7.30 (m, 6H), 5.65 (d, 1H), 4.55 (q, 2H), 4.45 (q, 1H), 4.20 (q, 1H), 3.85 (q, 1H), 3.75 (q, 1H), 2.95 (s, 3H), 1.95 (m, 1H), 1.70 (m, 1H), 0.90 (t, 3H).

Example 36

Synthesis of Compound 42

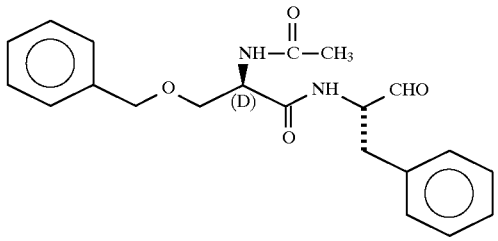

This compound was synthesized following Scheme 7, as described above, except that acetyl chloride, instead of methanesulfonyl chloride, was used in the preparation of the analog of Compound 38.

42: White solid, mp 118°–123° C. (softening to melt); R$_f$ (90% CH$_2$Cl$_2$-9% CH$_3$OH-1% conc. NH$_4$OH): 0.45; $^1$H-NMR (300 MHz, CDCl$_3$) δ 9.60 (s, 1H), 7.30 (m, 8H), 7.10 (dd, 2H), 6.95 (d, 1H), 6.30 (d, 1H), 4.70 (q, 1H), 4.60 (m, 1H), 4.50 (q, 2H), 3.85 (dd, 1H), 3.45 (dd, 1H), 3.10 (d, 2H), 2.00 (s, 3H).

Example 37

Synthesis of Compound 43

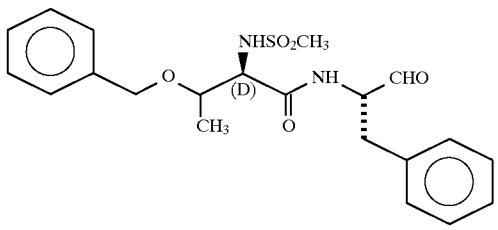

This compound was synthesized following Scheme 7, as described above, except that Boc—(D)-Thr(Bzl), instead of Boc—(D)—Ser(Bzl), was used in the first step.

43: White solid, mp 102°–108° C.(softening to melt); R$_f$ (90% CH$_2$Cl$_2$-9% CH$_3$OH-1% conc. NH$_4$OH): 0.57; $^1$H-NMR (300 MHz, CDCl$_3$) δ 9.60 (s, 1H), 7.40–7.00 (m, 111H), 5.40 (d, 1H), 4.75 (q, 1H), 4.50 (d, 2H), 4.00 (m 2H), 3.20 (q, 1H), 3.00 (q, 1H), 2.80 (s, 3H), 1.05 (d, 3H).

Example 38

Synthesis of Compound 44

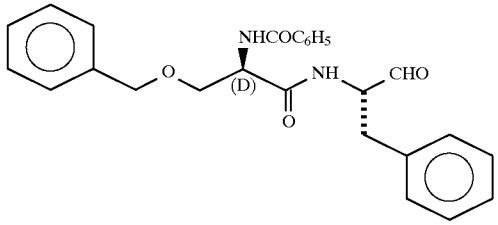

This compound was synthesized following Scheme 7, as described above, except that benzoyl chloride, instead of methanesulfonyl chloride, was used in preparation of the analog of Compound 38.

44: White solid, mp 142°–147° C. (softening to melt); $R_f$ (90% $CH_2Cl_2$-9% $CH_3OH$-1% conc. $NH_4OH$): 0.54; $^1$H-NMR (300 MHz, $CDCl_3$) δ 9.60 (s, 1H), 7.80 (d, 2H), 7.60–7.00 (m, 15H), 4.80 (m, 1H), 4.70 (q, 1H), 4.50 (d, 2H), 4.00 (dd, 1H), 3.55 (dd, 1H), 3.10 (d, 2H).

Example 39

Synthesis of Compound 45

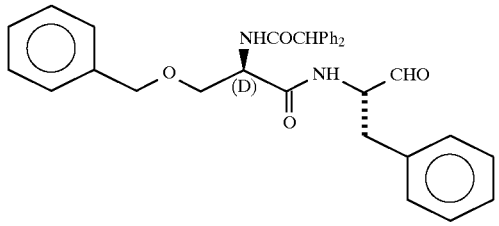

This compound was synthesized following Scheme 7, as described above, except that diphenylacetic acid (in the presence of DCC and HOBt), instead of methanesulfonyl chloride and NMM, was used in preparation of the analog of Compound 38.

45: White solid, mp 148°–153° C. (softening to melt); $R_f$ (90% $CH_2Cl_2$-9% $CH_3OH$-1% conc. $NH_4OH$): 0.60; $^1$H-NMR (300 MHz, $CDCl_3$) δ 9.55 (s, 1H), 7.40–7.00 (m, 20H), 6.85 (d, 1H), 6.45 (d, 1H), 4.95 (s, 1H), 4.65 (m, 2H), 4.40 (q, 2H), 3.85 (dd, 1H), 3.45 (dd, 1H), 3.10 (m, 2H).

Example 40

Synthesis of Compound 46

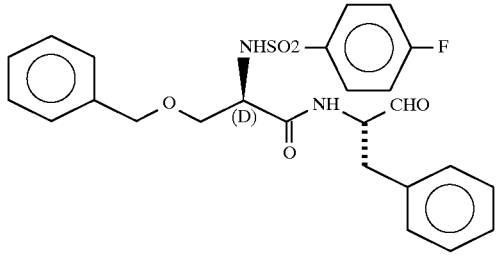

This compound was synthesized following Scheme 7, as described above, except that 4-fluorobenzenesulfonyl chloride, instead of methanesulfonyl chloride, was used in preparation of the analog of Compound 38.

46: White solid, mp 132°–136° C. (softening to melt); $R_f$ (90% $CH_2Cl_2$-9% $CH_3OH$-1% conc. $NH_4OH$): 0.54; $^1$H-NMR (300 MHz, $CDCl_3$) δ 9.55 (s, 1H), 7.80 (q, 2H), 7.40–7.00 (m, 13H), 5.60 (d, 1H), 4.60 (q, 1H), 4.35 (q, 2H), 3.80 (m, 2H), 3.25 (dd, 1H), 3.10 (d, 2H).

Example 41

Synthesis of Compound 47

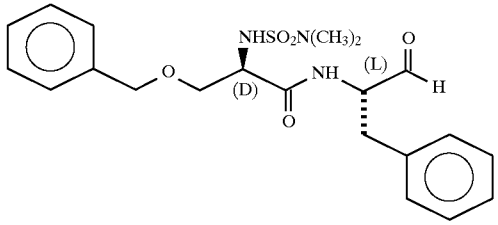

This compound was synthesized following Scheme 7, as described above, except that dimethylsulfamoyl chloride, instead of methanesulfonyl chloride, was used in preparation of the analog of Compound 38.

47: White solid, mp 90°–100° C. (softening to melt); $R_f$ (90% $CH_2Cl_2$-9% $CH_3OH$-1% conc. $NH_4OH$): 0.54; $^1$H-NMR (300 MHz, $CDCl_3$) δ 9.60 (s, 1H), 7.40–7.10 (m, 11H), 5.25 (d, 1H), 4.70 (q, 1H), 4.45 (q, 2H), 4.00 (m, 1H), 3.90 (dd, 1H), 3.55 (dd, 1H), 3.15 (m, 2H), 2.70 (s, 6H).

Example 42

Synthesis of Compound 48

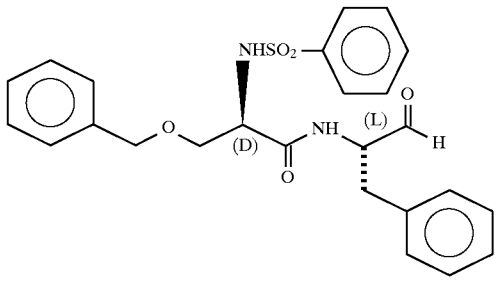

This compound was synthesized following Scheme 7, as described above, except that benzenesulfonyl chloride, instead of methanesulfonyl chloride, was used in preparation of the analog of Compound 38. The compound contained a minor amount of another diasteromer.

48: White solid, mp 110°–115° C.(softening to melt); $R_f$ (90% $CH_2Cl_2$-9% $CH_3OH$-1% conc. $NH_4OH$): 0.63; $^1$H-NMR (300 MHz, $CDCl_3$) δ 9.55 and 9.50 (2 singlets, 84:16, 1H), 7.80–7.00 (m, 16H), 5.60 (d, 1H), 4.60 (q, 1H), 4.30 (q, 2H), 3.80 (m, 2H), 3.30 and 3.20 (2sets of dd, 84:16, 1H), 3.10 and 3.05 (2sets of d, 84:16, 2H).

Example 43

Synthesis of Compound 49

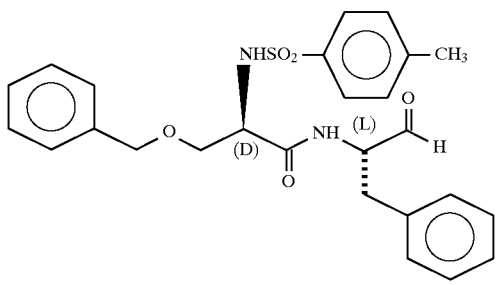

This compound was synthesized following Scheme 7, as described above, except that p-toluenesulfonyl chloride, instead of methanesulfonyl chloride, was used in preparation of the analog of Compound 38.

49: White solid, mp 113°–124° C. (softening to melt); $R_f$ (90% $CH_2Cl_2$-9% $CH_3OH$-1% conc. $NH_4OH$): 0.58; $^1$H-NMR (300 MHz, $CDCl_3$) δ 9.55 (s, 1H), 7.35 (d, 2H), 7.40–7.20 (m, 9H), 7.15 (m, 4H), 5.50 (d, 1H), 4.60 (q, 1H), 4.40 (d, 1H), 4.20 (d, 1H), 3.80 (m, 2H), 3.20 (dd, 1H), 3.10 (d, 2H), 2.40 (s, 3H).

Example 44

Synthesis of Compound 50

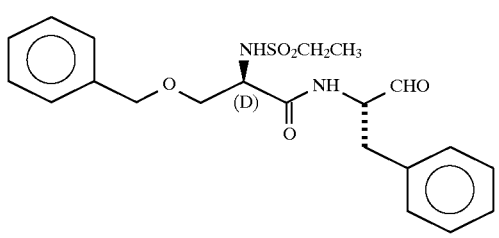

This compound was synthesized following Scheme 7, as described above, except that ethanesulfonyl chloride, instead of methanesulfonyl chloride, was used in preparation of the analog of Compound 38.

50: White solid, mp 125°–127° C. (softening to melt); $R_f$ (90% $CH_2Cl_2$-9% $CH_3OH$-1% conc. $NH_4OH$): 0.51; $^1$H-NMR (300 MHz, $CDCl_3$) δ 9.60 (s, 1H), 7.40–7.00 (m, 11H), 5.25 (d, 1H), 4.70 (q, 1H), 4.45 (q, 2H), 4.05 (m, 1H), 3.85 (dd, 1H), 3.60 (dd, 1H), 3.15 (m, 2H), 2.90 (q, 2H), 1.25 (t, 3H).

Example 45

Synthesis of Compound 51

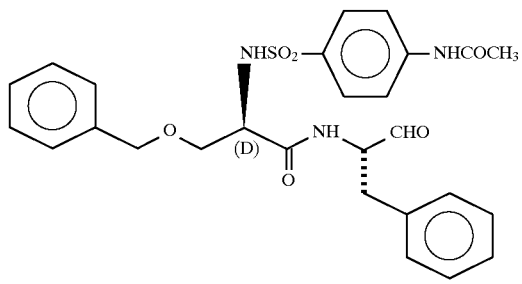

This compound was synthesized following Scheme 7, as described above, except that 4-acetamidobenzenesulfonyl chloride, instead of methanesulfonyl chloride, was used in preparation of the analog of Compound 38. Compound 51 contained a minor amount of another diasteromer.

51: White solid, mp 150°–156° C.(decomp.); $R_f$ (90% $CH_2Cl_2$-9% $CH_3OH$-1% conc. $NH_4OH$): 0.36; $^1$H-NMR (300 MHz, DMSO-$d_6$) δ 10.45 (s, 1H), 9.40 and 9.30 (2 sets of singlets, 86:14, 1H), 8.70 (2 overlapping d, 1H), 8.20 (t, 1H), 7.85 (m, 3H), 7.45 (m, 4H), 7.35 (m, 8H), 4.50–4.30 (m, 2H), 4.20 (m, 1H), 3.60 and 3.45 (2 sets of d, 2H), 3.20 (m, 1H), 2.85 (m, 1H), 2.20 (s, 3H).

Example 46

Synthesis of Compound 52

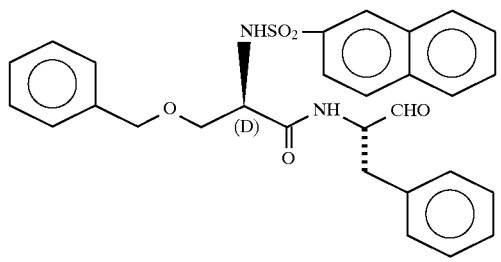

This compound was synthesized following Scheme 7, as described above, except that 2-naphthalenesulfonyl chloride, instead of methanesulfonyl chloride, was used in preparation of the analog of Compound 38.

52: White solid, mp 95°–105° C. (softening to melt); $R_f$ (90% $CH_2Cl_2$-9% $CH_3OH$-1% conc. $NH_4OH$): 0.54; $^1$H-NMR (300 MHz, $CDCl_3$) δ 9.50 (s, 1H), 8.40 (s, 1H), 7.90 (m, 4H), 7.70 (m, 4H), 7.40–7.00 (m, 9H), 65 (d, 1H), 4.55 (q, 1H), 4.30 (q, 2H), 3.80 (m, 2H), 3.20 (dd, 1H), 3.05 (d, 2H).

Example 47

Synthesis of Compound 53

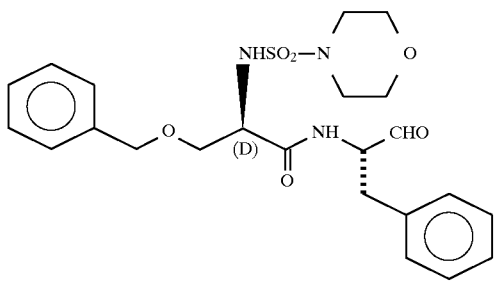

This compound was synthesized following Scheme 7, as described above, except that morpholinosulfonyl chloride, instead of methanesulfonyl chloride, was used in preparation of the analog of Compound 38.

53: White gum; $R_f$ (90% $CH_2Cl_2$-9% $CH_3OH$-1% conc. $NH_4OH$): 0.51; $^1$H-NMR (300 MHz, $CDCl_3$) δ 9.60 (s, 1H), 7.40–7.10 (m, 11H), 5.35 (d, 1H), 4.75 (q, 1H), 4.50 (q, 2H), 4.00 (m, 1H), 3.85 (m, 1H), 3.80–3.50 (m, 5H), 3.30–3.00 (m, 6H).

Example 48

Synthesis of Compound 54

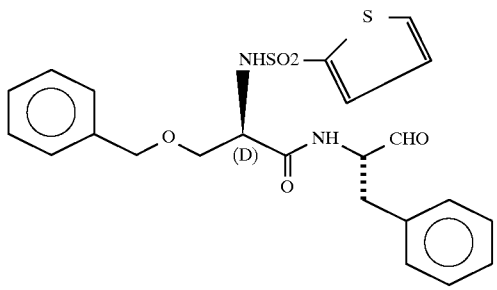

This compound was synthesized following Scheme 7, as described above, except that 2-thiophenesulfonyl chloride, instead of methanesulfonyl chloride, was used in preparation of the analog of Compound 38.

54: White solid, mp 105°–115° C.(softening to melt); $R_f$ (90% $CH_2Cl_2$-9% $CH_3OH$-1% conc. $NH_4OH$): 0.56; $^1$H-NMR (300 MHz, $CDCl_3$) δ 9.55 (s, 1H), 7.60 (m, 2H), 7.40–7.00 (m, 12H), 5.65 (d, 1H), 4.60 (q, 1H), 4.35 (q, 2H), 3.90 (m, 2H), 3.30 (m, 1H), 3.10 (d, 2H).

Example 49 of Compound 55

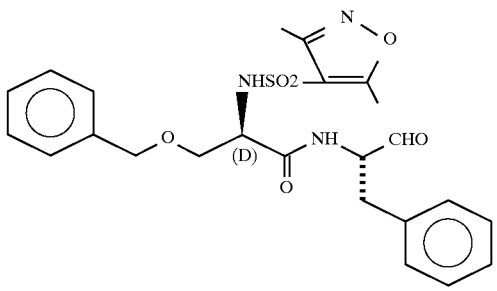

This compound was synthesized following Scheme 7, as described above, except that 3,5-dimethyl-4 isoxazolesulfonyl chloride, instead of methanesulfonyl chloride, was used in preparation of the analog of Compound 38.

55: White gum; $R_f$ (90% $CH_2Cl_2$-9% $CH_3OH$-1% conc. $NH_4OH$): 0.39; $^1$H-NMR (300 MHz, $CDCl_3$) δ 9.50 (s, 1H), 7.30–7.10 (m, 11H), 5.65 (d, 1H), 4.60 (q, 1H), 4.30 (q, 2H), 3.70 (m, 1H), 3.60 (m, 1H), 3.35 (t, 1H), 3.05 (d, 2H), 2.50 (s, 3H), 2.25 (s, 3H).

Scheme 8 shows the synthesis of Compound 59.

Scheme 8

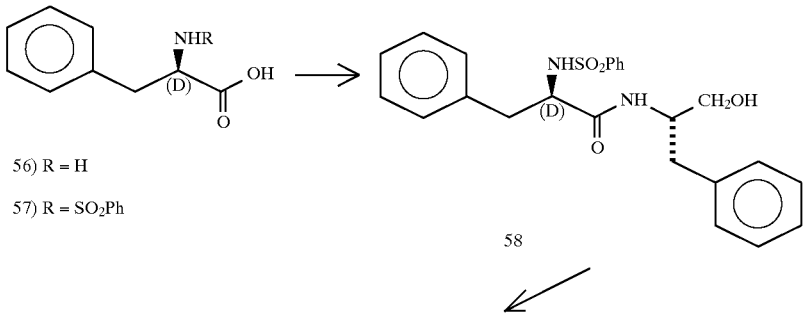

56) R = H
57) R = SO$_2$Ph

58

-continued
Scheme 8

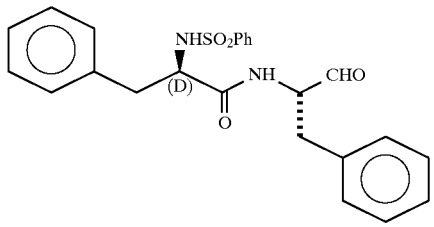

59

Example 50

Synthesis of Compound 59

To a stirred suspension of (D)-Phe (Compound 56, 2.00 g, 0.012 mol) in water (10 mL) was slowly added 1N NaOH (20 mL), followed by benzenesulfonyl chloride (3.20 g, 0.018 mol); pH of the reaction mixture was maintained at approx. 10~11 by periodic addition of 1N NaOH. After 2 h, the reaction mixture was acidified (pH approx. 2~3) with conc. hydrochloric acid and extracted into ethyl acetate (3×50 mL). The combined organic layer was washed with water (1×10 mL), brine (1×20 mL), dried (MgSO$_4$) and concentrated to give 2.00 g of crude Compound 57 which was used directly in the next step; $^1$H-NMR (300 MHz, CDCl$_3$) δ 7.80–7.00 (m, 11H), 5.10 (d, 1H), 4.25 (m, 1H), 3.10 (dd, 1H), 3.00 (dd, 1H).

One g of Compound 57 was coupled with 0.5 g of (s)-phenylalaninol, following the coupling procedure of Scheme 1, to generate 1.00 g of Compound 58 ; $^1$H-NMR (300 MHz, CDCl$_3$) δ 7.70–7.10 (a series of m, 13H), 6.90 (d, 2H), 6.40 (d, 1H), 5.05 (d, 1H), 4.05 (m, 1H), 3.85 (m, 1H), 3.50 (m, 2H), 2.85 (m, 2H), 2.75 (m, 2H), 2.30 (t, 1H).

Compound 58 was oxidized to Compound 59 by Dess-Martin reagent, as described above in Scheme 7, for the preparation of Compound 40.

59: White solid, mp 70°–75° C. (softening to melt); R$_f$ (90% CH$_2$Cl$_2$-9% CH$_3$OH-1% conc. NH$_4$OH): 0.50; $^1$H-NMR (300 MHz, CDCl$_3$) δ 9.45 (s, 1H), 7.60 (m, 4H), 7.40 (t, 3H), 7.30–7.10 (m, 6H), 6.90 (d, 2H), 6.70 (d, 1H), 4.90 (d, 1H), 4.60 (q, 1H), 3.90 (q, 1H), 3.15 (dd, 1H), 3.00 (dd, 1H), 2.90 (d, 2H).

Example 51

Synthesis of Compound 60

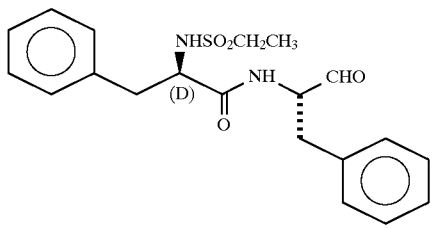

This compound was synthesized following Scheme 8, as described above, except that ethanesulfonyl chloride, instead of benzenesulfonyl chloride, was used in the first step.

60: White solid, mp 112°–116° C. (softening to melt); R$_f$ (90% CH$_2$Cl$_2$-9% CH$_3$OH-1% conc. NH$_4$OH): 0.53; $^1$H-NMR (300 MHz, CDCl$_3$) δ 9.60 (s, 1H), 7.40–7.20 (m, 8H), 7.10 (d, 2H), 6.65 (d, 1H), 5.10 (d, 1H), 4.70 (q, 1H), 4.15 (q, 1H), 3.20–2.90 (m, 4H), 2.70–2.50 (m, 2H), 1.00 (t, 3H).

Example 52

Synthesis of Compound 61

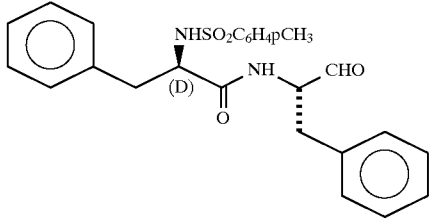

This compound was synthesized following Scheme 8, as described above, except that p-toluenesulfonyl chloride, instead of benzenesulfonyl chloride, was used in the first step.

61: White solid, mp 130°–135° C.(softening to melt); R$_f$ (90% CH$_2$Cl$_2$-9% CH$_3$OH-1% conc. NH$_4$OH): 0.47; $^1$H-NMR (300 MHz, CDCl$_3$) δ 9.55 (s, 1H), 7.50 (d, 2H), 7.40–7.10 (m, 10H), 6.90 (d, 2H), 6.80 (d, 1H), 4.85 (d, 1H), 4.60 (q, 1H), 3.85 (q, 1H), 3.15 (dd, 1H), 3.00 (dd, 1H), 2.90 (d, 2H), 2.40 (s, 3H).

Example 53

Synthesis of Compound 62

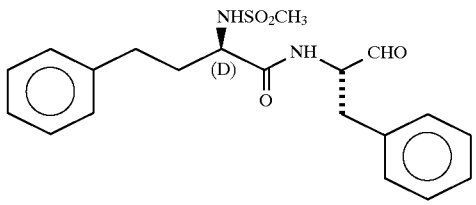

This compound was synthesized following Scheme 8, as described above, except that (D)-Homophe and methanesulfonyl chloride, instead of (D)-Phe and benzenesulfonyl chloride, respectively, were used in the first step.

62: White solid, mp 125°–130° C. (softening to melt); R$_f$ (90% CH$_2$Cl$_2$-9% CH$_3$OH-1% conc. NH$_4$OH): 0.45; $^1$H-NMR (300 MHz, CDCl$_3$) δ 9.65 (s, 1H), 7.40–7.00 (m, 10H), 6.30 (d, 1H), 5.05 (d, 1H), 4.80 (q, 1H), 3.90 (m, 1H), 3.20 (m, 2H), 2.80 (s, 3H), 2.65 (m, 2H), 1.90 (m, 2H).

Example 54

Synthesis of Compound 63

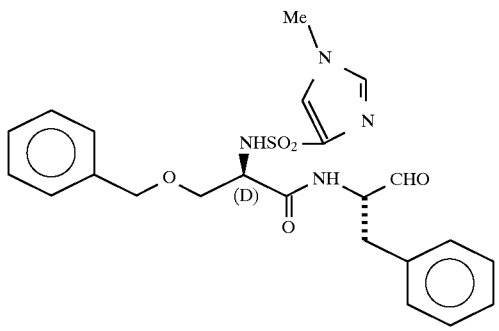

This compound was synthesized following Scheme 8, as described above, except that (D)-Ser(Bzl) and N-methyl-4-imidazolesulfonyl chloride, instead of (D)-Phe and methanesulfonyl chloride, respectively, were used in the first step.

63: White solid, mp 47°–56° C. (softening to melt);; $R_f$ (90% $CH_2Cl_2$-9% $CH_3OH$-1% conc. $NH_4OH$): 0.40; $^1$H-NMR (300 MHz, $CDCl_3$) δ 9.55 (s, 1H), 7.60 (d, 1H) 7.40–7.10 (m, 12H), 5.85 (d, 1H), 4.60 (q, 1H), 4.40 (q, 2H), 4.15 (m, 1H), 4.00 (dd, 1H), 3.70 (s, 3H), 3.50 (m, 1H), 3.10 (m, 2H).

Example 55

Synthesis of Compound 64

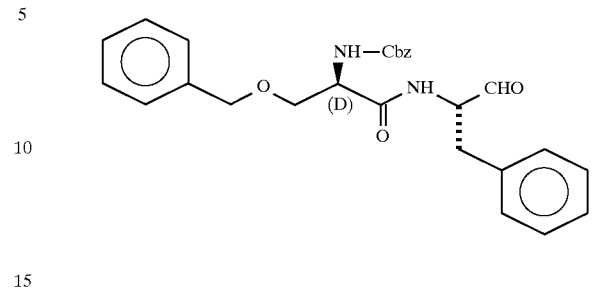

This compound was synthesized following Scheme 8, as described above, except that (D)-Ser(Bzl) and Cbz-OSuc, instead of (D)-Phe and methanesulfonyl chloride, respectively, were used in the first step.

64: White solid, mp 115°–120° C. (softening to melt);; $R_f$ (90% $CH_2Cl_2$-9% $CH_3OH$-1% conc. $NH_4OH$): 0.75; $^1$H-NMR (300 MHz, $CDCl_3$) δ 9.60 (s, 1H), 7.40–7.10 (m, 15H), 6.95 (broad d, 1H), 5.60 (broad d, 1H), 5.10 (s, 2H), 4.70 (broad q, 1H), 4.45 (q, 2H), 4.40 (m, 1H), 3.90 9d, 1H), 3.50 (dd, 1H), 3.10 (d, 2H).

Scheme 9 shows the synthesis of Compound 70.

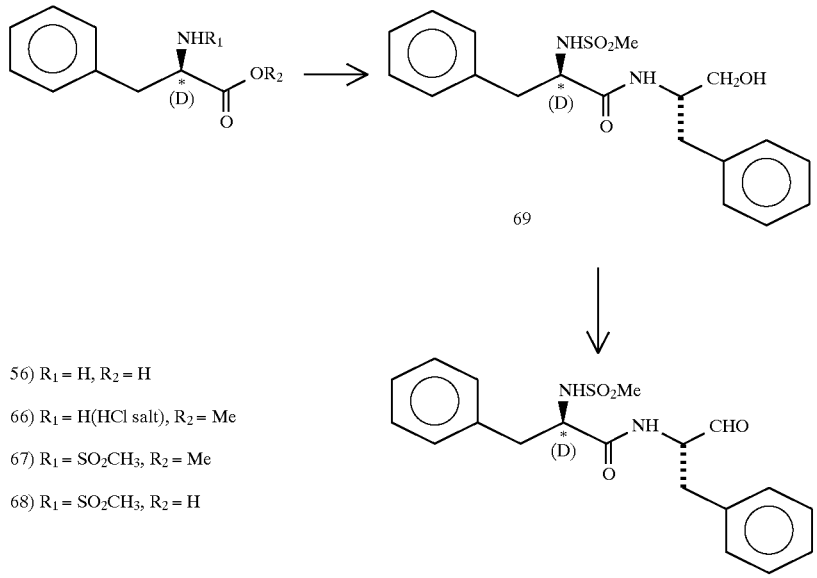

Scheme 9

56) $R_1$ = H, $R_2$ = H
66) $R_1$ = H(HCl salt), $R_2$ = Me
67) $R_1$ = $SO_2CH_3$, $R_2$ = Me
68) $R_1$ = $SO_2CH_3$, $R_2$ = H

Example 56

Synthesis of Compound 70

To a stirred solution of (D)-Phe (Compound 56, 2.00 g, 0.012 mol), or Boc-(D)-Phe (Compound 65), in methanol (40 mL), at 0° C. was added slowly thionyl chloride (2.90 g, 0.024 mol). The mixture was stirred at 0° C.for 1 h and then at room temperature overnight. Excess solvent and reagents were removed in vacuo to give 2.50 g of crude Compound 66. This product was treated with methanesulfonyl chloride, in the presence of triethylamine and methylene chloride, to generate Compound 67; $^1$H-NMR (300 MHz, CDCl$_3$) δ 7.40–7.15 (m, 5H), 4.85 (d, 1H), 4.40 (m, 1H), 3.80 (s, 3H), 3.15 (dd, 1H), 3.05 (dd, 1H), 2.65 (s, 3H).

Compound 67 was quantitatively hydrolyzed (LiOH, THF-H$_2$O, room temperature, 3 h) to Compound 68 which in turn was converted to Compound 70 via Compound 69 using the procedures described in Scheme 7 for the preparation of Compound 40.

70: White solid, mp 65°–70° C.(softening to melt); R$_f$ (90% CH$_2$Cl$_2$-9% CH$_3$OH-1% conc. NH$_4$OH): 0.44; $^1$H-NMR (300 MHz, CDCl$_3$) δ 9.55 (s, 1H), 7.40–7.00 (m, 10H), 6.80 (d, 1H), 5.30 (d, 1H), 4.75 (q, 1H), 4.10 (m, 1H), 3.20–3.00 (m, 3H), 2.90 (dd, 1H), 2.40 (s, 3H).

Example 57

Synthesis of Compound 71

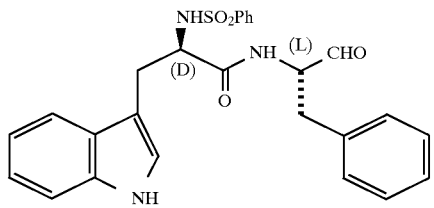

This compound was synthesized following Scheme 9, as described above, except that (D)-Trp and benzenesulfonyl chloride, instead of (D)-Phe and methanesulfonyl chloride, respectively, were used in the first step.

71: White solid, mp 125°–135° C. (softening to melt); R$_f$ (90% CH$_2$Cl$_2$-9% CH$_3$OH-1% conc. NH$_4$OH): 0.55; $^1$H-NMR (300 MHz, CDCl$_3$) δ 9.35 (s, 1H), 8.40 (broad, 1H), 7.40–6.80 (m, 16H), 5.35 (d, 1H), 4.55 (q, 1H), 4.00 (q, 1H), 3.20–2.90 (m, 4H).

Example 58

Synthesis of Compound 72

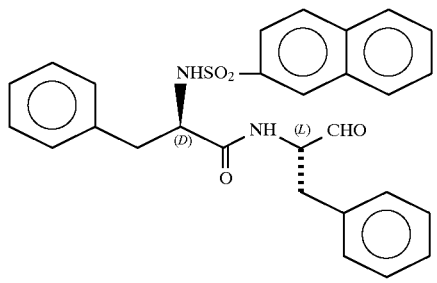

This compound was synthesized following Scheme 9, as described above, except that 2-naphthalenesulfonyl chloride, instead of methanesulfonyl chloride, was used in the first step.

72: White solid, mp 120°–130° C. (softening to melt); R$_f$ (90% CH$_2$Cl$_2$-9% CH$_3$OH-1% conc. NH$_4$OH): 0.51; $^1$H-NMR (300 MHz, CDCl$_3$) δ 9.40 (s, 1H), 8.05 (s, 1H), 7.90 (d, 2H), 7.80 (d, 1H), 7.65 (m, 2H), 7.55 (dd, 1H), 7.30 (m, 3H), 7.00 (m, 5H), 6.80 (m, 3H), 5.00 (d, 1H), 4.50 (q, 1H), 3.95 (q, 1H), 3.10 (dd, 1H), 2.95 (dd, 1H), 2.90 (m, 2H).

Example 59

Synthesis of Compound 73

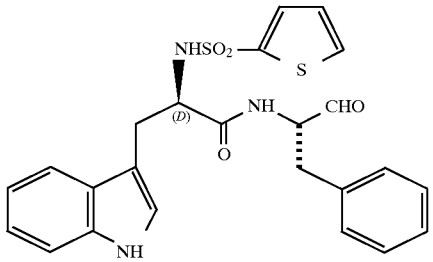

This compound was synthesized following Scheme 9, as described above, except that (D)-Trp and 2-thiophenesulfonyl chloride, instead of (D)-Phe and methanesulfonyl chloride, respectively, were used in the first step.

73: White solid, mp 90°–100° C. (softening to melt); R$_f$ (90% CH$_2$Cl$_2$-9% CH$_3$OH-1% conc. NH$_4$OH): 0.39; $^1$H-NMR (300 MHz, CDCl$_3$) δ 9.40 (s, 1H), 8.10 (s, 1H), 7.40–7.00 (m, 11H), 6.85 (m, 2H), 6.75 (d, 1H), 5.15 (d, 1H), 4.60 (q, 1H), 4.05 (q, 1H), 3.10 (m, 3H), 3.00 (dd, 1H).

Example 60

Synthesis of Compound 74

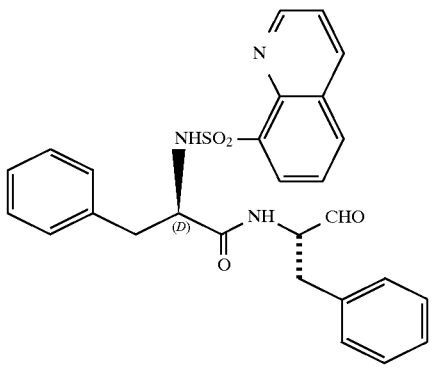

This compound was synthesized following Scheme 9, as described above, except that 8-quinolinesulfonyl chloride, instead of methanesulfonyl chloride, was used in the first step.

74: White solid, mp 80°–90° C. (softening to melt); R$_f$ (90% CH$_2$Cl$_2$-9% CH$_3$OH-1% conc. NH$_4$OH): 0.57; $^1$H-NMR (300 MHz, CDCl$_3$) δ 9.50 (s, 1H), 8.70 (m, 1H), 8.30 (m, 1H), 8.20 (m, 1H), 8.00 (m, 1H), 7.60 (t, 1H), 7.45 (q, 1H), 7.40–7.10 (m, 6H), 6.90–6.60 (m, 6H), 4.60 (q, 1H), 4.10 (m, 1H), 3.20 (dd, 1H), 3.05 (m, 2H), 2.80 (dd, 1H).

Example 61

Synthesis of Compound 75

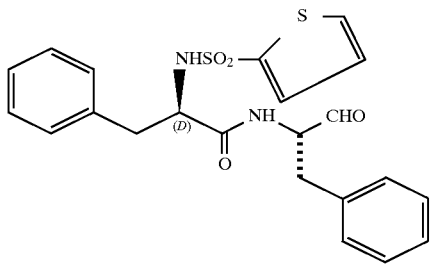

This compound was synthesized following Scheme 9, as described above, except that 2-thiophenesulfonyl chloride, instead of methanesulfonyl chloride, was used in the first step.

75: White solid, mp 55°–65° C. (softening to melt); $R_f$ (90% $CH_2Cl_2$-9% $CH_3OH$-1% conc. $NH_4OH$): 0.43; $^1H$-NMR (300 MHz, $CDCl_3$) δ 9.50 (s, 1H), 7.60 (dd, 1H), 7.40 (dd, 1H), 7.35–7.05 (m, 8H), 7.00 (t, 1H), 6.95 (m, 2H), 6.65 (d, 1H), 5.00 (d, 1H), 4.65 (q, 1H), 4.00 (q, 1H), 3.15 (dd, 1H), 3.00 (dd, 1H), 2.95 (d, 2H).

Example 62

Synthesis of Compound 76

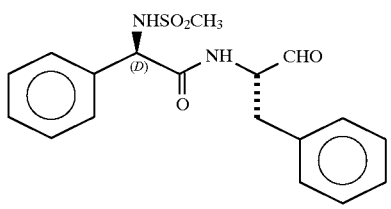

This compound was synthesized following Scheme 9, as described above, except that (D)-phenylglycine, instead of (D)-phenylalanine, was used in the first step.

76: White solid, mp 140°–145° C. (softening to melt); $R_f$ (90% $CH_2Cl_2$-9% $CH_3OH$-1% conc. $NH_4OH$): 0.45; $^1H$-NMR (300 MHz, $CDCl_3$) δ 9.60 (s, 1H), 7.40–7.05 (m, 8H), 6.75 (d, 2H), 6.00 (d, 1H), 5.85 (d, 1H), 5.05 (d, 1H), 4.80 (q, 1H), 3.05 (q, 2H), 2.65 (s, 3H).

Example 63

Synthesis of Compound 77

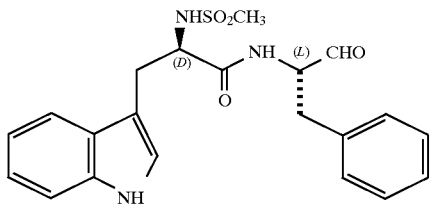

This compound was synthesized following Scheme 9, as described above, except that (D)-Trp, instead of (D)-phenylalanine, was used in the first step.

77: White solid, mp 105°–115° C. (softening to melt); $R_f$ (90% $CH_2Cl_2$-9% $CH_3OH$-1% conc. $NH_4OH$): 0.35; $^1H$-NMR (300 MHz, $CDCl_3$) δ 9.50 (s, 1H), 8.15 (s, 1H), 7.60 (d, 1H), 7.40–7.00 (m, 9H), 6.50 (d, 1H), 4.95 (d, 1H), 4.65 (q, 1H), 4.20 (q, 1H), 3.25 (m, 2H), 3.10 (dd, 1H), 2.95 (dd, 1H), 2.50 (s, 3H).

Example 64

Synthesis of Compound 78

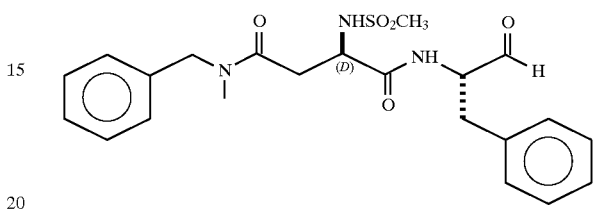

This compound was synthesized following Schemes 1 and 2, as described above, except that N-benzylmethylamine, instead of 1,2,3,4-tetrahydroisoquinoline, was used in the first step.

78: White solid, mp 75°–85° C. (softening to melt); $R_f$ (90% $CH_2Cl_2$-9% $CH_3OH$-1% conc. $NH_4OH$): 0.30; $^1H$-NMR (300 MHz, $CDCl_3$) δ 9.65 and 9.55 (2 singlets, rotomeric 1H), 7.70 (m, 1H), 7.40–7.00 (m, 10H), 6.20 (m, 1H), 4.70–4.30 (m, 4H), 3.30–2.90 (m, 4H), 2.85 (2 sets of d, 6H)

Example 65

Synthesis of Compound 79

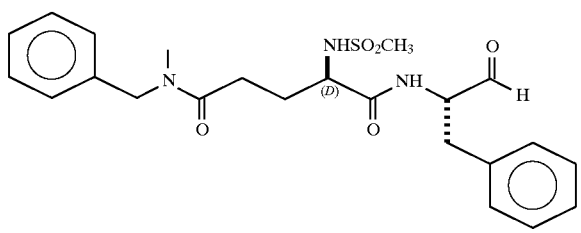

This compound was synthesized following Schemes 1 and 2, as described above, except that N-benzylmethylamine and Boc-(D)-Glu-OBz, instead of 1,2,3,4-tetrahydroisoquinoline and Boc-(D)-Asp-OBz, respectively, were used in the first step.

79: White solid, mp 75°–85° C.(softening to melt); $R_f$ (90% $CH_2Cl_2$-9% $CH_3OH$-1% conc. $NH_4OH$): 0.42; $^1H$-NMR (300 MHz, $CDCl_3$) of this compound is a complex one due to the presence of rotamers.

Example 66

Synthesis of Compound 80

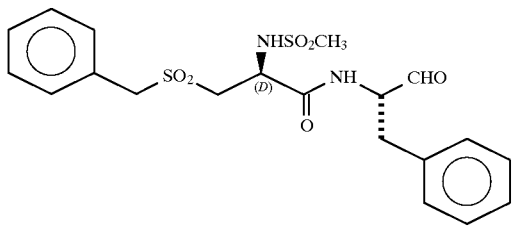

This compound was synthesized following the procedure of Scheme 7, as described above, with the following changes: Boc-(D)-Cys(Bzl) (Compound 21) was used instead of Boc-(D)-Ser(Bzl) (Compound 26), in the first step of the synthesis; and the sulfide moiety was converted to a sulfonyl moiety by Oxone® in MeOH before the final oxidation of the alcohol to the aldehyde by Dess-Martin reagent was carried out.

80: White solid, mp 125°–135° C.(softening to melt); $R_f$ (90% $CH_2Cl_2$-9% $CH_3OH$-1% conc. $NH_4OH$): 0.41; $^1$H-NMR (300 MHz,DMSO-$d_6$) δ 9.60 (s, 1H), 8.90 (d, 1H), 8.05 (d, 1H), 7.50–7.20 (m, 10H), 4.50 (m, 4H), 3.30 (d, 2H), 3.10 (m, 1H), 2.95 (s, 3H), 2.90 (m, 1H).

Example 67

Synthesis of Compound 81

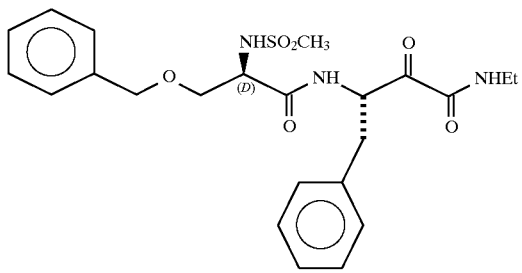

This compound was synthesized following the procedure outlined in Scheme 6, above, except that 3(S)amino-2(R,S)-hydroxy-4-phenylbutanoic acid ethyl amide (prepared by the method of Harbeson et al. *J. Med. Chem.* 1994, 37, 2918) was used instead of Compound 18a–b in the synthesis.

81: White solid, mp 137°–143° C.(softening to melt); $R_f$ (90% $CH_2Cl_2$-9% $CH_3OH$-1% conc. $NH_4OH$): 0.56; $^1$H-NMR (300 MHz, $CDCl_3$) δ 7.40–7.10 (m, 9H), 7.00 (m, 2H), 6.80 (broad, 1H), 5.60 (m, 1H), 5.15 (d, 1H), 4.50 (s, 1H), 4.45 (d, 1H), 4.00 (M, 1H), 3.80 (m, 1H), 3.60 (m, 1H), 3.35 (m, 3H), 3.05 (m, 1H), 2.80 (s, 3H), 1.20 (t, 3H).

Example 68

Synthesis of Compound 82

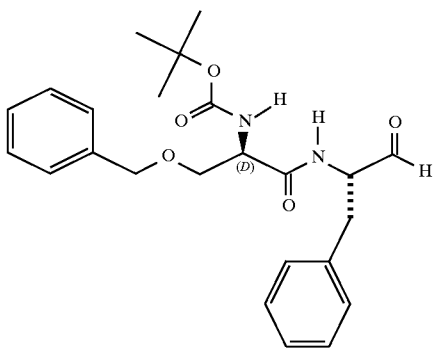

This compound was synthesized by coupling Boc-(D)-Ser(Bzl) and (S)-phenylalaninol, followed by oxidation, using the processes described in Scheme 1.

82: White gum; $R_f$ (90% $CH_2Cl_2$-9% $CH_3OH$-1% conc. $NH_4OH$): 0.65; $^1$H-NMR (300 MHz, $CDCl_3$) δ 9.60 (s, 1H), 7.40–7.00 (m, 11H), 5.30 (broad, 1H), 4.70 (m, 1H), 4.50 (m, 2H), 4.30 (m, 1H), 3.90 (m, 1H), 3.50 (m, 1H), 3.15 (d, 2H), 1.50 (s, 9H).

Example 69

Synthesis of Compound 83

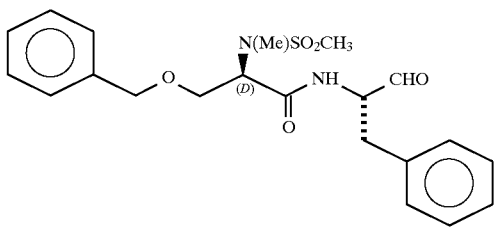

This compound was generated by N-methylation (MeI, $K_2CO_3$, DMF) of Compound 38 (Scheme 7), followed by reduction of the methyl ester to the corresponding alcohol and oxidation of the alcohol to the product aldehyde.

83: White gum; $R_f$ (90% $CH_2Cl_2$-9% $CH_3OH$-1% conc. $NH_4OH$): 0.53; $^1$H-NMR (300 MHz, $CDCl_3$) δ 9.60 (s, 1H), 7.40–7.00 (m, 11H), 4.60 (m, 2H), 4.45 (q, 2H), 3.95 (dd, 1H), 3.70 (t, 1H), 3.10 (m, 2H), 2.85 (s, 3H), 2.75 (s, 3H).

Example 70

Synthesis of Compound 84

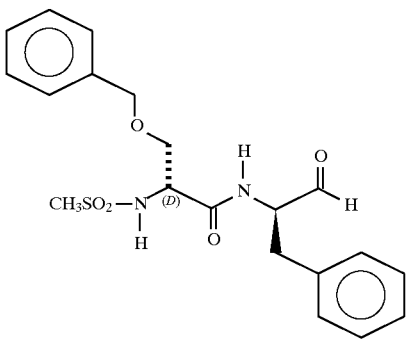

This compound was synthesized following Scheme 9, as described above, except that (D)-Ser(Bzl) instead of (D)-Phe was used in the first step, and (R)-phenylalaninol, instead of (S)-phenylalaninol, was used in the coupling step.

84: White gum; $R_f$ (90% CH$_2$Cl$_2$-9% CH$_3$OH-1% conc. NH$_4$OH): 0.41; $^1$H-NMR (300 MHz, CDCl$_3$) δ 9.60 (s, 1H), 7.40–7.00 (m, 11H), 5.30 (d, 1H), 4.75 (m, 1H), 4.50 (s, 2H), 4.10 (m, 1H), 3.85 (dd, 1H), 3.60 (dd, 1H), 3.10 (m, 2H), 2.90 (s, 3H).

Example 71

Synthesis of Compound 85

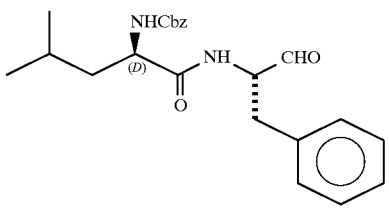

This compound was synthesized by coupling Cbz-(D)-Leu and (S)-phenylalaninol, followed by oxidation (Scheme 9).

85: White solid; mp 40°–50° C. (softening to melt); $R_f$ (90% CH$_2$Cl$_2$-9% CH$_3$OH-1% conc. NH$_4$OH): 0.65; $^1$H-NMR (300 MHz, CDCl$_3$) δ 9.60 (s, 1H), 7.40–7.10 (m, 10H), 6.50 (broad, 1H), 5.15 (s, 2H), 5.10 (broad, 1H), 4.70 (broad q, 1H), 4.20 (broad, 1H), 3.15 (d, 2H), 1.60–1.20 (m, 3H), 0.85 (broad d, 6H).

Example 72

Synthesis of Compound 86

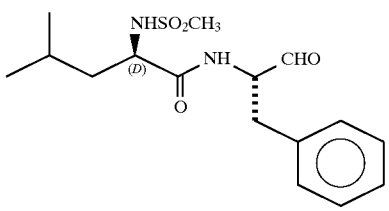

This compound was synthesized following the procedures of Scheme 8, as described above, except that (D)-Leu, instead of (D)-Phe, was used in the first step.

86: White solid; mp 95°–100° C. (softening to melt); $R_f$ (90% CH$_2$Cl$_2$-9% CH$_3$OH-1% conc. NH$_4$OH): 0.33; $^1$H-NMR (300 MHz, CDCl$_3$) δ 9.65 (s, 1H), 7.40–7.10 (m, 5H), 6.30 (d, 1H), 4.80 (m, 2H), 3.90 (m, 1H), 3.25 (dd, 1H), 3.15 (dd, 1H), 2.85 (s, 3H), 1.65–1.20 (m, 3H), 0.90 (t, 6H).

Example 73

Synthesis of Compound 87

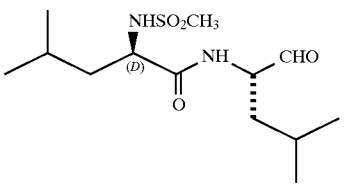

This compound was synthesized following the procedures of Scheme 7, as described above, except that Boc(D)-Leu instead of Boc-(D)-Ser(Bzl) was used in the first step, and (S)-leucinol instead of (S)-phenylalaninol was used in the coupling step.

87: White gum; $R_f$ (90% CH$_2$Cl$_2$-9% CH$_3$OH-1% conc. NH$_4$OH): 0.40; $^1$H-NMR (300 MHz, CDCl$_3$) δ 9.60 (s, 1H), 6.15 (d, 1H), 5.00 (d, 1H), 4.60 (m, 1H), 4.00 (m, 1H), 3.00 (s, 3H), 1.90–1.40 (m, 6H), 1.00 (m, 12H).

Example 74

Synthesis of Compound 88

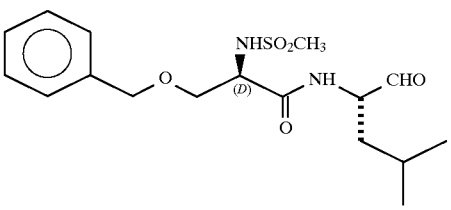

This compound was synthesized following the procedures of Scheme 9, as described above, except that Boc-(D)-Ser (Bzl), instead of (D)-Phe was used in the first step and (S)-leucinol, instead of (S)-phenylalaninol, was used in an intermediate step.

88: White gum; $R_f$ (90% CH$_2$Cl$_2$-9% CH$_3$OH-1% conc. NH$_4$OH): 0.46; $^1$H-NMR (300 MHz, CDCl$_3$) δ 9.60 (s, 1H), 7.40–7.20 (m, 5H), 6.95 (d,1H), 5.30 (d, 1H), 4.55 (m, 3H), 4.15 (m, 1H), 3.90 (m, 1H), 3.75 (dd, 1H), 2.95 (s, 3H), 1.70–1.20 (m, 3H), 0.90 (m, 6H).

Example 75

Synthesis of Compound 89

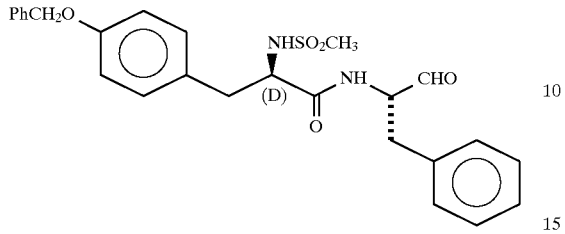

This compound was synthesized following the procedures of Scheme 9, as described above, except that Boc-(D)-Tyr(Bzl) instead of (D)-Phe was used in the first step.

89: White solid; mp 140°–145° C. (softening to melt); $R_f$ (90% $CH_2Cl_2$-9% $CH_3OH$-1% conc. $NH_4OH$): 0.34; $^1$H-NMR (300 MHz, $CDCl_3$) δ 9.60 (s, 1H), 7.45–7.20 (m, 5H), 7.10 (d, 4H), 6.90 (d, 2H), 6.55 (d, 1H), 5.05 (s, 2H), 4.85 (q, 1H), 4.70 (q, 1H), 4.05 (q, 1H), 3.10 (m, 2H), 2.90 (q, 1H), 2.45 (s, 3H).

Example 76

Synthesis of Compound 90

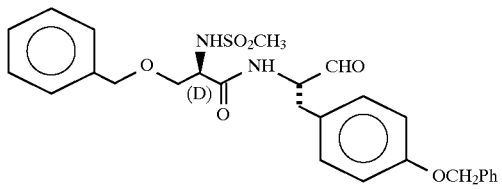

This compound was synthesized following the procedures of Scheme 9, as described above, with the following changes: Boc-(D)-Ser(Bzl) was used instead of (D)-Phe in the first step; (L)-Tyr(Bzl)-OMe, was used instead of (S)-phenylalaninol in an intermediate step; and the ester moiety was subsequently reduced ($NaBH_4$, EtOH) to the alcohol moiety before the final oxidation step.

90: White solid; mp 105°–106° C. (softening to melt); $R_f$ (90% $CH_2Cl_2$-9% $CH_3OH$-1% conc. $NH_4OH$): 0.38; $^1$H-NMR (300 MHz, $CDCl_3$) δ 9.60 (s, 1H), 7.45–7.20 (m, 10H), 7.15 (d, 1H), 7.00 (d, 2H), 6.85 (d, 2H), 5.25 (d, 1H), 5.00 (s, 2H), 4.70 (q, 1H), 4.45 (q, 2H), 4.10 (m, 1H), 3.85 (dd, 1H), 3.60 (dd, 1H), 3.10 (m, 2H), 2.85 (s, 3H).

Example 77

Synthesis of Compound 91

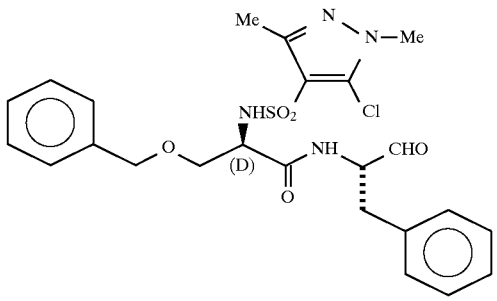

This compound was synthesized using the procedures of Scheme 7, as described above, except that 5-chloro-1,3-dimethylpyrazole-4-sulfonyl chloride instead of methanesulfonyl chloride was used in the first step.

91: White solid; mp 50°–60° C. (softening to melt); $R_f$ (90% $CH_2Cl_2$-9% $CH_3OH$-1% conc. $NH_4OH$): 0.57; $^1$H-NMR (300 MHz, $CDCl_3$) δ 9.60 and 9.55 (2 singlets, 5:1, 1H), 7.40–7.00 (m, 11H), 5.70 (d, 1H), 4.65 (q, 1H), 4.40 (q, 2H), 3.90–3.60 (m, 2H), 3.80 (s, 3H), 3.40 (dd, 1H), 3.10 (2 sets of d, 5:1, 2H), 2.40 (s, 3H).

Example 78

Synthesis of Compound 92

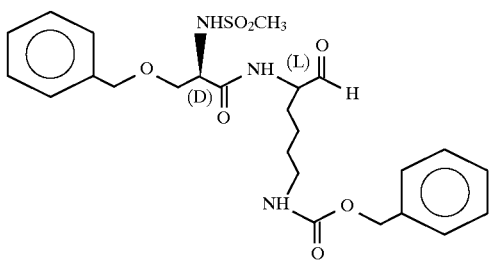

This compound was synthesized using the procedures of Scheme 8, as described above, with the following changes: (D)-Ser(Bzl) and methanesulfonyl chloride, instead of (D)-Phe and benzenesulfonyl chloride were used in the first step; (L)-Lys(Cbz)-OMe hydrochloride salt, instead of (S)-phenylalaninol, was used in an intermediate step; and the ester moiety was subsequently reduced ($NaBH_4$, EtOH) to the alcohol before the final oxidation step.

92: White solid; mp 125°–135° C. (softening to melt); $R_f$ (90% $CH_2Cl_2$-9% $CH_3OH$-1% conc. $NH_4OH$): 0.40; $^1$H-NMR (300 MHz, $CDCl_3$) δ 9.55 (s, 1H), 7.40–7.15 (m, 11H), 5.25 (d, 1H), 5.10 (s, 2H), 4.90 (broad, 1H), 4.55 (q, 2H), 4.45 (m, 1H), 4.15 (q, 1H), 3.85 (dd, 1H), 3.70 (dd, 1H), 3.15 (q, 2H), 2.90 (s, 3H), 1.90 (m, 1H), 1.70 (m, 1H), 1.50 (m, 2H), 1.30 (m, 2H).

Example 79

Synthesis of Compound 93

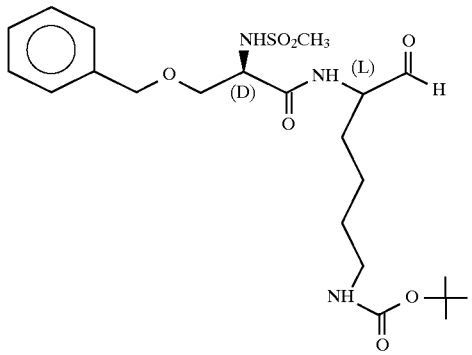

This compound was synthesized following the procedures of Scheme 8, as described above, with the following changes: (D)-Ser(Bzl) and methanesulfonyl chloride, instead of (D)-Phe and benzenesulfonyl chloride, were used in the first step; (L)-Lys(Boc)-OMe hydrochloride salt, instead of (S)-phenylalaninol, was used in an intermediate step; and the ester moiety was subsequently reduced (NaBH$_4$, EtOH) to the alcohol before the final oxidation step.

93: White solid; mp 130°–135° C.(softening to melt); R$_f$ (90% CH$_2$Cl$_2$-9% CH$_3$OH-1% conc. NH$_4$OH): 0.47; $^1$H-NMR (300 MHz, CDCl$_3$) δ 9.55 (s, 1H), 7.40–7.20 (m, 6H), 5.50 (broad d, 1H), 4.65–4.40 (m, 4H), 4.15 (q, 1H), 3.85 (dd, 1H), 3.75 (dd, 1H), 3.05 (m, 2H), 2.95 (s, 3H), 1.90 (m, 1H), 1.65 (m, 1H), 1.60–1.20 (m, 4H), 1.45 (s, 9H).

Example 80

Synthesis of Compound 94

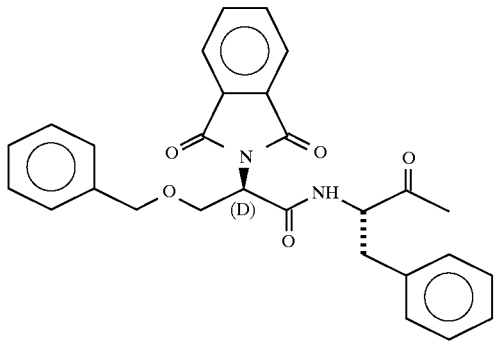

This compound was synthesized following the procedures of Scheme 8, as described above, except that (D)-Ser(Bzl) and N-carbethoxyphthalimide (in the presence of aqueous Na$_2$CO$_3$), were used in the first step, instead of (D)-Phe and benzenesulfonyl chloride. The final product showed some racemization had occurred.

94: White solid; mp 40°–50° C. (softening to melt); R$_f$ (90% CH$_2$Cl$_2$-9% CH$_3$OH-1% conc. NH$_4$OH): 0.70; $^1$H-NMR (300 MHz, CDCl$_3$) δ 9.65 and 9.60 (2 singlets, 7:3, 1H), 7.80 (m, 2H), 7.70 (m, 2H), 7.60 (t, 1H), 7.40–7.10 (m, 10H), 5.00 (m, 1H), 4.75 (q, 1H), 4.60–4.30 (m, 3H), 3.70 (m, 1H), 3.25 and 3.15 (2 sets of doublets, 2H).

Example 81

Synthesis of Compounds 95 and 96

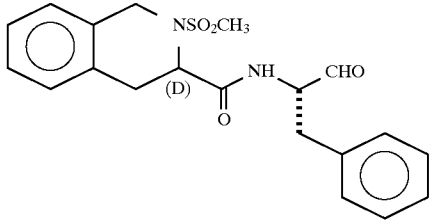

These compounds were synthesized following the procedures of Scheme 7, as described above, except that Boc-(D)-Tic, instead of Boc-(D)-Ser(Bzl) was used in the first step. However, racemization was observed during the synthesis, and the isomers were separated after the sulfonylation step. Individual isomers were converted separately in the final two steps to give the product aldehydes.

Isomer I (95): Pale yellow solid; mp 55°–65° C.(softening to melt); R$_f$ (90% CH$_2$Cl$_2$-9% CH$_3$OH-1% conc. NH$_4$OH): 0.70; $^1$H-NMR (300 MHz, CDCl$_3$) δ 9.40 (s, 1H), 7.30–7.10 (m, 9H), 7.00 (d, 1H), 7.55 (m, 3H), 7.35 (d, 1H), 3.20 (d, 2H), 3.10 (d, 2H), 2.60 (s, 3H).

Isomer II (96): Pale yellow solid; mp 65°–75° C. (softening to melt); R$_f$ (90% CH$_2$Cl$_2$-9% CH$_3$OH-1% conc. NH$_4$OH): 0.53; $^1$H-NMR (300 MHz, CDCl$_3$) δ 9.55 (s, 1H), 7.30–7.00 (m, 10H), 4.60–4.40 (m, 3H), 4.05 (d, 1H), 3.20–3.05 (m, 3H), 3.00 (q, 1H), 2.60 (s, 3H).

Example 82

Synthesis of Compounds 97 and 98

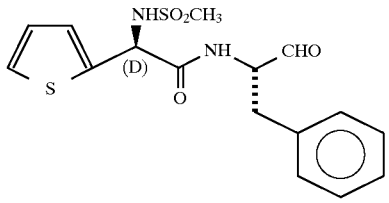

These compounds were synthesized following the procedures of Scheme 8, as described above, except that (D and L)-thiopheneglycine, instead of (D)-Phe, was used in the first step. Diastereomers were separated after the first step. Individual isomers were converted separately to the product aldehydes. Stereochemistry around the chiral center in isomers I and II was tentatively assigned (L) and (D) respectively, based on comparison of their enzyme inhibitory activity with that of other members of the series with known configuration.

Isomer I (97): Pale yellow solid; mp 65°–75° C.(softening to melt); R$_f$ (90% CH$_2$Cl$_2$-9% CH$_3$OH-1% conc. NH$_4$OH): 0.38; $^1$H-NMR (300 MHz, Acetone-d$_6$) δ 9.65 (s, 1H), 8.10 (d, 1H), &.50–7.00 (m, 8H), 6.85 (d, 1H), 5.45 (d, 1H), 4.55 (m, 1H), 3.30 (dd, 1H), 3.00 (dd, 1H), 2.70 (s, 3H).

Isomer II (98): Pale yellow solid; mp 151°–154° C.(softening to melt); R$_f$ (90% CH$_2$Cl$_2$-9% CH$_3$OH-1% conc. NH$_4$OH): 0.33; $^1$H-NMR (300 MHz, DMSO-d$_6$) δ 9.75 (s, 1H), 9.05 (d, 1H), 8.30 (d, 1H), 7.65 (d, 1H), 7.35 (m, 5H), 7.10 (t, 1H), 6.95 (d, 1H), 5.55 (d, 1H), 4.70 (m, 1H), 3.40 (dd, 1H), 3.00 (dd, 1H), 2.95 (s, 3H).

Example 83

Synthesis of Compounds 99 and 100

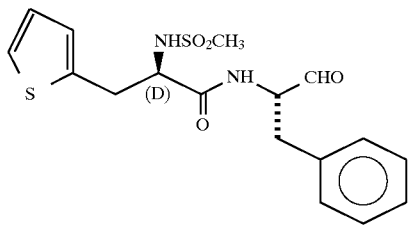

These compounds were synthesized following the procedures of Scheme 8, as described above, except that (D and L)-thiophenealanine instead of (D)-Phe was used in the first step. Diastereomers were separated after the first step. Individual isomers were converted separately to the product aldehydes. Isomer I was also prepared separately starting with (L)- thiophenealanine. Thus isomer II, Compound 100, has the (D)-configuration at the $P_2$ position.

Isomer I (99): White solid; mp 93°–98° C. (softening to melt); $R_f$ (90% $CH_2Cl_2$-9% $CH_3OH$-1% conc. $NH_4OH$): 0.53; $^1$H-NMR (300 MHz, $CDCl_3$) δ 9.60 (s, 1H), 7.40–7.20 (m, 4H), 7.15 (d, 2H), 6.95 (dd, 1H), 6.90 (d, 1H), 6.75 (d, 1H), 5.00 (d, 1H), 4.70 (q, 1H), 4.15 (q, 1H), 3.30 (m, 2H), 3.10 (m, 2H), 2.65 (s, 3H).

Isomer II (100): White solid; mp 124°–128° C. (softening to melt); $R_f$ (90% $CH_2Cl_2$-9% $CH_3OH$-1% conc. $NH_4OH$): 0.49; $^1$H-NMR (300 MHz, $CDCl_3$) δ 9.60 (s, 1H), 7.40–7.20 (m, 4H), 7.15 (d, 2H), 6.95 (dd, 1H), 6.90 (d, 1H), 6.80 (d, 1H), 5.20 (d, 1H), 4.75 (q, 1H), 4.15 (m, 1H), 3.30 (dd, 1H), 3.20 (dd, 1H), 3.10 (m, 2H), 2.60 (s, 3H).

Example 84

Synthesis of Compound 101

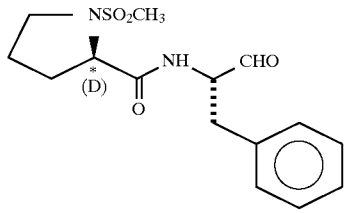

This compound was synthesized following the procedures of Scheme 8, as described above, except that (D)-proline and methanesulfonyl chloride, instead of (D)-Phe and benzenesulfonyl chloride, were used in the first step;

101: White gum; $R_f$ (90% $CH_2Cl_2$-9% $CH_3OH$-1% conc. $NH_4OH$): 0.33; $^1$H-NMR (300 MHz, $CDCl_3$) δ 9.65 (s, 1H), 7.40–7.10 (m, 5H), 7.05 (d, 1H), 4.65 (q, 1H), 4.20 (dd, 1H), 3.50 (m, 1H), 3.35 (q, 1H), 3.20 (d, 2H), 2.85 (s, 3H), 2.30 (m, 1H), 2.10 (m, 1H), 1.90 (m, 2H).

Example 85

Synthesis of Compound 102

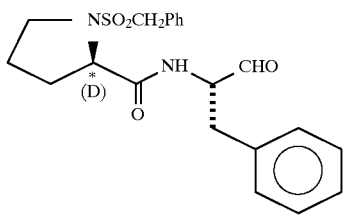

This compound was synthesized following the procedures of Scheme 7, as described above, except that Boc-(D)-proline instead of Boc-(D)-Ser(Bzl) was used in the first step, and α-toluenesulfonyl chloride instead of methanesulfonyl chloride was used for preparation of the N-sulfonyl intermediate compound.

102: White solid; mp 40°–50° C.(softening to melt); $R_f$ (90% $CH_2Cl_2$-9% $CH_3OH$-1% conc. $NH_4OH$): 0.66; $^1$H-NMR (300 MHz, $CDCl_3$) δ 9.55 (s, 1H), 7.45–7.10 (m, 10H), 6.85 (d, 1H), 4.55 (q, 1H), 4.25 (s, 2H), 4.05 (dd, 1H), 3.15 (m, 2H), 3.10 (dd, 2H), 2.10 (m, 1H), 1.90 (m, 1H), 1.80 (m, 2H).

Example 86

Synthesis of Compound 103

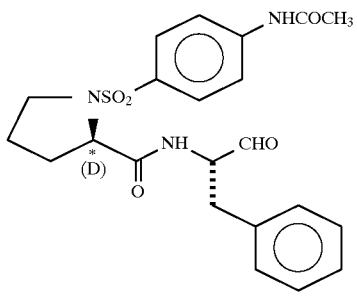

This compound was synthesized following the procedures of Scheme 7, as described above, except that Boc-(D)-proline instead of Boc-(D)-Ser(Bzl) was used in the first step, and 4-acetamidobenzenesulfonyl chloride, instead of methanesulfonyl chloride, was used for preparation of the N-sulfonyl intermediate compound.

103: White solid; mp 75°–85° C. (softening to melt); $R_f$ (90% $CH_2Cl_2$-9% $CH_3OH$-1% conc. $NH_4OH$): 0.26; $^1$H-NMR (300 MHz, $CDCl_3$) δ 9.65 (s, 1H), 7.65 (m, 5H), 7.40–7.20 (m, 6H), 4.65 (q, 1H), 4.05 ((dd, 1H), 3.45 (m, 1H), 3.20 (m, 2H), 3.15 (m, 1H), 2.20 (s, 3H), 2.10 (m, 1H), 1.80–1.50 (m, 3H).

Example 87

Synthesis of Compound 104

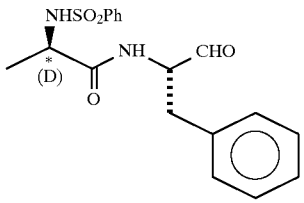

This compound was synthesized following the procedures of Scheme 8, as described above, except that (D)-Ala instead of (D)-Phe was used in the first step.

104: White gum; $R_f$ (90% $CH_2Cl_2$-9% $CH_3OH$-1% conc. $NH_4OH$): 0.33; $^1$H-NMR (300 MHz, $CDCl_3$) δ 9.50 (s, 1H), 7.85 (d, 2H), 7.55 (m, 3H), 7.30 (in, 3H), 7.15 (d, 2H), 6.60 (d, 1H), 5.25 (d, 1H), 4.60 (q, 1H), 3.80 (m, 1H), 3.10 (d, 2H), 1.20 (d, 3H).

Example 88

Synthesis of Compound 105

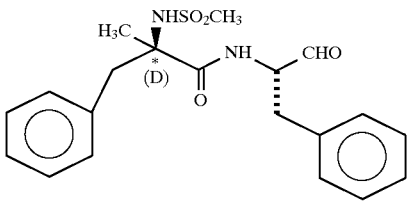

This compound was synthesized following the procedures of Scheme 8, as described above, except that (D)-α-Me-Phe and methanesulfonyl chloride, instead of (D)-Phe and benzenesulfonyl chloride, were used in the first step. Crude product showed the presence of one product aldehyde. However, racemization occurred during purification of the product by chromatography through a florisil column.

105: White gum; $R_f$ (90% $CH_2Cl_2$-9% $CH_3OH$-1% conc. $NH_4OH$): 0.42; $^1$H-NMR (300 MHz, $CDCl_3$) δ 9.55 and 9.50 (2 singlets, 1H), 7.40–7.00 (m, 10H), 6.65 and 6.60 (2 sets of d, 1H), 4.85 (d, 1H), 4.65 (q, 1H), 3.20–2.90 (m, 7H), 1.70 and 1.60 (2 singlets, 3H).

Example 89

Synthesis of Compound 106

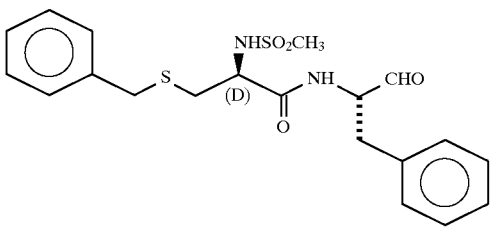

The synthesis of this compound was initiated by following the procedures of Scheme 9, as described above, with the following changes: Boc-(D)-Cys (Bzl), instead of (D)-Phe, was used in the first step; Phe-N(Me)OMe (prepared from Boc-Phe and HN(Me)OMe following the general procedure of Fehrentz et al. Synthesis, 1983, 676, followed by acidic hydrolysis) was used instead of (S)-phenylalaninol in the condensation step. The dipeptide Weinreb amide intermediate was subsequently reduced to the target aldehyde by lithium aluminium hydride, following a general procedure from the above-mentioned reference.

106: Waxy solid; $R_f$ (EtOAc): 0.55; $^1$H-NMR (300 MHz, $CDCl_3$) δ 9.60 (s, 1H), 7.40°–7.10 (m, 10H), 6.90 (d, 1H), 5.50 (d, 1H), 4.75 (q, 1H), 3.95 (q, 1H), 3.70 (s, 2H), 3.15 (m, 2H), 3.00–2.60 (m, 2H), 2.80 (s, 3H),

Example 90

Synthesis of Compounds 107 and 108

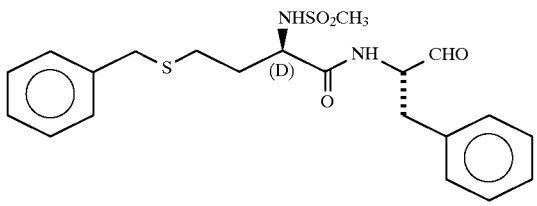

The synthesis of these compounds was initiated by following the procedures of Scheme 8, as described above, with the following changes: (D and L)- homocysteine(Bzl) and methanesulfonyl chloride, instead of (D)-Phe and benzenesulfonyl chloride, were used in the first step; and Phe-N(Me)OMe, instead of (S)-phenylalaninol, was used in the condensation step. The separated diastereomeric dipeptide Weinreb amide intermediates were subsequently reduced to the target aldehydes by lithium aluminium hydride.

Isomer I (107) : White solid, mp 54°–56° C.; $R_f$ (EtOAC) : 0. 60; $^1$H-NMR (300 MHz, $CDCl_3$) δ 9.60 (s, 1H), 7.40–7.05 (m, 10H), 6.55 (d, 1H), 5.30 (d, 1H), 4.75 (q, 1H), 4.05 (m, 1H), 3.65 (m, 2H), 3.20 (dd, 1H), 3.00 (dd, 1H), 2.70 (s, 3H), 2.40 (m, 2H), 1.90 (m, 2H).

Isomer II (108): Waxy solid; $R_f$ (EtOAc): 0. 50; $^1$H-NMR (300 MHz, $CDCl_3$) δ 9.60 (s, 1H), 7.40–7.05 (m, 10H), 6.60 (d, 1H), 5.50 (d, 1H), 4.75 (q, 1H), 4.05 (m, 1H), 3.65 (m, 2H), 3.20 (dd, 1H), 3.00 (dd, 1H), 2.85 (s, 3H), 2.40 (m, 2H), 1.80 (m, 2H).

Example 91

Synthesis of Compound 109

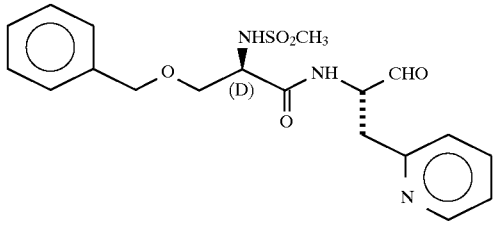

This compound was synthesized following Scheme 8, as described above, except that (D)-Ser(Bzl) instead of (D)-Phe was used in the first step, and (s)-pyridylalaninol, instead of (s)-phenylalaninol, was used in the coupling step.

109: Pale yellow foam; $R_f$ (90% $CH_2Cl_2$-9% $CH_3OH$-1% conc. $NH_4OH$ 0.51; $^1$H-NMR (300 MHz, $CDCl_3$) spectrum was complex, possibly due to the presence of a cyclized form along with the parent molecule; mass spectrum showed M+H-ion peak at m/e 406.

Example 92

Synthesis of Compound 110

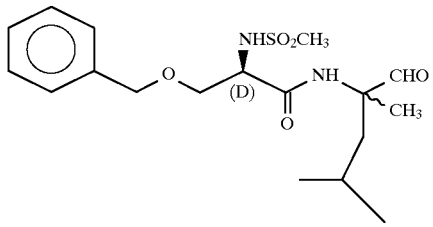

This compound was synthesized following Scheme 8, as described above, except that (D)-Ser(Bzl) instead of (D)-Phe was used in the first step, and racemic α-methylleucinol, instead of (S)-phenylalaninol, was used in the coupling step. Thus the product aldehyde was a diastereomeric mixture, epimeric at $P_1$.

110: White gum; $R_f$ (90% $CH_2Cl_2$-9% $CH_3OH$-1% conc. $NH_4OH$): 0.71 and 0.62 (diastereomers); $^1H$-NMR (300 MHz, $CDCl_3$) δ 9.30 and 9.25 (2 singlets, 1H), 7.45 (d, 1H), 7.40–7.20 (m, 5H), 5.40 (d, 1H), 4.55 (m, 2H), 4.10 (m, 1H), 3.90 (mn, 1H), 3.70 (dd, 1H), 2.95 and 2.90 (2 singlets, 3H), 1.60–1.20 (m, 3H), 1.40 (s, 3H), 0.90 and 0.70 (2 sets of doublet, 6H).

Example 93

Synthesis of Compound 111

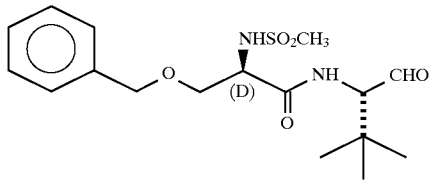

This compound was synthesized following Scheme 8, as described above, except that (D)-Ser(Bzl) instead of (D)-Phe was used in the first step, and (s)-tert-butylglycinol instead of (S)-phenylalaninol was used in the coupling step.

111: White foam; $R_f$ (90% $CH_3Cl_2$-9% $CH_3OH$-1% conc. $NH_4OH$): 0.60; $^1H$-NMR (300 MHz, $CDCl_3$) δ 9.60 (s, 1H), 7.45–7.25 (m, 5H), 7.20 (d, 1H), 5.40 (d, 1H), 4.60 (q, 2H), 4.50 (d, 1H), 4.15 (q, 1H), 3.90 (dd, 1H), 3.75 (dd, 1H), 2.95 (s, 3H), 1.00 (s, 9H).

Example 94

Synthesis of Compound 112

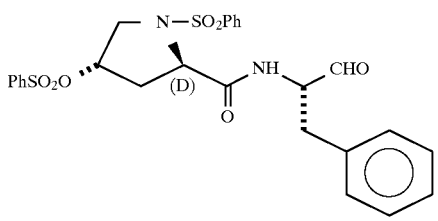

This compound was synthesized following Scheme 8, as described above, except that cis-4-hydroxy-(D)-proline instead of (D)-Phe was used in the first step, and both NH and OH groups were simultaneously sulfonylated.

112: White solid, mp 160°–165° C.; $R_f$ (50% $CH_2Cl_2$-50% EtOAc): 0.61; $^1H$-NMR (300 MHz, $CDCl_3$) δ 9.40 (s, 1H), 7.80–7.25 (m, 16H), 4.90 (t, 1H), 4.55 (q, 1H), 4.25 (d, 1H), 3.55 (dd, 1H), 3.35 (dd, 1H), 3.10 (d, 2H), 2.45 (d, 1H), 1.70 (m, 1H).

Example 95

Synthesis of Compound 113

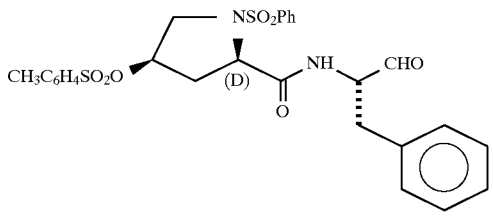

This compound was synthesized following Scheme 9, as described above, except that cis-4-hydroxy-(D)-proline instead of (D)-Phe was used in the first esterification step. Selective phenylsulfonylation of the NH-group, and Mitsunobu displacement (with inversion, in the presence of $Ph_3P$ and diethyl azidocarboxylate; Mitsunobu, O. Synthesis, 1981, 1) of the OH-group with methyl-p-toluenesulfonate gave the bis-sulfonylated intermediate. The remainder of the synthesis followed the route described in Scheme 9.

113: White solid, mp 75°–80 ° C.; $R_f$ (90% $CH_2Cl_2$-9% $CH_3OH$-1% conc. $NH_4OH$): 0.43; $^1H$-NMR (300 MHz, $CDCl_3$) δ 9.60 (s, 1H), 7.80–7.20 (m, 14H), 7.10 (d, 1H), 4.80 (m, 1H), 4.65 (q, 1H), 4.15 (t, 1H), 3.60 (m, 2H), 3.15 (m, 2H), 2.40 (s, 3H), 2.10 (m, 2H).

Example 96

Synthesis of Compound 114

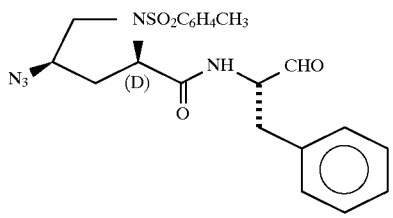

This compound was synthesized following Scheme 8, as described above, with the following changes: cis-4-hydroxy-(D)-proline instead of (D)-Phe was used in the first step; both NH and OH groups were sulfonylated with p-toluenesulfonyl chloride; the disulfonylated derivative was coupled with (S)-phenylalaninol, and the tosyl group in the dipeptide intermediate was displaced in an $S_N2$ fashion by the azido group ($NaN_3$, DMF). Oxidation to generate the product aldehyde was carried out as described.

114: White solid, mp 65°–75° C. (softening to melt); $R_f$ (90% $CH_2Cl_2$-9% $CH_3OH$-1% conc. $NH_4OH$): 0.59; $^1$H-NMR (300 MHz, $CDCl_3$) δ 9.65 (s, 1H), 7.70 (d, 2H), 7.40–7.15 (m, 7H), 4.70 (q, 1H), 4.15 (dd, 1H), 4.00 (m, 1H), 3.60 (dd, 1H), 3.20 (m, 4H), 2.45 (s, 3H), 2.25 (m, 1H), 1.85 (m, 1H).

Example 97

Synthesis of Compound 115

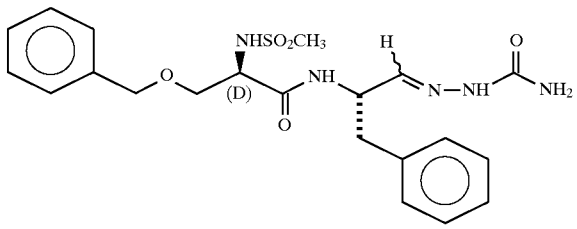

A mixture of Compound 40 (0.20 g, 0.50 mmol), semicarbazide hydrochloride (0.056 g, 0.50 mmol), sodium acetate (0.040 g, 0.50 mmol), ethanol (7 mL) and water (3 mL) was stirred at 0° C. for 1 h, and then at room temperature overnight. The reaction mixture was concentrated, taken into water (15 mL) and extracted into methylene chloride (3×15 mL). The combined organic layer was washed with brine (1×10 mL), dried ($Na_2SO_4$), and concentrated to give a crude product. It was purified by flash column chromatography (5% MeOH in methylene chloride) to give 0.048 g of Compound 115.

115: White solid, mp 168°–173° C. ; $R_f$ (90% $CH_2Cl_2$-10% $CH_3OH$): 0.44; $^1$H-NMR (300 MHz, $CDCl_3$) δ 8.65 (s, 1H), 7.45–7.10 (m, 11H), 7.15 (d, 2H), 7.00 (d, 1H), 6.40 (d, 1H), 4.80 (m, 1H), 4.50 (q, 2H), 4.10 (m, 1H), 3.80 (dd, 1H), 3.70 (dd, 1H), 3.00 (m, 2H), 2.90 (s, 3H).

Example 98

Synthesis of Compound 116

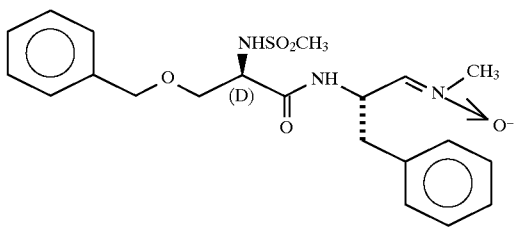

This compound was generated following the same synthetic protocol, as described above, for the synthesis of Compound 115, Example 97, except that N-methylhydroxylamine hydrochloride instead of semicarbazide hydrochloride was used in the synthesis.

116: White solid, mp 148°–153° C.(softening to melt); $R_f$ (90% $CH_2Cl_2$-9% $CH_3OH$-1% conc. $NH_4OH$): 0.53; $^1$H-NMR (300 MHz, $CDCl_3$) δ 8.05 (d, 1H), 7.40–7.10 (m, 10H), 6.70 (d, 1H), 5.25 (d, 1H), 4.95 (m, 1H), 4.50 (dd, 2H), 4.05 (m, 1H), 3.80 (dd, 1H), 3.65 (s, 3H), 3.60 (m, 1H), 3.20 (dd, 1H), 3.10 (dd, 1H), 2.90 (s, 3H).

Example 99

Synthesis of Compound 117

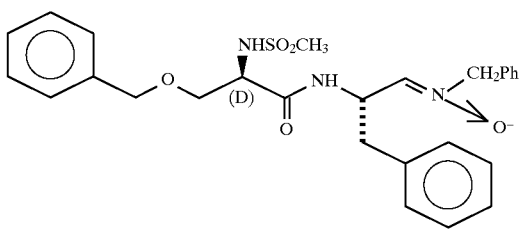

This compound was generated following the same synthetic protocol, as described above, for the synthesis of Compound 115, except that N-benzylhydroxylamine hydrochloride instead of semicarbazide hydrochloride was used in the synthesis.

117: White solid, mp 154°–156° C.; $R_f$ (90% $CH_2Cl_2$-9% $CH_3OH$-1% conc. $NH_4OH$): 0.56; $^1$H-NMR (300 MHz, $CDCl_3$) δ 8.10 (d, 1H), 7.40–7.20 (m, 13H), 7.00 (m, 2H), 6.65 (d, 1H), 5.30 (d, 1H), 4.95 (m, 1H), 4.80 (s, 2H), 4.50 (s, 2H), 4.00 (m, 1H), 3.80 (dd, 1H), 3.60 (dd, 1H), 3.15 (dd, 1H), 3.00 (dd, 1H), 2.90 (s, 3H).

Example 100

Synthesis of Compound 118

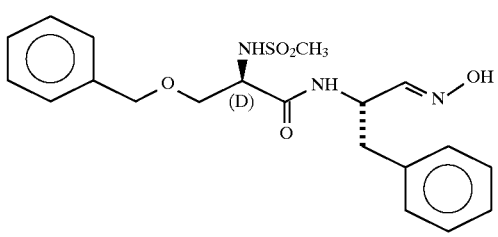

This compound was synthesized by coupling Compound 40 and hydroxylamine hydrochloride, in the presence of pyridine and ethanol (without sodium acetate and water), following the general synthetic protocol for the synthesis of Compound 115.

118: White foam; $R_f$ (90% CH$_2$Cl$_2$-9% CH$_3$OH-1% conc. NH$_4$OH): 0.51; $^1$H-NMR (300 MHz, CDCl$_3$) δ 7.40–7.20 (m, 10H), 7.10 (t, 2H), 5.35 (d, 1H), 4.85 (m, 1H), 4,45 (dd, 2H), 4.05 (m, 1H), 3.85 (dd, 1H), 3.60 (dd, 1H), 3.00 (d, 2H), 2.85 (s, 3H), 1.55 (broad, 1H).

Example 101

Synthesis of Compound 119

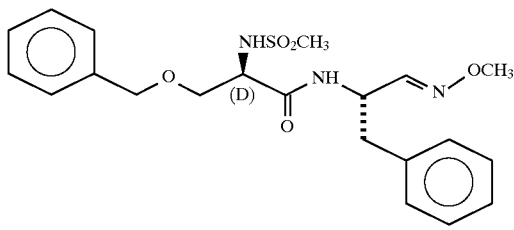

This compound was synthesized by coupling Compound 40 and methoxylamine hydrochloride, in the presence of pyridine and ethanol (without sodium acetate and water), following the general synthetic protocol for the synthesis of Compound 115.

119: White gum; $R_f$ (90% CH$_2$Cl$_2$-9% CH$_3$OH-1% conc. NH$_4$OH): 0.86; $^1$H-NMR (300 MHz, CDCl$_3$) δ 7.40–7.10 (m, 12H), 5.20 (2 sets of d, 1H), 4.85 (m, 1H), 4.45 (q, 2H), 4.00 (m, 1H), 3.90 and 3.75 (2 singlets, 3H), 3.80 (m, 1H), 3.60 (m, 1H), 3.00 (d, 2H), 2.85 and 2.80 (2 singlets, 3H).

Example 102

Synthesis of Compound 120

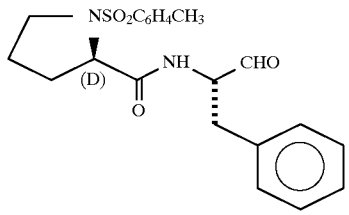

This compound was synthesized following Scheme 8, as described above, except that (D)-Pro and p-toluenesulfonyl chloride, instead of (D)-Phe and methanesulfonyl chloride, were used in the first step.

120: White solid; mp 55°–60° C.(softening to melt); $R_f$ (90% CH$_2$Cl$_2$-9% CH$_3$OH-1% conc. NH$_4$OH): 0.42; $^1$H-NMR (300 MHz, CDCl$_3$) δ 9.60 (s, 1H), 7.70 (d, 2H), 7.30 (m, 7H), 4.65 (q, 1H), 4.10 (dd, 1H), 3.45 (m, 1H), 3.15 (m, 4H), 2.40 (s, 3H), 2.05 (m, 1H), 1.80–1.50 (m, 3H).

Example 103

Synthesis of Compound 121

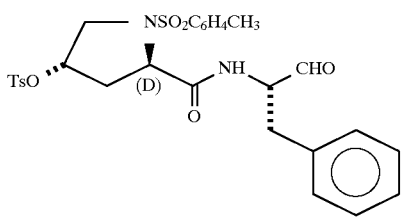

This compound was synthesized following Scheme 8, as described above, except that cis-4-hydroxy-(D)-proline instead of (D)-Phe was used in the first step, and both NH and OH groups were sulfonylated with p-toluenesulfonyl chloride.

121: White solid; mp 160°–165° C.(softening to melt); $R_f$ (EtOAc: CH$_2$Cl$_2$ 2 :1): 0.65; $^1$H-NMR (300 MHz, CDCl$_3$) δ 9.35 (s, 1H), 7.65 (t, 4H), 7.45–7.20 (m, 10H), 4.85 (m, 1H), 4.50 (q, 1H), 4.20 (d, 1H), 3.65 (d, 1H), 3.30 (dd, 1H), 3.10 (d, 2H), 2.45 and 2.40 (2 singlets, 6H), 1.65 (m, 2H).

Example 104

Synthesis of Compound 122

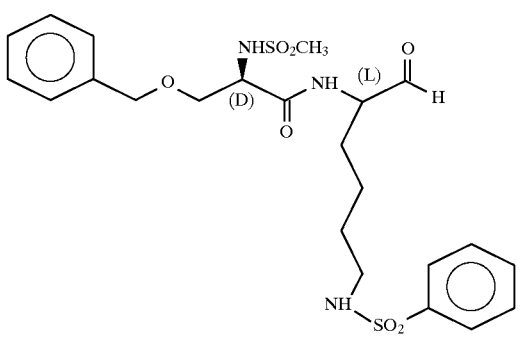

The synthesis of this compound was initiated by coupling (EDCI, HOBt, DMF) methanesulfonyl-(D)-Ser(Bzl) and (L)-Lys(Boc)-OMe hydrochloride salt; NHBoc was converted (90% TFA, CH$_2$Cl$_2$) to free NH$_2$ which, in turn, was converted to NHSO$_2$Ph (PhSO$_2$Cl, NMM, THF- CH$_2$Cl$_2$ ). Finally, the COOMe group was converted to CHO, following the procedure described in Scheme 7. The final product showed that some racemization had occurred.

122: White solid; mp 50°–55° C. (softening to melt); $R_f$ (90% CH$_2$Cl$_2$-9% CH$_3$OH-1% conc. NH$_4$OH): 0.41; $^1$H-NMR (300 MHz, CDCl$_3$) δ 9.55 and 9.50 (2 singlets, 1:9, 1H), 7.85 (d, 2H), 7.55 (m, 3H), 7.30 (m, 5H), 5.60 (d, 1H), 4.90 (broad t, 1H), 4.50 (m, 4H), 4.20 (m, 1H), 3.90 (dd, 1H), 3.80 (dd, 1H), 3.00 and 2.95 (2 singlets, 9:1, 3H), 2.85 (m, 2H), 1.95–1.30 (m, 6H).

Example 105

Synthesis of Compound 123

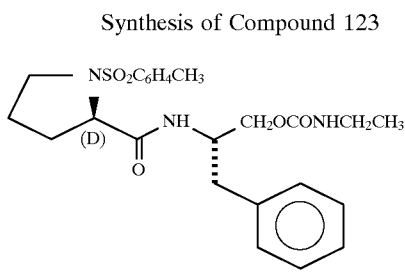

The synthesis of this compound was initiated following Scheme 8, as described above, except that (D)-Pro and p-toluenesulfonyl chloride, instead of (D)-Phe and methanesulfonyl chloride, were used in the first step. The intermediate dipeptide alcohol was treated with ethyl isocyanate in the presence of triethylamine to generate the final product.

123: White solid; mp 45°–55° C. (softening to melt); $R_f$ (EtOAc: $CH_2Cl_2$ 2:1): 0.57; $^1$H-NMR (300 MHz, $CDCl_3$) δ 7.70 (d, 2H), 7.30 (m, 7H), 4.85 (broad, 1H), 4.30 (m, 1H), 4.10 (m, 3H), 3.50 (m, 1H), 3.25 (mn, 2H), 3.15 (m, 1H), 3.00 (dd, 1H), 2.85 (dd, 1H), 2.45 (s, 3H), 2.10 (m, 1H), 1.80–1.40 (m, 4H), 1.15 (t, 3H).

Example 106

Synthesis of Compound 124

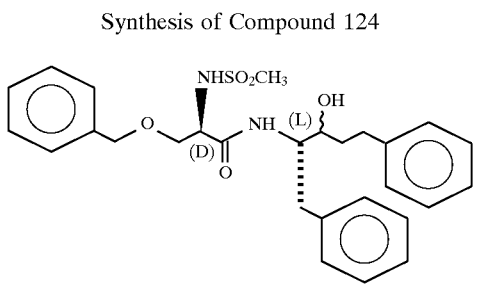

This compound was synthesized by coupling (EDCI, HOBt, DMF) methanesulfonyl-(D)-Ser(Bzl) and 4-(S)-amino-3(R,S)-hydroxy-1,5-biphenylpentane (prepared by coupling Boc-Phe-H and benzylmagnesium chloride, followed by deprotection of the Boc group).

124: White solid; mp 108°–110° C.; $R_f$ (90% $CH_2Cl_2$-10%EtOAc): 0.27; $^1$H-NMR (300 MHz, $CDCl_3$) δ 7.40–7.05 (m, 15H), 6.90 (d, 1H), 5.25 (d, 1H), 4.50 (q, 2H), 4.20 (q, 1H), 4.00 (q, 1H), 3.80 (dd, 1H), 3.65 (m, 1H), 3.50 (m, 2H), 2.85 (m, 4H), 2.65 (q, 2H), 2.00 (d, 1H), 1.70 (q, 2H).

Example 107

Synthesis of Compound 125

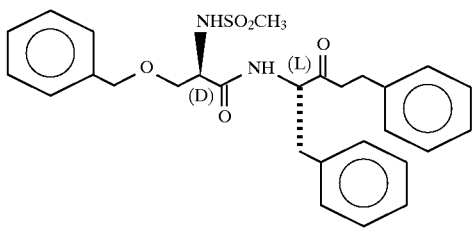

This compound was synthesized by Dess-Martin oxidation of Compound 124 prepared in Example 106.

125: White solid; mp 112°–113° C.; $R_f$ (90% $CH_2Cl_2$-10% EtOAc): 0.42; $^1$H-NMR (300 MHz, $CDCl_3$) δ 7.40–7.10 (m, 14H), 7.00 (m, 2H), 5.30 (d, 1H), 4.75 (q, 1H), 4.45 (q, 2H), 4.00 (q, 1H), 3.80 (dd, 1H), 3.55 (dd, 1H), 3.05 (dd, 1H), 3.00–2.75 (m, 3H), 2.80 (s, 3H), 2.75 (m 2H).

Example 108

Synthesis of Compound 126

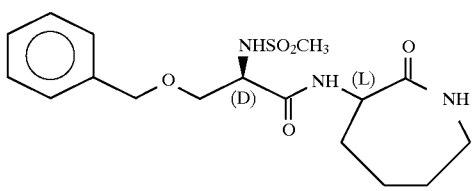

This compound was synthesized by coupling (EDCI, HOBt, DMF) methanesulfonyl-(D)-Ser(Bzl) and (L)-α-amino-ε-caprolactam.

126: White solid; mp 45°–50° C. (softening to melt); $R_f$ (90% $CH_2Cl_2$-9% $CH_3OH$-1% conc. $NH_4OH$): 0.55; $^1$H-NMR (300 MHz, $CDCl_3$) δ 7.85 (d, 1H), 7.30 9 m, 5H), 6.35 (broad t, 1H), 5.80 (d, 1H), 4.55 (m, 3H), 4.25 (m, 1H), 3.80 (dd, 1H), 3.70 (dd, 1H), 3.20 (m, 2H), 3.00 (s, 3H), 2.00 (m, 2H), 1.80 (m, 2H), 1.40 (m, 2H).

Example 109

Synthesis of Compound 127

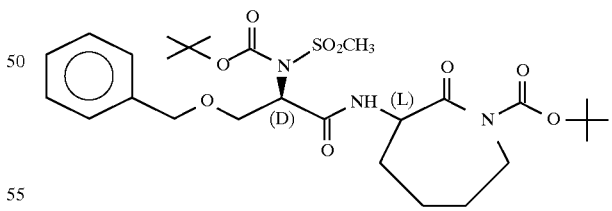

This compound was synthesized by treatment of Compound 126 prepared in Example 108 with $Boc_2O$ in the presence of $Et_3N$ and 4-dimethylaminopyridine, following the procedure of Grieco et al. *J. Org. Chem.* 1983, 48, 2426.

127: White solid; mp 55°–60° C.(softening to melt); $R_f$ (90% $CH_2Cl_2$-9% $CH_3OH$-1% conc. $NH_4OH$): 0.90; $^1$H-NMR (300 MHz, $CDCl_3$) δ 8.15 (d, 1H), 7.50–7.20 (m, 5H), 5.05 (q, 1H), 4.70 (m, 2H), 4.30 (m, 2H), 3.75 (q, 1H), 3.40 (s, 3H), 3.30 (m, 2H), 2.05–1.40 (a series of m, 6H), 1.55 (s, 9H), 1.45 (s, 9H).

Example 110

Synthesis of Compound 128

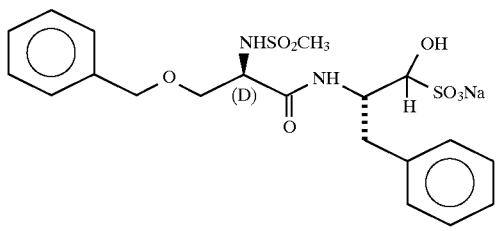

This compound was synthesized by reaction of Compound 40 with sodium bisulfite in a biphasic system of methylene chloride and water.

128: White solid (hygroscopic); $^1$H-NMR (300 MHz, DMSO-$d_6$) δ 8.25 and 7.85 (2 sets of d, 1H), 7.40–7.00 (m, 10H), 5.75 and 5.60 (2 sets of d, 1H), 4.50–4.20 (m, 4H), 4.00 (m, 2H), 3.80 (m, 1H), 3.50–3.20 (m, 3H), 2.80 and 2.75 (2 singlets, 3H). Anal. calcd. for $C_{20}H_{25}N_2O_8S_2Na$ $0.3NaHSO_3$: C, 44.51; H, 4.67, N, 5.19. Found: C, 44.62; H, 4.75; N, 5.20.

Example 111

Synthesis of Compound 129

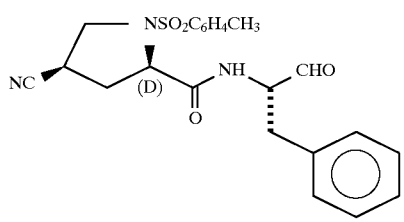

This compound was synthesized following the procedures of Scheme 8, as described above, except that cis-4-hydroxy-(D)-proline instead of (D)-Phe was used in the first step and both NH and OH groups were sulfonylated with p-toluenesulfonyl chloride. The disulfonylated derivative was coupled with (S)-phenylalaninol and the OTs group in the dipeptide intermediate was displaced in an $SN^2$ fashion by the cyano group (KCN, DMSO, 65° C., overnight). Finally, oxidation of the alcohol moiety generated the target aldehyde, Compound 129.

129: White solid; mp 65°–75° C. (softening to melt); $R_f$ (90% $CH_2Cl_2$-9% $CH_3OH$-1% conc. $NH_4OH$): 0.44; $^1$H-NMR (300 MHz, CDCl$_3$) δ 9.60 (s, 1H), 7.70 (d, 2H), 7.40–7.15 (m, 8H), 4.70 (q, 1H), 4.20 (d, 1H), 3.75 (dd, 1H), 3.30–3.10 (mn, 3H), 3.00 (m, 1H), 2.55 (dd, 1H), 2.45 (s, 3H), 1.70 (m, 1H).

Example 112

Synthesis of Compound 130

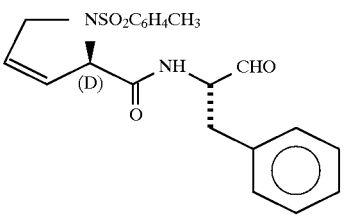

The precursor alcohol for this aldehyde was isolated as a minor product from the cyanation step Example 111. Subsequent Dess-Martin oxidation of the alcohol generated the target aldehyde, Compound 130.

130: White solid; mp 55°–65° C.(softening to melt); $R_f$ (90% $CH_2Cl_2$-9% $CH_3OH$-1% conc. $NH_4OH$): 0.52; $^1$H-NMR (300 MHz, CDCl$_3$) δ 9.60 (s, 1H), 7.70 (d, 2H), 7.40–7.20 (m, 8H), 5.70 (m, 2H), 4.85 (m, 1H), 4.60 (q, 1H), 4.15 (m, 2H), 3.20 (m, 2H), 2.45 (s, 3H).

Example 113

Synthesis of Compound 131

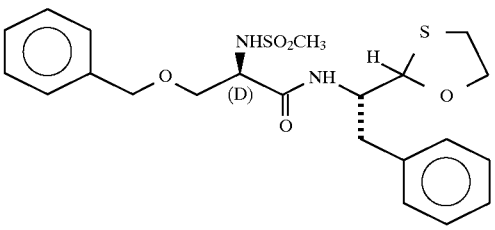

This compound was synthesized by coupling Compound 40 with 2-mercaptoethanol in the presence of $ZnCl_2$ and $Na_2SO_4$ in THF-$Et_2O$.

131: White gum; $R_f$ (90% $CH_2Cl_2$-9% $CH_3OH$-1% conc. $NH_4OH$): 0.31; $^1$H-NMR (300 MHz, CDCl$_3$) δ 7.40–7.10 (m, 10H), 5.60 (d, 1H), 4.60 (m, 1H), 4.50 (q, 2H), 4.15 (d, 1H), 4.00 (broad d, 1H), 3.80 (m, 2H), 3.70 (t, 2H), 3.50 (dd, 1H), 3.20 (dd, 1H), 3.00–2.70 (m, 4H), 2.85 (s, 3H).

Example 114

Synthesis of Compound 132

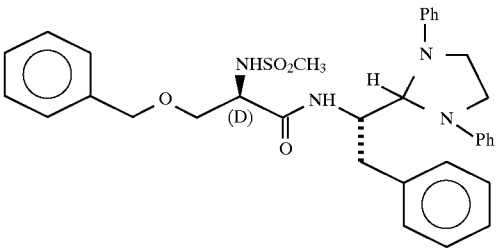

This compound was synthesized by coupling Compound 40 with 1,2-dianilinoethane.

132: White solid; mp 138°–140° C.; $^1$H-NMR (300 MHz, CDCl$_3$) δ 7.40–7.10 and 6.90–6.70 (2 sets of m, 21H), 5.75 (d, 1H), 4.75 (d, 2H), 4.30 (s, 2H), 3.90 (q, 1H), 3.75 (m, 3H), 3.45 (m, 2H), 3.35 (dd, 1H), 3.05 (dd, 1H), 2.70 (s, 3H), 2.50 (t, 1H).

Example 115

Synthesis of Compound 133

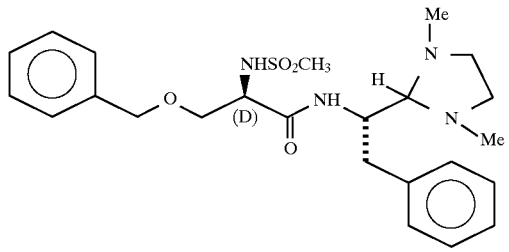

This compound was synthesized by coupling Compound 40 with N, N'-dimethylethylenediamine.

133: White gum; $^1$H-NMR (300 MHz, CDCl$_3$) δ 7.40–7.10 (m, 10H), 5.25–4.90 (broad, 3H), 4.30 (q, 1H), 4.00 (t, 1H), 3.75 (dd, 1H), 3.50 (m, 4H), 3.10–2.70 (m, 5H), 2.85 (s, 3H), 2.50 (d, 6H).

Example 116

Synthesis of Compound 134

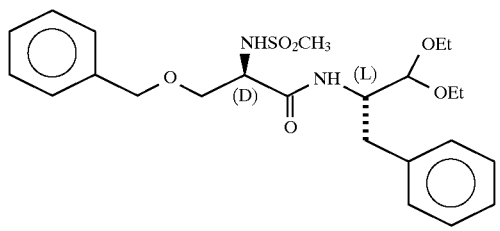

This compound was synthesized by coupling methanesulfonyl-(D)-Ser(Bzl) and Phe-H diethyl acetal; the final product showed that some racemization had occurred.

134: White gum; R$_f$(EtOAc-hexane: 1:1): 0.30; $^1$H-NMR (300 MHz, CDCl$_3$) δ 7.35–7.00 (m, 11H), 6.80 (d, 1H), 5.15 (t, 1H), 4.50–4.25 (m, 4H), 3.90 (m, 1H), 3.70–3.30 (m, 5H), 2.90 (m, 1H), 2.80 and 2.70 (2 singlets, 3H), 2.65 (m, 1H), 1.10 (m, 6H).

Example 117

Synthesis of Compound 135

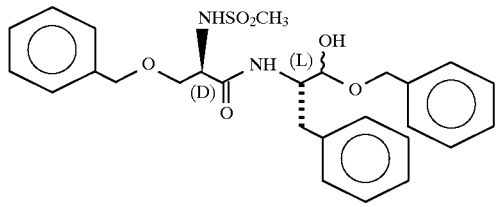

This compound was synthesized by stirring overnight at room temperature Compound 40 with excess benzyl alcohol. Excess alcohol was removed by repeated washing with hexane, and the residue was triturated with EtOAc-hexane to give Compound 135 as a solid material, mp 87°–89° C., which was immediately subjected to biological testing. $^1$H-NMR (300 MHz, DMSO-d$_6$) spectrum of an aliquot showed the absence of aldehyde moiety in the molecule.

Example 118

Inhibition and Rate of Inactivation of Cysteine Protease Activity

To evaluate inhibitory activity, stock solutions (40 times concentrated) of exemplary compounds of the invention were prepared in 100% anhydrous DMSO and 5 μL of each inhibitor preparation were aliquoted into each of three wells of a 96-well plate. Recombinant human calpain I, prepared by the method of Meyer et al. (Biochem. J. 314: 511–519 (1996)), was diluted into assay buffer (i.e., 50 mM Tris, 50 mM NaCl, 1 mM EDTA, 1 mM EGTA, and 5 mM-mercaptoethanol, pH 7.5 including 0.2 mM Succ-Leu-TyrMNA) and 175 μL aliquoted into the same wells containing the independent inhibitor stocks as well as to positive control wells containing 5 μL DMSO, but no compound. To start the reaction, 20 μL of 50 mM CaCl$_2$ in assay buffer was added to all wells of the plate, excepting three, which were used as background signal baseline controls. Substrate hydrolysis was monitored every 5 minutes for a total of 30 minutes. Substrate hydrolysis in the absence of inhibitor was linear for up to 15 minutes.

Inhibition of calpain I activity was calculated as the percent decrease in the rate of substrate hydrolysis in the presence of inhibitor (V$_I$) relative to the rate in its absence (V$_O$). Comparison between V$_O$ and V$_I$ was made within the linear range for substrate hydrolysis. For screening, compounds were tested at 10, 1.0, and 0.1 μM. Compounds having 50% inhibition at 10 μM were considered active. The IC50s of inhibitors (concentration yielding 50% inhibition) were determined from the percent decrease in the rates of substrate hydrolysis in the presence of five to seven different concentrations of the test compound. The results were plotted as % inhibition versus log inhibitor concentration and the IC50 was calculated from linear regression of the data. Apparent second order rate constants were determined from analysis of reaction progress curves under pseudo-first order conditions. Each determination represents the means of three or more independent single cuvette analyses continually monitored via a Perkin-Elmer LS50B spectrofluorimeter. The rate of inhibition of hydrolysis was obtained by fitting the curve to the exponential equation (1):

$$y = Ae^{-(K_{obs} \cdot t)} + B \quad (1)$$

where y is the product formed at time t. K$_{obs}$ is the pseudo-first order rate constant for inactivation. A and B are constants. A, the amplitude of the reaction, is given by [P$_O$-P$_∞$] and B (=P$_∞$) is the maximal product formed when the reaction is complete. The apparent second order rate constant k$_{app}$ was determined as K$_{obs}$/[I]. This was corrected for the presence of substrate to give the second order rate constant k$_2$ according to equation (2):

$$k_2 = k_{app}(1 + [S]/K_m) \quad (2)$$

To demonstrate activity against two other cysteine proteases, cathepsin B (Calbiochem, catalog # 219364) and cathepsin L (Calbiochem, catalog # 219402), assays were performed substantially the same as outlined above except that the cathepsin B and cathepsin L were diluted into a different assay buffer consisting of 50 mM sodium acetate (pH 6.0)/1 mM EDTA/1 mM dithiothreitol and the substrate used was Cbz-Phe-Arg-AMC (Bachem catalog # I-1160; 0.1 mM for cathepsin B; 0.006 mM for cathepsin L). Additionally, the order of reagents added to the plate was altered because both enzymes are constitutively active. Following inhibitor addition to the plates, appropriate 2× concentrated stock dilutions of the enzyme preparations were made in assay buffer and 100 μl added to each well. The assay was initiated by addition of 100 μl of 2× concentrated stock dilution of substrate in assay buffer. Substrate hydrolysis was monitored using a Fluoroskan II (ex=390 nm; em=460 nm).

Results are presented in Tables II and III.

Example 119

Inhibition of Serine Protease Activity

To demonstrate activity against the serine protease α-chymotrypsin (Sigma Chem. Co. catalog # C-3142) the protocol of Example 118 was followed except that the enzyme was diluted into assay buffer consisting of 50 mM Hepes (pH 7.5)/0.5M NaCl and the final substrate concentration used was 0.03 mM Succ-Ala-Ala-Pro-Phe-AMC (Bachem catalog # I-1465). Additionally, because α-chymotrypsin is not a calcium sensitive enzyme and is constitutively active, following addition of inhibitor stocks to the 96 well plates, 100 μl of a 2-fold concentrated stock of enzyme in dilution buffer was first added and the reaction started by addition of 100 μl of a 2-fold concentrated stock of substrate in assay buffer. Substrate hydrolysis was monitored every 5 minutes up to 30 minutes using a Fluoroskan II (em=390 nm ex=460 nm). Results, expressed as inhibition of α-chymotrypsin at 10 μM, are presented in Tables II and III.

Inhibition of thrombin (Sigma Chem. Co. catalog # T-7009) was evaluated as described for chymotrypsin except that the assay was performed in 50 mM Tris, 10 mM $CaCl_2$, pH 7.5 and the substrate was 25 μM Bz-Phe-Val-Arg-AMC (Bachem catalog # I-1080). Results are presented in Tables II and III.

TABLE II

| Cpd | Chemical Name | Calpain IC50 (nM) | Calpain Inacti-vation Rates ($M^{-1}/S^{-1}$) | Cat B IC50 (nM) | Cat L IC50 (nM) | Thrombin % I @ 10 uM | Chymotrypsin % I @ 10 uM |
|---|---|---|---|---|---|---|---|
| 8 | (R)-2-THIQ-C(=O)CH$_2$CH(NHBoc)C(=O)-Phe—H | ≈20,000 | — | | 24,000 | 0 | 32 |
| 9 | 2-THIQ-C(=O)CH$_2$CH(NHC(=O)CH$_3$)C(=O)-Phe—H | 83 | — | 11,000 | 2,000 | 0 | 2 |
| 25 | BnS—CH$_2$CH(NHC(=O)CH$_3$)C(=O)-Phe—H | 26 | — | 5,000 | 48 | 0 | 3 |
| 14 | 2-THIQ-C(=O)CH$_2$CH(NHS(=O)$_2$CH$_3$)C(=O)-Phe—H | 20 | — | | 145 | 56 | 0 | 11 |
| 33 | BnS—CH$_2$CH(NHS(=O)$_2$CH$_3$)C(=O)-Phe—CH$_2$F | — | 26,600 | | | 0 | 14 |
| 20 | THIQ-2-C(=O)CH$_2$CH(NHS(=O)$_2$CH$_3$)C(=O)-Phe—CH$_2$F | — | 2,800 | | 1,800 | 0 | 7 |
| 34 | BnO—CH$_2$CH(NHS(=O)$_2$CH$_3$)C(=O)-Phe—CH$_2$F | — | 21,000 | | 1,800 | 0 | 14 |
| 40 | BnO—CH$_2$CH(NHS(=O)$_2$CH$_3$)C(=O)-Phe—H | 11 | | 42 | 9 | 0 | 23 |

TABLE III

| Cpd. | Calpain % I @ 0.1 uM | Calpain IC50 (nM) | Cat B % I @ 1 uM | Cat B IC50 (nM) | Cat L % I @ 1 uM | Thrombin % I @ 10 uM | Chymotrypsin % I @ 10 uM |
|---|---|---|---|---|---|---|---|
| 41 | 67 | 50 | 42 | | | 100 | 2 | 0 |
| 42 | 87 | 17 | 90 | | | 96 | 7 | 14 |
| 43 | 95 | 12 | 98 | 58 | | 68 | 0 | 3 |
| 44 | 29 | 280 | 62 | | | 100 | 7 | 0 |
| 45 | 55 | 85 | 100 | | | 100 | 7 | 5 |
| 46 | 90 | 24 | 100 | | | 100 | 15 | 6 |
| 47 | 91 | 9 | 96 | | | 98 | 6 | 2 |
| 48 | 87 | 31 | 99 | 11 | | 100 | 3 | 0 |
| 49 | 75 | 27 | 99 | | | 100 | 4 | 1 |
| 50 | 95 | 12 | 99 | | | 98 | 9 | 15 |
| 51 | 92 | 32 | 100 | 14 | | 100 | 21 | 3 |
| 52 | 93 | 28 | 100 | 4 | 100 | 10 | 0 |
| 53 | 25 | 72 | 98 | | 100 | 0 | 0 |
| 54 | 95 | 13 | 100 | | 100 | 4 | 3 |
| 55 | 87 | 25 | 90 | | 100 | 2 | 12 |
| 59 | 86 | 20 | 100 | 5 | 100 | 0 | 4 |
| 60 | 74 | 33 | 97 | | 100 | 0 | 0 |
| 61 | 83 | 22 | 100 | | 100 | 0 | 0 |
| 62 | 71 | 39 | 85 | | 89 | 0 | 4 |
| 63 | 41 | 75 | | | 100 | 1 | 40 |
| 64 | 68 | | 87 | | 100 | 0 | 10 |
| 70 | 85 | 16 | 90 | | 100 | 0 | 12 |
| 71 | 92 | 31 | 100 | | 100 | 11 | 5 |
| 72 | 91 | 14 | 100 | | 100 | 13 | 7 |
| 73 | 95 | 14 | 100 | | 100 | 12 | 16 |
| 74 | 83 | 33 | 100 | | 100 | 6 | 13 |
| 75 | 91 | 20 | 100 | | 99 | 10 | 2 |
| 76 | 88 | 13 | 79 | 250 | 90 | 1 | 30 |
| 77 | 91 | 14 | 90 | | 93 | 0 | 0 |
| 78 | 94 | 12 | 100 | 6 | 100 | 0 | 0 |
| 79 | 47 | 1000 | 99 | | 93 | 1 | 8 |
| 80 | 90 | 15 | 99 | 46 | 100 | 4 | 8 |
| 81 | 18 | 180 | 73 | | 100 | 0 | 2 |
| 82 | 4 | | 60 | | 93 | 6 | 8 |
| 83 | 37 | 520 | 62 | | 53 | 7 | 0 |
| 84 | 2 | | 22 | | 93 | 0 | 0 |
| 85 | 44 | 110 | 44 | | 89 | 0 | 6 |
| 86 | 72 | 40 | 78 | | 100 | 0 | 8 |
| 87 | 23 | 95 | 86 | | 96 | | |
| 88 | 40 | 93 | 88 | | 91 | 5 | 0 |
| 89 | 82 | 15 | 100 | | 97 | 0 | 4 |
| 90 | 99 | 5 | 100 | | 99 | 0 | 0 |
| 91 | 30 | | 68 | | 100 | 0 | 53 |
| 92 | 100 | 4 | 100 | | 100 | 0 | 0 |
| 93 | 95 | 9 | 99 | | 100 | 0 | 0 |
| 94 | 14 | | 0 | | 93 | 0 | 1 |
| 95 | 17 | 278 | 38 | | 100 | 1 | 0 |
| 96 | 49 | 174 | 90 | | 100 | 0 | 14 |
| 97 | 79 | 37 | 89 | | 100 | 4 | 25 |
| 98 | 96 | 8 | 98 | 16 | 100 | 16 | 49 |
| 99 | 66 | 62 | 96 | | 100 | 0 | 13 |
| 100 | 96 | 15 | 97 | 31 | 100 | 0 | 0 |
| 101 | 84 | 53 | 46 | | 100 | 0 | 2 |
| 102 | 63 | 72 | 69 | | 73 | 7 | 0 |

TABLE III-continued

| Cpd. | Calpain %I @ 0.1 uM | Calpain IC50 (nM) | Cat B %I @ 1 uM | Cat B IC50 (nM) | Cat L %I @ 1 uM | Thrombin %I @ 10 uM | Chymotrypsin %I @ 10 uM |
|---|---|---|---|---|---|---|---|
| 103 | 37 | 71 | 40 | | 56 | 3 | 26 |
| 104 | 45 | 93 | 86 | | 97 | 7 | 6 |
| 105 | 9 | | 45 | | 71 | 0 | 10 |
| 106 | 95 | 8 | 92 | | 100 | 7 | 16 |
| 107 | 63 | 67 | 97 | | 100 | 2 | 11 |
| 108 | 83 | 25 | 96 | | 100 | 0 | 0 |
| 109 | 59 | 40 | 70 | | 98 | 0 | 0 |
| 110 | 10 | | 12 | | 83 | 0 | 0 |
| 111 | 27 | | 10 | | 91 | 0 | 16 |
| 112 | 7 | | 25 | | 100 | 0 | 9 |
| 113 | 11 | | 47 | | 94 | 0 | 0 |
| 114 | 85 | 28 | 24 | | 100 | 3 | 9 |
| 115 | 0 | | 47 | | 94 | 0 | 0 |
| 116 | 4 | | 96 | | 100 | 0 | 0 |
| 117 | 21 | | 95 | | 100 | 0 | 0 |
| 118 | 31 | | 33 | | 99 | 0 | 8 |
| 119 | 19 | | 68 | | 98 | 0 | 3 |
| 128 | 89 | 8 | 99 | | 100 | 0 | 1 |
| 120 | 87 | 14 | 50 | | 65 | 0 | 12 |
| 121 | 28 | | 83 | | 17 | 3 | 18 |
| 122 | 98 | 3 | 100 | | 100 | 0 | 13 |
| 123 | 7 | | 16 | | 14 | 0 | 2 |
| 124 | 20 | | 27 | | 17 | 2 | 0 |
| 125 | 0 | | 47 | | 39 | 4 | 0 |
| 126 | 5 | | 2 | | 16 | 0 | 6 |
| 127 | 6 | | 36 | | 7 | 0 | 1 |
| 129 | 73 | 28 | 64 | | 100 | 1 | 6 |
| 130 | 90 | 10 | 62 | | 97 | 9 | 0 |
| 131 | 6 | | 21 | | 55 | 11 | 0 |
| 132 | 63 | | 78 | | 100 | 0 | 0 |
| 133 | 93 | 13 | 100 | | 100 | 0 | 1 |
| 134 | 0 | | 19 | | 98 | 0 | 10 |
| 135 | 91 | 11 | 98 | | 100 | 0 | 4 |

Example 120

Suppression by Compound 40 of Spectrin Breakdown in Gerbil Global Ischemia Model Gerbils were anesthetized using 4% isoflurane volatilized using a gas mixture consisting of 30% $O_2$ and 70% $N_2$. After the induction of anesthesia, a preferred compound of the invention, compound 40 (Example 34), was administered either immediately before the induction of ischemia and 24 hours after the initiation of reperfusion (FIG. 2), or three hours after the initiation of reperfusion and 24 hours after the initiation of reperfusion (FIG. 3). To induce ischemia, the common carotid arteries were exposed and occluded bilaterally for 7 minutes. Gerbil core temperature was carefully regulated at 38° C. by a thermostatically controlled heat lamp. Reperfusion was initiated by the release of the arterial occlusion, whereupon anesthesia was terminated so that the gerbils began to breath room air. The neck incision was closed, and the gerbils were returned to the incubator for one hour to maintain their core temperature. At 1 hour of reperfusion, anesthesia was induced by inhalation of $CO_2$ and the gerbils were sacrificed. The CA1 hippocampal sector was dissected using a hole punch (0.3 mm), and spectrin breakdown products (BDP) were determined by Western Blotting. Spectrin breakdown was quantified by image analysis, and percent inhibition was calculated by integrated optical density. Calpain activation and elevated levels of spectrin breakdown products have been associated with several neurodegenerative conditions including those caused by ischemia. Detection of calpain activation by detection of calpain activated spectrin breakdown is described in detail in U.S. Pat. No. 5,536,639, the disclosures of which are hereby incorporated y reference in their entirety.

To quantify histopathological damage, the gerbils were returned to their home cages after one hour reperfusion in the incubator and then sacrificed, as described above, four days later. The brains were rapidly removed, frozen on dry ice, and then sectioned using a cryostat. Twenty micron sections were stained with thionin, and surviving neurons in the hippocampal CA1 sector were counted using computer assisted image analysis.

In order to facilitate salvation and administration, Compound 40 was formulated for use as an emulsion. The emulsion was prepared by mixing 1,2-dimyristoyl-sn-glycero-3-phosphocholine (Sygena, Inc., Cambribge, Mass.), cholesterol (Genzyme Corp., Cambribge, Mass.), and Compound 40 in a ratio of 4:2:1 parts by weight. Chloroform (1 ml) and ethanol (0.5 ml) were added, and the contents were mixed until all solutes were dissolved in the organic phase. Volatile solvents were then evaporated with a stream of nitrogen. Phosphate buffered saline (50° C.) was added to the residual mixture in an amount to give a concentration of compound 40 of 6 mg/ml. The components of the residue were mixed using a Pasteur pipet to give a coarse emulsion, and a fine emulsion was obtained using a high pressure emulsifier.

Analysis of spectrin breakdown in the CA1 hippocampal sectors of vehicle-treated control gerbils and gerbils treated with Compound 40 showed a statistically significant suppression of spectrin breakdown in gerbils treated with Compound 40 (p<0.0001; FIG. 1).

Figure 2:
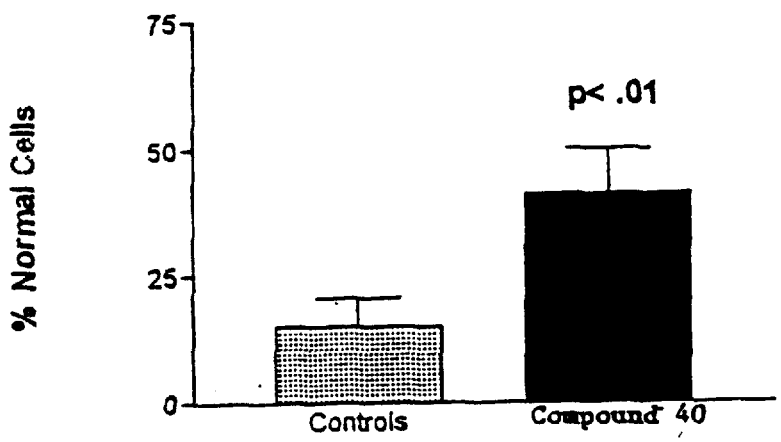
FIG. 2 shows tht effect of Compound 40 on survival of CA1 neurons at four days after the ischemic insult.
Figure 3:
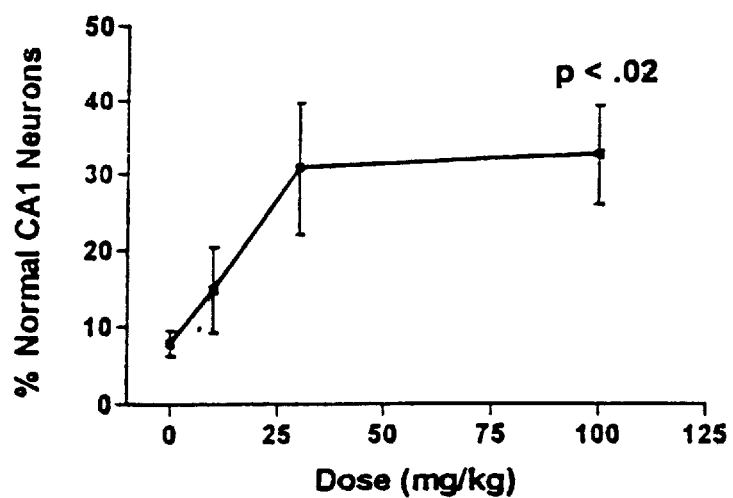
FIG. 3 shows the dose response for neuroprotective efficacy of Compound 40 when administered as described below.

FIG. 2 shows with statistical significance (p<0.01) that Compound 40 was neuroprotective at four days after the ischemic insult, a time when most of the hippocampal CA1 neurons had degenerated in vehicle-treated gerbils. Intact hippocampal CA1 neurons were counted and expressed as a ercent of the number of intact neurons found at that level of the dorsal hippocampus in control gerbils.

FIG. 3 shows with statistical significance (p<0.02) the neuroprotective effect of Compound 40.

As shown in FIG. 1, compound 40 reduced spectrin breakdown by approximately 50%. Compound 40 also more than doubled the number of surviving hippocampal CA1 neurons relative to controls, as shown in FIG. 2.

It is intended that each of the patents, applications, and printed publications mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound of the Formula I:

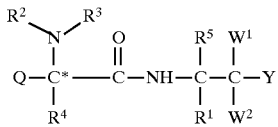

wherein:

C* denotes a carbon atom having a D-configuration;

Q has the formula G-B-$(CHR^{20})_q$— where $R^{20}$ is indepencly H or alkyl having from 1 to 4 carbons;

q is 0, 1, or 2:

B is selected from the group consisting of C(=O), S(=O), $S(=O)_2$, S, $CH_2$, a bond, NH and O;

G is selected from the group consisting of aryl having from about 6 to about 14 carbons, heteroaryl having from about 5 to about 14 ring atoms, aralkyl having from about 7 to about 15 carbons, alkyl having from 1 to about 10 carbons, heteroalkyl having from 2 to about 7 carbons, alkoxy having from 1 to about 10 carbons, arylsulfonyl, alkylsulfonyl, aralkyloxy having from about 7 to about 15 carbons, amino, a carbohydrate moiety and a carbohydrate moiecy containing one or more alkylaced hydroxyl groups, where any available hydrogen atom of said aryl, hecaroaryl, aralkyl, alkyl and amino groups is replaceable with a K group;

K is selected from the group consisting of halogen, CN, $NO_2$, lower alkyl, aryl, heteroaryl, aralkyl, aralkyloxy, guanidino, alkoxycarbonyl, alkoxy, hydroxy, carboxy, and amino, where any available hydrogen atom of said amino group is replaceable with a substicuent selected from the group consisting of an acyl group, 1 to 3 aryl and lower alkyl groups;

$R^1$ is selected from the group consisting of H, alkyl having from one to about 14 carbons, cycloalkyl having from 3 to about 10 carbons, aralkyl having from about 7 to about 15 carbons, heteroarylalkyl in which the heteroaryl ring contains from about 5 to about 14 ring atoms, a natural side chain of a D- or L-amino acid, and an unnatural side chain of a D- or L-amino acid, where any available hydrogen atom of said alkyl, cycloalkyl, aralkyl, and heteroarylalkyl groups is replaceable with a K group;

$R^2$ is selected from the group consisting of $C(=O)R^6$, $S(=O)_2R^6$, and a protecting group;

$R^6$ is selected from the group consisting of aryl having from about 6 to about 14 carbons, heteroaryl having from about 5 to about 14 ring atoms, aralkyl having from about 7 to about 15 carbons, alkyl having from 1 to about 10 carbons, where any available hydrogen atomn of said aryl, heteroaryl, aralkyl and alkyl groups is replaceable with a K group, heteroalkyl having from 2 to about 7 carbons, alkoxy having from 1 to about 10 carbons, and amino where any available hydrogen atom of said amino is replaceable with 1 or more alkyl groups;

$R^3$ is selected frotn the group consisting of H, lower alkyl, aralkyl, and a group of formula —$CO_2$—$R^{21}$ where $R^{21}$ is a lower alkyl group;

or $R^3$ taken together with $R^2$ form a phshalimido group;

or Q and $R^3$ taken together with —C* and —N($R^2$)— form a group of formula:

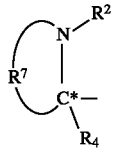

where $R^7$ is alkylene having from 2 to 5 carbons, where said alkylene group can comprise a carbon-carbon double bond, where any available hydrogen atom of said alkylene group is replaceable with a group selected from the group consisting of aryl, azide, CN, a protected amino group and $OSO_2$-aryl, wherein any available hydrogen atom of said aryl group is replaceable with a K group, where any available hydrogen atom of said aryl portion of said $OSO_2$-aryl group is replaceable with one or more K groups;

or $R^7$ has a structure represented by the formula:

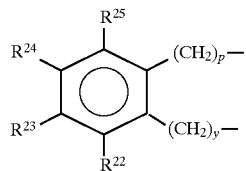

where p and y are independently 0 or 1, and $R^{22}$, $R^{23}$, $R^{24}$, and $R^{25}$ are indepenedently H or a K group;

$R^4$ and $R^5$ are each independently selected from the group consisting of H and lower alkyl;

$W^1$ and $W^2$ are selected such that $W^1$ is H and $W^2$ is $OC(=O)NH$—$R^{26}$ where $R^{26}$ is alkyl, or $W^1$ and $W^2$ are both alkoxy, or $W^1$ is OH and $W^2$ is selected from the group consisting of aralkyl, aralkyloxy, aryloxy, heteroaryloxy, heteroaralkyloxy, and $SO_3Z^1$ where $Z^1$ is a Group I or Group II counterion; or $W^1$ and $W^2$ taken together form a group selected from the group consisting of =O, =$NR^8$, =N(—O) $R^9$ —$S(CH_2)_2O$—, and —N ($R^{12}$) $(CH_2)_2N$ ($^{12}$)—;

$R^8$ is selected from the group consisting of $NH(C=O)NH_2$, hydroxyl, and lower alkoxy;

$R^9$ is selected from the group consisting of alkyl and aralkyl;

$R^{12}$ is selected from the group consisting of alkyl having from 1 to 4 carbons, and phenyl;

Y is selected from the group consisting of H, C(=C) $NR^{10}R^{11}$, $C(=O)OR^{10}$, CH=$N_2$, and $CH_2R^{13}$; or Y and $R^1$ taken together form —$(CH_2)_4N(Pr)$— is where Pr is H or a protecting group, provided that when Y and $R^1$ are taken together to form —$(CH_2)_4$ N(Pr)—, then $W^1$ and $W^2$ form =O;

$R^{10}$ and $R^{11}$ are each independently selected from the group consisting of H, alkyl having from 1 to about 10 carbons, where any available hydrogen atom of said alkyl groups is replaceable with a K group, aryl having from about 6 to about 14 carbons, and aralkyl having from about 7 to about 15 carbons;

$R^{13}$ is selected from the group consisting of L, lower alkyl, aralkyl, halogen, and a group O-M, wherein M has the structure:

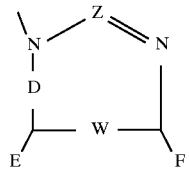

wherein:

Z is selected from the group consisting of N and $CR^{14}$;

W is selected from the group consisting of a double bond and a single bond;

D is selected from the group consisting of C=O and a single bond;

E and F are independently selected from the group consisting of $R^{14}$, $R^{15}$, and J;

or E and F taken together comprise a joined moiety, said joined moiety being selected from the group consisting of an aliphatic carbocyclic ring having from 5 to 7 carbons, an aromatic carbocyclic ring having from 5 to 7 carbons, an aliphatic heterocyclic ring having from 5 to 7 atoms and containing from 1 to 4 heteroatoms, and an aromatic heterocyclic ring having from 5 to 7 atoms and containing from 1 to 4 heteroatoms, said aliphatic carbocyclic ring, aromatic carbocyclic ring, aliphatic heterocyclic ring, and aromatic heterocyclic ring where any available hydrogen atom of said joint moiety it replaceable with J;

$R^{14}$ and $R^{15}$ are independently selected from the group consisting of H, alkyl having from 1 to 10 carbons, heteroaryl having from 1 to 10 carbons, alkanoyl having from 1 to 10 carbons, and aroyl, where any available hydrogen atom of said alkyl, heteroaryl, alkanoyl and aroyl groups is replaceable with J;

J is selected from the group consisting of halogen, $C(=O)OR^{16}$, $R^{16}OC(=O)$, $R^{16}OC(=O)NH$, OH, CN, $NO_2$, $NR^{16}R^{17}$, $N=C(R^{16})R^{17}$, $N=C(NR^{16}R^{17})_2$, $SR^{16}$, $OR^{16}$, phenyl, napthhyl, heceroaryl, and a cycloalkyl group having from 3 to 8 carbons;

$R^{16}$ and $R^{17}$ are independently H, alkyl having from 1 to 10 carbons, aryl, or heteroaryl, where any available hydrogen atom of said alkyl, aryl and heteroaryl groups is replaceable with K; and L is a phosphorus-containing enzyme reactive group having the formula:

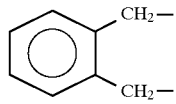

wherein;

m, n, and b are each indenendently 0 or 1;

$R^{18}$ and $R^{19}$ are each independently selected from the group consisting of H, lower alkyl, aryl, and hecrotaryl wherein any available hydrocrea atom of said lower alkyl, aryl, and heteroaryl group is replaceable with K;

or $R^{18}$ and $R^{19}$ taken together with $-(O)_m-P(=O)-(O)_n-$ form a 5–8 membered ring containing up to 3 hetero atoms, or $R^{16}$ and $R^{19}$ taken together with $-(O)_m-P(=O)-(O)_n-$ form a 5–8 membered ring, wherein any available hydrogen atom of said 5–8 membered ring is replaceable with K.

2. The compound of claim 1 wherein:

$R^1$ is selected from the group consisting of benzyl, p-benzyloxybenzyl, $-(CH_2)_4-NHC(=O)-O-CH_2-C_6H_5$; $-(CH_2)_4-NHC(=O)-O-t-C_4H_9$, and $-(CH_2)_4-NHSO_2-C_6H_5$;

$R_3$, $R_4$, and $R_5$ are each H;

$W^1$ and $W^2$ together form $-C(=O)-$;

Y is H or $CH_2F$;

B is CO, O, S, $SO_2$ or a bond;

$R^2$ is $-C(=O)CH_3$, or $-S(=O)_2R^6$ wherein $R^6$ is methyl, p-fluorophenyl, dimethylamino, ethyl, 2-thienyl, 2-isoxazolyl, phenyl, p-methylphenyl, 4-N-methylimidazolyl, or 2-naphthyl;

G is tetrahydroisoquinolinyl, benzyl, 3-indolyl, phenyl, N-methylbenzylamino, p-benzyloxyphenyl, or 2-thienyl;

or Q and $R^3$ together form $-(CH_2)_3-$.

3. The compound of claim 1 wherein q is 0;B is a bond; G is benzyl or 2-thienyl; Y is H; $R^1$ is benzyl; and $R^2$ is $-S(=O)_2R^6$ wherein $R^6$ is methyl, phenyl, or 2-thienyl.

4. The compound of claim 1 wherein q is 1; G is tetrahydroisoquinolinyl, benzyl, 3-indolyl, phenyl, N-methylbenzylamino, p-benzyloxyphenyl; and $R^2$ is $-C(=O)CH_3$, or $-S(=O)_2R^6$ wherein $R^6$ is methyl, p-fluorophenyl, dimethylamino, ethyl, 2-thienyl, 2-isoxazolyl, p-methylphenyl, 4-N-methylimidazolyl, or 2-naphthyl.

5. The compound of claim 4 wherein G is benzyl; and $R^2$ is $-C(=O)CH_3$ or $-S(=O)_2R^6$ wherein $R^6$ is methyl, p-fluorophenyl, dimethylamino, ethyl, 2-isoxazolyl, p-methylphenyl, 4-N-methylimidazolyl, or 2-naphthyl.

6. The compound of claim 5 wherein $R^2$ is $-S(=O)_2CH_3$.

7. The compound of claim 1 wherein q is 2; B is S; G is benzyl; Y is H; $R^1$ is benzyl; and $R^2$ is $-S(=O)_2CH_3$.

8. The compound of claim 1 wherein G is alkyl, benzyl, tetrahydroisoquinolyl, 3-indolyl, phenyl, N-methylbenzylamino, substituted benzyl, 2-thienyl or p-benzyloxyphenyl.

9. The compound of claim 1 wherein Q and $R^3$ taken together have a formula selected from the group consisting of $-(CH_2)_3-$, $-CH_2-CH(OSO_2C_6H_5)-CH_2-$, $-CH_2-CH(OSO_2C_6H_4CH_3)-CH_2-$, $-CH_2-CH(N_3)-CH_2-$, $-CH_2-CH(CN)-CH_2-$, $-CH_2-CH=CH-$, and

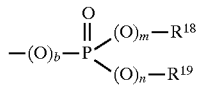

10. The compound of claim 1 wherein B is selected from the group consisting of $-C(=O)-$, $-O-$, $-S-$, $-S(=O)_2-$, and a bond.

11. The compund of claim 1 wherein $R^1$ is selected from the group consisting of benzyl, substituted benzyl, a lysyl sidechain, and a lysyl sidechain bearing one or more protectring groups.

12. The compound of claim 1 wherein $R^1$ is selected from the group consisting of alkyl, benzyl, p-benzyloxybenzyl, 2-pyridylmethyl, $-(CH_2)_4-NHC(=O)-O-CH_2-C_6H_5$, $-(CH_2)_4-NHC(=O)-O-t-C_4H_9$, and $-(CH_2)_4-NHSO_2-C_6H_5$.

13. The compound of claim 12 wherein said alkyl group is selected from the group consisting of ethyl, isobutyl, and t-butyl.

14. The compound of claim 1 wherein $W^1$ and $W^2$ are taken together to form $-C(=O)$, and $R^1$ and Y together form $-(CH_2)_4-N(Pr)-$where Pr is selected from the group consisting of H and t-butoxycarbonyl.

15. The compound of claim 1 wherein $R^2$ is selected from the group consisting of t-butyloxycarbonyl, $-S(=O)_2R^6$, and $-C(=O)CH_3$.

16. The compound of claim 15 wherein $R^2$ is $-S(=O)_2R^6$, said $R^6$ being selected from the group consisting of alkyl, substituted alkyl, aryl, substituted aryl, heteroaryl, and substituted heteroaryl.

17. The compound of claim 16 wherein $R^2$ is selected from the group consisting of $-S(=O)_2CH_3$, $-S(=O)_2CH_2CH_3$, p-fluorophenylsulfonyl, 2-thienylsulfonyl, 2-isoxazolesulfonyl, phenylsulfonyl, p-methylphenylsulfonyl, 4-(N-methylimidazole)sulfonyl, and 2-naphthylsulfonyl.

18. The compound of claim 1 wherein Y is selected from the group consisting of H and $CH_2F$.

19. The compound of claim 1 wherein $W^1$ and $W^2$ taken together form —C(=O).

20. The compound of claim 1 wherein $W^1$ is OH and $W^2$ is $SO_3Z^1$ where $Z^1$ is Na.

21. The compound of claim 1 wherein $W^1$ is H and $W^2$ is OC(=O)NH—$R^{26}$ where $R^{26}$ is alkyl.

22. The compound of claim 1 wherein $W^1$ is OH and $W^2$ is aralkyl.

23. The compound of claim 1 wherein $W^1$ is OH and $W^2$ is aralkyloxy.

24. The compound of claim 1 wherein $W^1$ is OH and $W^2$ is aryloxy.

25. The compound of claim 1 wherein $W^1$ is OH and $W^2$ is heteroaryloxy.

26. The compound of claim 1 wherein $W^1$ is OH and $W^2$ is heteroaralkyloxy.

27. The compound of claim 1 wherein $W^1$ and $W^2$ are both alkoxy.

28. The compound of claim 1 wherein $W^1$ and $W^2$ taken together form a group selected from the group consisting of =$NR^8$, =N(→O)$R^9$, —S(CH$_2$)$_2$O—, and —N($R^{12}$)(CH$_2$)$_2$N($R^{12}$)—.

29. The comnpolund of claim 11 wherein B is selected fromm the group consisting of —(C=O)—, —O—, a bond, SO$_2$, and —S—; Y is selected from the group consisting of H and CH$_2$F; $R^1$ is selected from the group consisting of benzyl, substituted benzyl, a lysyl sidechain, and a lysyl sidechain bearing one or more protecting groups; and $R^2$ is selected from the group consisting of t-butyloxycarbonyl, —C(=O)CH$_3$, and —S(=O)$_2R^6$.

30. The compound of claim 23 wherein $R^6$ is selected from the group consisting of alkyl, substituted alkyl, aryl, substituted aryl, heteroaryl, and substituted heteroaryl.

31. The compound of claim 1 wherein Q is benzyloxymethyl; $R^1$ is benzyl; $R^2$ is —SO$_2$CH$_3$; $R_3$, $R_4$, $R_5$ and Y are each H; and $W^1$ and $W^2$ together form —C(=O)—.

32. A composition for inhibiting a protease selected from the group consisting of serine proteases and cysteine proteases comprising a compound of claim 1.

33. A composition for inhibiting a protease selected from the group consisting of serine proteases and cysteine proteases comprising a compound of claim 1 in an enantiomerically enriched amount.

34. A composition of claim 33 wherein the enantiomerically enriched amount of the compound of claim 1 is an amount greater than about 75%.

35. A composition of claim 33 wherein the enantiomerically enriched amount of the compound of claim 1 is an amount greater than about 90%.

36. A composition of claim 33 wherein the enantiomerically enriched amount of the compound of claim 1 is about 100%.

37. A composition for inhibiting a protease selected from the group consisting of serine proteases and cysteine proteases consisting essentially of a compound of claim 1.

38. A method for inhibiting a protease comprising contacting a protease selected from the group consisting of serine proteases and cysteine proteases with an inhibitory amount of a compound of claim 1.

39. A method for inhibiting a protease comprising contacting a protease selected from the group consisting of serine proteases and cysteine proteases with an inhibitory amount of a composition comprising a compound of claim 1 in an enantiomerically enriched amount.

40. A method of claim 38 wherein the enantiomerically enriched amount of the compound of claim 1 is an amount greater than about 75%.

41. A method of claim 38 wherein the enantiomerically enriched amount of the compound of claim 1 is an amount greater than about 90%.

42. A method of claim 38 wherein the enantiomerically enriched amount of the compound of claim 1 is about 100%.

43. A method for inhibiting a protease comprising contacting a protease selected from the group consisting of serine proteases and cysteine proteases with an inhibitory amount of a composition consisting essentially of a compound of claim 1.

\* \* \* \* \*

UNITED STATES PATENT AND TRADEMARK OFFICE
CERTIFICATE OF CORRECTION

PATENT NO. : 5,852,007
DATED : December 22, 1998
INVENTOR(S) : Chatterjee

It is certified that error appears in the above-identified patent and that said Letters Patent is hereby corrected as shown below:

On the title page, under "OTHER PUBLICATIONS", at "Fehrentz et al.", second line thereof, please delete "αlAmino" and insert --α-Amino-- therefor.

On page 2, under "OTHER PUBLICATIONS", first column, at "Revesz et al.", second line thereof, please delete "Acyloxymethy" and insert --Acyloxymethyl-- therefor.

On page 2, under "OTHER PUBLICATIONS", second column, at "Schechter et al.", second line thereof, please insert --*Biochem.*-- after "Papain" but before "*Biophys.*"

In column 1, line 13, please delete "herby" and insert --hereby-- therefor.

In column 5, line 60, please delete "2isoxazolesulfonyl" and insert --2-isoxazolesulfonyl-- therefor.

In column 6 line 41, please delete "ethodologies" and insert -- methodologies-- therefor.

In column 9, line 26, please delete "1to 10" and insert --1 to 10-- therefor.

In column 9, line 58, please delete "4-Nmethylimidazolyl" and insert --4-N-methylimidazolyl-- therefor.

UNITED STATES PATENT AND TRADEMARK OFFICE
CERTIFICATE OF CORRECTION

PATENT NO. : 5,852,007
DATED : December 22, 1998
INVENTOR(S) : Chatterjee

It is certified that error appears in the above-identified patent and that said Letters Patent is hereby corrected as shown below:

In column 10, line 4, please delete "p-methyiphenyl" and insert --p-methylphenyl-- therefor.

In column 10, lines 51-52, please delete " 'heteroarylaklyl' " and insert --"heteroarylalkyl"-- therefor.

In column 11, Table I, third line thereof, please delete "$CH_6H_5-CH_2-$" and insert -- $C_6H_5-CH_2-$ -- therefor.

In column 15, line 50, please delete "Celites®" and insert --Celite®-- therefor.

In column 21, lines 29-30, please delete the sentence "The symbol "*" denotes a D-configuration around the indicated carbon atom."

In column 27, line 21, please delete "5.10–470" and insert --5.10–4.70-- therefor.

In column 30, lines 46-47, please delete "(m, 111H)" and insert --(m, 11H)-- therefor.

In column 36, line 15, please insert --Synthesis-- before "of Compound 55--.

UNITED STATES PATENT AND TRADEMARK OFFICE
CERTIFICATE OF CORRECTION

PATENT NO. : 5,852,007
DATED : December 22, 1998
INVENTOR(S) : Chatterjee

It is certified that error appears in the above-identified patent and that said Letters Patent is hereby corrected as shown below:

In column 40, line 23, please delete "(softening to melt);;R$f$" and insert --(softening to melt); R$f$-- therefor.

In column 41, line 11, please delete "triehylamine" and insert --triethylamine-- therefor.

In column 52, line 60, please delete "&.50–7.00" and insert --7.50–7.00-- therefor.

In column 54, line 65, please delete "4.05 ((dd,1H)" and insert --4.05 (dd, 1H)-- therefor.

In column 57, line 36, please delete "3.90 (mn, 1H)" and insert --3.90 (m, 1H)-- therefor.

In column 63, line 30, please delete "3.25 (mn, 2H)" and insert --3.25 (m, 2H)-- therefor.

In column 65, line 56, please delete "SN$^2$ fashion" and insert --S$_N$2 fashion-- therefor.

In column 65, line 66, please delete "3.30–3.10 (mn, 3H)" and insert --3.30–3.10 (m, 3H)-- therefor.

In column 72, line 2, please delete "incorporated y reference" and insert --incorporated by reference-- therefor.

UNITED STATES PATENT AND TRADEMARK OFFICE
CERTIFICATE OF CORRECTION

PATENT NO. : 5,852,007
DATED : December 22, 1998
INVENTOR(S) : Chatterjee

It is certified that error appears in the above-identified patent and that said Letters Patent is hereby corrected as shown below:

In column 72, line 14, please delete "Cambribge" and insert --Cambridge-- therefor.

In column 72, line 15, please delete "Cambribge" and insert --Cambridge-- therefor.

In column 72, line 36, please delete "ercent" and insert --percent-- therefor.

In column 72, lines 63-64, Claim 1, please delete "independencly" and insert --independently-- therefor.

In column 73, line 9, Claim 1, please delete "moiecy" and insert --moiety-- therefor.

In column 73, line 10, Claim 1, please delete "alkylaced" and insert --alkylated-- therefor.

In column 73, line 12, Claim 1, please delete "hecaroaryl" and insert --heteroaryl-- therefor.

In column 73, line 18, Claim 1, please delete "substicuent" and insert --substituent-- therefor.

In column 73, line 37, Claim 1, please delete "atomn" and insert --atom-- therefor.

UNITED STATES PATENT AND TRADEMARK OFFICE
CERTIFICATE OF CORRECTION

PATENT NO. : 5,852,007
DATED : December 22, 1998
INVENTOR(S) : Chatterjee

It is certified that error appears in the above-identified patent and that said Letters Patent is hereby corrected as shown below:

In column 73, line 43, Claim 1, please delete "frotn" and insert --from-- therefor.

In column 73, line 45, Claim 1, please delete "phshalimido" and insert --phthalimido-- therefor.

In column 74, line 23, Claim 1, please delete "=N(-O) R$^9$" and insert -- =N(→O) R$^9$, -- therefor.

In column 74, line 24, Claim 1, please delete "($^{12}$)--" and insert --(R$^{12}$)--- therefor.

In column 74, line 31, Claim 1, please delete "C(=C)" and insert --C(=O)-- therefor.

In column 75, line 10, Claim 1, please delete "it replaceable" and insert --is replaceable-- therefor.

In column 75, line 22, Claim 1, please delete "heceroaryl" and insert --heteroaryl-- therefor.

In column 75, line 40, Claim 1, please delete "hecrotaryl" and insert --heteroaryl-- therefor.

UNITED STATES PATENT AND TRADEMARK OFFICE
CERTIFICATE OF CORRECTION

PATENT NO. : 5,852,007
DATED : December 22, 1998
INVENTOR(S) : Chatterjee

It is certified that error appears in the above-identified patent and that said Letters Patent is hereby corrected as shown below:

In column 75, lines 40-41, Claim 1, please delete "hydrocrea" and insert --hydrogen-- therefor.

In column 75, line 46, Claim 1, please delete "$R^{16}$ and $R^{19}$" and insert --$R^{18}$ and $R^{19}$-- therefor.

In column 76, line 19, Claim 8, please delete "tetrahydroisoquinolyl" and insert --tetrahydroisoquinolinyl-- therefor.

In column 76, lines 39-40, Claim 11, please delete "protectring" and insert --protecting-- therefor.

In column 77, line 23, Claim 29, please delete "comnpolund" and insert --compound-- therefor.

In column 77, line 24, Claim 29, please delete "fromm" and insert -- from-- therefor.

Signed and Sealed this

Eighteenth Day of April, 2000

Attest:

Q. TODD DICKINSON

*Attesting Officer*  *Director of Patents and Trademarks*